(12) United States Patent
Ganesh et al.

(10) Patent No.: US 11,464,874 B2
(45) Date of Patent: Oct. 11, 2022

(54) TREATING METASTATIC CANCER AND MODEL SYSTEMS FOR METASTATIC DISEASE

(71) Applicant: MEMORIAL SLOAN-KETTERING CANCER CENTER, New York, NY (US)

(72) Inventors: Karuna Ganesh, New York, NY (US); Manuel Valiente, Madrid (ES); Joan Massague, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 152 days.

(21) Appl. No.: 16/263,677

(22) Filed: Jan. 31, 2019

(65) Prior Publication Data
US 2019/0167817 A1 Jun. 6, 2019

Related U.S. Application Data

(63) Continuation of application No. PCT/US2017/045145, filed on Aug. 2, 2017.

(60) Provisional application No. 62/370,108, filed on Aug. 2, 2016.

(51) Int. Cl.
| | | |
|---|---|---|
| *A61K 48/00* | (2006.01) |
| *C12N 15/113* | (2010.01) |
| *C12Q 1/02* | (2006.01) |
| *A61P 35/04* | (2006.01) |
| *G01N 33/50* | (2006.01) |
| *A61K 31/337* | (2006.01) |
| *A61K 31/519* | (2006.01) |
| *A61K 45/06* | (2006.01) |

(52) U.S. Cl.
CPC ........ *A61K 48/0066* (2013.01); *A61K 31/337* (2013.01); *A61K 31/519* (2013.01); *A61K 48/0016* (2013.01); *A61K 48/0083* (2013.01); *A61K 48/0091* (2013.01); *A61P 35/04* (2018.01); *C12N 15/113* (2013.01); *C12Q 1/025* (2013.01); *G01N 33/5011* (2013.01); *A61K 45/06* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 8,138,313 B2 | 3/2012 | Kelm et al. | |
| 2011/0171290 A1* | 7/2011 | Altevogt | A61P 35/04 |
| | | | 424/450 |
| 2014/0120117 A1 | 5/2014 | Kelm et al. | |
| 2016/0194639 A1* | 7/2016 | Massague | A61P 35/04 |
| | | | 514/44 A |
| 2020/0345854 A1* | 11/2020 | Yu | A61K 47/6849 |

FOREIGN PATENT DOCUMENTS

| | | |
|---|---|---|
| EP | 2 357 003 A2 | 8/2011 |
| WO | WO 2007/114550 A1 | 10/2007 |
| WO | WO 2008/023946 A1 | 2/2008 |
| WO | WO 2008/046529 A1 | 4/2008 |
| WO | WO 2008/151819 A2 | 12/2008 |
| WO | WO 2011/146382 A1 | 11/2011 |
| WO | WO 2014/093701 A1 | 6/2014 |
| WO | WO 2014/165825 A2 | 10/2014 |
| WO | WO 2015/042303 A1 | 3/2015 |
| WO | WO 2015/048577 A2 | 4/2015 |

OTHER PUBLICATIONS

Burdett et al., Cochrane Database Syst. Rev. 2015, Issue 3. Art. No. CD011430, 68 pages.*
Carceller et al., Journal of Pediatric Surgery, vol. 36, No. 5, May 2001: pp. 755-759.*
Allgayer et al., "Prognostic factors in gastric cancer," Br J Surg 84:1651-1664 (1997).
Altevogt et al., "L1CAM in human cancer," Int J Cancer 138:1565-1576 (2016).
Aragona et al., "A Mechanical Checkpoint Controls Multicellular Growth through YAP/TAZ Regulation by Actin-Processing Factors," Cell 154:1047-1059 (2013).
Ashkenazi et al., "Death Receptors: Signaling and Modulation," Science 281:1305-1308 (1998).
Bao et al., "Targeting Cancer Stem Cells through L1CAM Suppresses Glioma Growth," Cancer Research, 68(15):6043-6048 (2008).
Ben et al., "Positive Expression of L1-CAM is Associated with Perineural Invasion and Poor Outcome in Pancreatic Ductal Adenocarcinoma," Ann Surg Oncol. 17:2213-2221 (2010).
Benham-Pyle et al., "Mechanical strain induces E-cadherin-dependent Yap1 and β-catenin activation to drive cell cycle entry," Science 348(6238): 1024-1027 (2015).
Blouw et al., "The hypoxic response of tumors is dependent on their microenvironment," Cancer Cell 4:133-146 (2003).
Boo et al., "L1 Expression as a Marker for Poor Prognosis, Tumor Progression, and Short Survival in Patients with Colorectal Cancer," Ann Surg Oncol 14(5): 1703-1711 (2007).
Bos et al., "Genes that mediate breast cancer metastasis to the brain," Nature 459(7249):1005-1009 (2009).
Carbonell et al., "The Vascular Basement Membrane as "Soil" in Brain Metastasis," PloS ONE 4(6):e5857 (2009).
Castellani et al., "Cis and trans interactions of L1 with neuropilin-1 control axonal responses to semaphorin 3A," EMBO J 21(23):6348-6357 (2002).
Chambers et al., "Clinical Targets for Anti-Metastasis Therapy," Adv Cancer Res 79:91-121 (2000).
Chambers et al., "Dissemination and Growth of Cancer Cells in Metastatic Sites," Nat Rev Cancer 2:563-572 (2002).
(Continued)

Primary Examiner — Sean McGarry
(74) *Attorney, Agent, or Firm* — Baker Botts L.L.P.

(57) ABSTRACT

The present invention relates to methods and compositions for inhibiting metastatic spread of cancer and/or inhibiting progression of pre-existing metastatic disease in a subject using L1CAM inhibition.

Figure 1A:
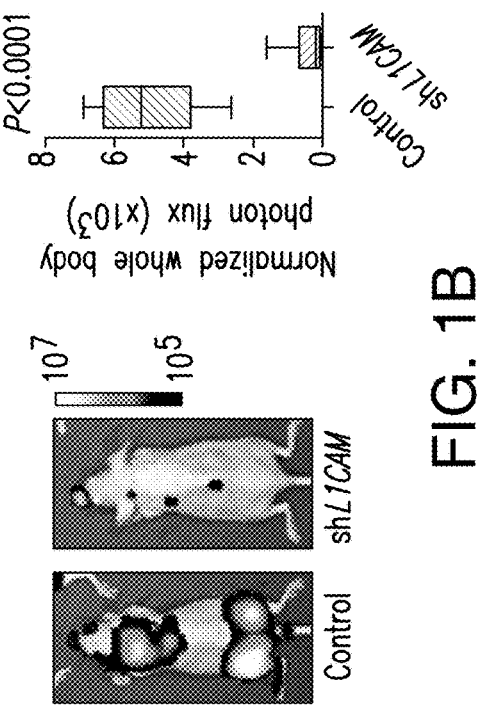
Figure 1B:
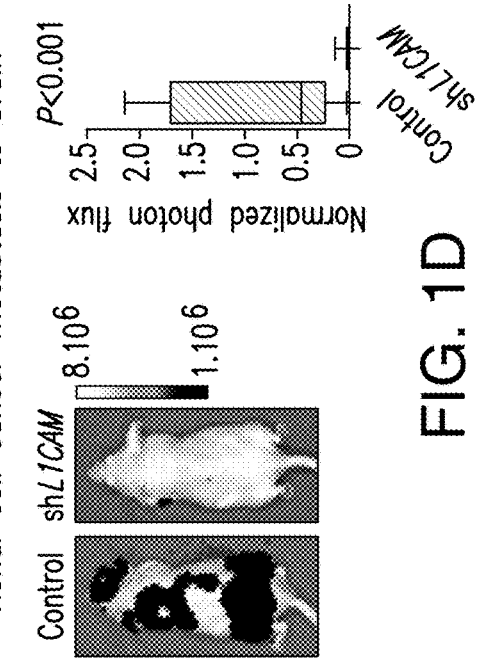
Figure 1C:
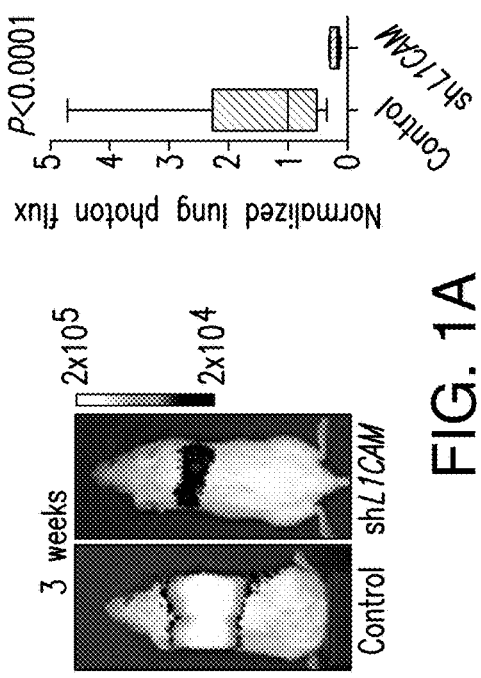

15 Claims, 59 Drawing Sheets
Specification includes a Sequence Listing.

(56) References Cited

OTHER PUBLICATIONS

Chen et al., "L1cam promotes tumor progression and metastasis and is an independent unfavorable prognostic factor in gastric cancer," J Hematol Oncol.6:43 (2013).
Cho et al., "Generation, characterization and preclinical studies of a human anti-L1CAM monoclonal antibody that cross-reacts with rodent L1CAM," mAbs 8(2):414-425 (2016).
Demyanenko et al., "Abnormalities in Neuronal Process Extension, Hippocampal Development, and the Ventricular System of L1 Knockout Mice," J Neurosci 19(12):4907-4920 (1999).
Dietrich et al., "Death receptors on reactive astrocytes: a key role in the fine tuning of brain inflammation?" Neurology 60:548-554 (2003).
Dippel et al., "Influence of L1-CAM expression of breast cancer cells on adhesion to endothelial cells," J Cancer Res Clin Oncol. 139:107-121 (2013).
Doberstein et al., "Antibody therapy to human L1CAM in a transgenic mouse model blocks local tumor growth but induces EMT," Int J Cancer 136:e326-e339 (2015).
Doberstein et al., "L1-CAM expression in ccRCC correlates with shorter patients survival times and confers chemoresistance in renal cell carcinoma cells," Carcinogenesis 32(3):262-270 (2011).
Donier et al., "L1CAM binds ErbB receptors through Ig-like Domains Coupling Cell Adhesion and Neuregulin Signalling," PLoS ONE 7(7):e40674 (2012).
Drost et al., "Organoid culture systems for prostate epithelial tissue and prostate cancer tissue," Nature Protocols 11(2):347-358 (2016).
Faltas et al., "Clonal Evolution of Chemotherapy-resistant Urothelial Carcinoma," Nat. Genet. 48(12):1490-1499 (2016).
Feld et al., "Sites of Recurrence in Resected Stage I Non-Small-Cell Lung Cancer: A Guide for Future Studies," J Clin Oncol 2:1352-1358 (1984).
Felding-Habermann et al., "A Single Immunoglobulin-like Domain of the Human Neural Cell Adhesion Molecule L1 Supports Adhesion by Multiple Vascular and Platelet Integrins," J Cell Biol 139(6):1567-1581 (1997).
Fidler, "The pathogenesis of cancer metastasis: the 'seed and soil' hypothesis revisited," Nat Rev Cancer 3:453-458 (2003).
Foekens et al., "Urokinase-Type Plasminogen Activator and Its Inhibitor PAI-1: Predictors of Poor Response to Tamoxifen Therapy in Recurrent Breast Cancer," J Natl Cancer Inst 87(10):751-756 (1995).
Fogel et al., "L1 adhesion molecule (CD 171) in development and progression of human malignant melanoma," Cancer Lett. 189:237-247 (2003).
Fogel et al., "L1 expression as a predictor of progression and survival in patients with uterine and ovarian carcinomas," Lancet 362:869-875 (2003).
Francia et al., "Mouse models of advanced spontaneous metastasis for experimental therapeutics," Nat Rev Cancer 11:135-141 (2011).
Ganesh et al., "Inhibition of Reactive Gliosis Attenuates Excitotoxicity-Mediated Death of Retinal Ganglion Cells," PLoS ONE 6(3):e18305 (2011).
Gavrilovic et al., "Brain metastases: epidemiology and pathophysiology," J Neuro-Oncol 75:5-14 (2005).
Gjorevski et al., "Designer matrices for intestinal stem cell and organoid culture," Nature 539:560-564 (2016).
Gupta et al., "Cancer Metastasis: Building a Framework," Cell 127:679-695 (2006).
Hai et al., "L1 Cell Adhesion Molecule Promotes Tumorigenicity and Metastatic Potential in Non-Small Cell Lung Cancer," Clin Cancer Res 18(7):1914-1924 (2012).
Hanahan et al., "Hallmarks of Cancer: The Next Generation," Cell 144:646-674 (2011).
Harbeck et al., "Invasion marker PAI-1 remains a strong prognostic factor after long-term follow-up both for primary breast cancer and following first relapse," Breast Cancer Res Treat 54:147-157 (1999).
Herron et al., "The intracellular interactions of the L1 family of cell adhesion molecules," Biochem J 419:519-531 (2009).

Heyn et al., "In Vivo MRI of Cancer Cell Fate at the Single-Cell Level in a Mouse Model of Breast Cancer Metastasis to the Brain," Magnetic Reson Med 56:1001-1010 (2006).
Hoffman et al., "Effects of Ethanol on Axon Outgrowth and Branching in Developing Rat Cortical Neurons," Neurosci. 157:556-565 (2008).
Hong et al., "Diverse Solid Tumors Expressing a Restricted Epitope of L1-CAM Can Be Targeted by Chimeric Antigen Receptor Redirected T Lymphocytes," J Immunother. 37(2):93-104 (2014).
International Search Report dated Dec. 21, 2017 in International Application No. PCT/US17/45145.
Kang et al., "A multigenic program mediating breast cancer metastasis to bone," Cancer Cell 3:537-549 (2003).
Karrison et al., "Dormancy of Mammary Carcinoma after Mastectomy," J Natl Cancer Inst 91(1):80-85 (1999).
Kienast et al., "Real-time imaging reveals the single steps of brain metastasis formation," Nat Med 16(1): 116-122 (2010).
Kim et al., "Astrocytes Upregulate Survival Genes in Tumor Cells and Induce Protection from Chemotherapy," Neoplasia 13(3):286-298 (2011).
Kim et al., "L1 cell adhesion molecule as a predictor for recurrence in pulmonary carcinoids and large-cell neuroendocrine tumors," APMIS 117:140-146 (2009).
Krammer, "CD95's deadly mission in the immune system," Nature 407:789-795 (2000).
Kulahin et al., "Fibronectin type III (FN3) modules of the neuronal cell adhesion molecule L1 interact directly with the fibroblast growth factor (FGF) receptor," Mol. Cell Neurosci 37:528-536 (2008).
Law et al., "An overview of the serpin superfamily," Genome Biol 7:216 (2006).
Lee et al., "A chimeric antibody to L1 cell adhesion molecule shows therapeutic effect in an intrahepatic cholangiocarcinoma model," Exp Mol Med. 44(4):293-302 (2012).
Leenders et al., "Antiangiogenic Therapy of Cerebral Melanoma Metastases Results in Sustained Tumor Progression via Vessel Co-Option," Clin Cancer Res 10:6222-6230 (2004).
Leenders et al., "Vessel Co-Option: How Tumors Obtain Blood Supply in the Absence of Sprouting Angiogenesis," Endothelium 9:83-87 (2002).
Leyland-Jones, "Human Epidermal Growth Factor Receptor 2-Positive Breast Cancer and Central Nervous System Metastases," J Clin Oncol 27(31):5278-5286 (2009).
Li et al., "Elevated PLGF contributes to small-cell lung cancer brain metastasis," Oncogene 32:2952-2962 (2013).
Lin et al., "Brain Metastases: The HER2 Paradigm," Clin Cancer Res 13(6):1648-1655 (2007).
Lin et al., "Reactive Astrocytes Protect Melanoma Cells from Chemotherapy by Sequestering Intracellular Calcium through Gap Junction Communication Channels," Neoplasia 12(9):748-754 (2010).
Lindenblatt et al., "Paclitaxel improved anti-L1CAM lutetium-177 radioimmunotherapy in an ovarian cancer xenograft model," EJNMMI Res. 4:54 (2014) 10 pages.
Lorger et al., "Capturing Changes in the Brain Microenvironment during Initial Steps of Breast Cancer Brain Metastasis," Am J Pathol 176(6):2958-2971 (2010).
Luo et al., "Nuclear cytokine-activated IKKα controls prostate cancer metastasis by repressing Maspin," Nature 446:690-694 (2007).
Lutterbach et al., "Long-term survival in patients with brain metastases," J Cancer Res Clin Oncol 128:417-425 (2002).
Maher et al., "Brain Metastasis: Opportunities in Basic and Translational Research," Cancer Res 69(15):6015-6020 (2009).
Malladi et al., "Metastatic Latency and Immune Evasion through Autocrine Inhibition of WNT," Cell 165:45-60 (2016).
Maness et al., "Neural recognition molecules of the immunoglobulin superfamily: signaling transducers of axon guidance and neuronal migration," Nat Neurosci 10:19-26 (2007).
Mechtersheimer et al., "Ectodomain shedding of L1 adhesion molecule promotes cell migration by autocrine binding to integrins," J Cell Biol 155(4):661-673 (2001).
Meuwissen et al., "Induction of small cell lung cancer by somatic inactivation of both Trp53 and Rb1 in a conditional mouse model," Cancer Cell 4:181-189 (2003).

(56) References Cited

OTHER PUBLICATIONS

Minn et al., "Genes that mediate breast cancer metastasis to lung," Nature 436(7050):518-524 (2005).
Mire et al., "Modulating Sema3A signal with a L1 mimetic peptide is not sufficient to promote motor recovery and axon regeneration after spinal cord injury," Mol. Cell. Neurosci. 37(2):222-235 (2008).
Moody et al., "Conditional activation of Neu in the mammary epithelium of transgenic mice results in reversible pulmonary metastasis," Cancer Cell 2:451-461 (2002).
Nguyen et al., "Metastasis: from dissemination to organ-specific colonization," Nat Rev Cancer 9:274-284 (2009).
Nguyen et al., "WNT/TCF signaling through LEF1 and HOXB9 mediates lung adenocarcinoma metastasis," Cell 138:51-62 (2009).
Oskarsson et al., "Metastatic Stem Cells: Sources, Niches, and Vital Pathways," Cell Stem Cell 14:306-321 (2014).
Palmieri et al., "Her-2 Overexpression Increases the Metastatic Outgrowth of Breast Cancer Cells in the Brain," Cancer Res 67(9):4190-4198 (2007).
Park et al., "Adoptive Transfer of Chimeric Antigen Receptor Re-Directed Cytolytic T Lymphocyte Clones in Patients with Neuroblastoma," Mol Ther. 15(4):825-833 (2007).
Perera et al., "In Vivo Magnetic Resonance Imaging for Investigating the Development and Distribution of Experimental Brain Metastases due to Breast Cancer," Transl Oncol 5:217-225 (2012).
Polleux et al., "The Slice Overlay Assay: A Versatile Tool to Study the Influence of Extracellular Signals on Neuronal Development," Sci STKE 136:19 (2002) 12 pages.
Qian et al., "Inhibition of Polo-like kinase 1 prevents the growth of metastatic breast cancer cells in the brain," Clin Exp Metastasis 28:899-908 (2011).
Rathjen et al., "Immunocytological and biochemical characterization of a new neuronal cell surface component (L1 antigen) which is involved in cell adhesion," EMBO J. 3(1):1-10 (1984).
Regales et al., "Dual targeting of EGFR can overcome a major drug resistance mutation in mouse models of EGFR mutant lung cancer," J Clin Invest 119(10):3000-3010 (2009).
Schafer et al., "Combined treatment of L1CAM antibodies and cytostatic drugs improve the therapeutic response of pancreatic and ovarian carcinoma," Cancer Letters 319:66-82 (2012).
Schafer et al., "L1CAM malfunction in the nervous system and human carcinomas," Cell Mol Life Sci 67:2425-2437 (2010).
Schildge et al., "Isolation and Culture of Mouse Cortical Astrocytes," Journal of Visualized Experiments 71:e50079 (2013).
Schmidt-Kittler et al., "From latent disseminated cells to overt metastasis: Genetic analysis of systemic breast cancer progression," PNAS USA 100(13):7737-7742 (2003).
Schmohl et al., "CD133, Selectively Targeting the Root of Cancer," Toxins 8:165 (2016) 19 pages.
Schouten et al., "Incidence of Brain Metastases in a Cohort of Patients with Carcinoma of the Breast, Colon, Kidney, and Lung and Melanoma," Cancer 94(10):2698-2705 (2002).
Schreiber et al., "Cancer Immunoediting: Integrating Immunity's Roles in Cancer Suppression and Promotion," Science 331:1565-1570 (2011).
Schroder et al., "Expression and prognostic value of L1-CAM in breast cancer," Oncol Rep 22:1109-1117 (2009).
Seike et al., "Interaction between lung cancer cells and astrocytes via specific inflammatory cytokines in the microenvironment of brain metastasis," Clin Exp Metastasis 28:13-25 (2011).

Siegel et al., "Transforming growth factor beta signaling impairs Neu-induced mammary tumorigenesis while promoting pulmonary metastasis," PNAS USA 100(14):8430-8435 (2003).
Sledge, "HER2011: The Changing Face of HER2-Positive Breast Cancer," Clin Breast Cancer 11(1):9 (2011).
Sofroniew et al., "Astrocytes: biology and pathology," Acta Neuropathol 119:7-35 (2010).
Steeg et al., "Brain metastases as preventive and therapeutic targets," Nat Rev Cancer 11:352-363 (2011).
Sung et al., "Targeting L1 cell adhesion molecule expression using liposome-encapsulated siRNA suppresses prostate cancer bone metastasis and growth," Oncotarget, 5(20):9911-9929 (2014).
Supplemental European Search Report dated Mar. 17, 2020 in Application No. EP 17837622.
Thies et al., "Overexpression of the cell adhesion molecule L1 is associated with metastasis in cutaneous malignant melanoma," Eur J Cancer 38:1708-1716 (2002).
Tischler et al., "L1CAM protein expression is associated with poor prognosis in non-small cell lung cancer," Mol Cancer 10:127 (2011) 11 pages.
Tsutsumi et al., "L1 Cell Adhesion Molecule (L1CAM) Expression at the Cancer Invasive Front is a Novel Prognostic Marker of Pancreatic Ductal Adenocarcinoma," J Surg Oncol 103:669-673 (2011).
Valastyan et al., "Tumor Metastasis: Molecular Insights and Evolving Paradigms," Cell 147(2):275-292 (2011).
Valiente et al., "Serpins Promote Cancer Cell Survival and Vascular Co-Option in Brain Metastasis," Cell 156(5):1002-1016 (2014).
Vanharanta et al., "Origins of Metastatic Traits," Cancer Cell 24(4):410-421 (2013).
Vos et al., "An Updated and Upgraded L1CAM Mutation Database," Human Mutation 31:E1102-1109 (2010).
Voura et al., "Involvement of Integrin $\alpha(v)\beta(3)$ and Cell Adhesion Molecule L1 in Transendothelial Migration of Melanoma Cells," Mol Biol Cell 12:2699-2710 (2001).
Wang et al., "Antibody Fragments Directed against Different Portions of the Human Neural Cell Adhesion Molecule L1 Act as Inhibitors or Activators of L1 Function," PLoS ONE 7(12):e52404 (2012).
Wang et al., "Astrocytic Fas ligand expression is required to induce T-cell apoptosis and recovery from experimental autoimmune encephalomyelitis," Eur J Immunol 43:115-124 (2013).
Weinspach et al., "Role of L1 cell adhesion molecule (L1CAM) in the metastatic cascade: promotion of dissemination, colonization, and metastatic growth," Clinical and Experimental Metastasis, 31:87-100 (2014).
Wiencken-Barger et al., "The Role of L1 in Axon Pathfinding and Fasciculation," Cereb Cortex 14:121-131 (2004).
Winslow et al., "Suppression of Lung Adenocarcinoma Progression by Nkx2-1," Nature 473:101-104 (2011).
Wolterink et al., "Therapeutic Antibodies to Human L1CAM: Functional Characterization and Application in a Mouse Model for Ovarian Carcinoma," Cancer Res. 70(6):2504-2515 (2010).
Zhao et al., "Inactivation of YAP oncoprotein by the Hippo pathway is involved in cell contact inhibition and tissue growth control," Genes & Dev. 21:2747-2761 (2007).
Zhu et al., "Prognostic and Predictive Gene Signature for Adjuvant Chemotherapy in Resected Non-Small-Cell Lung Cancer," J Clin Oncol 28:4417-4424 (2010).

* cited by examiner

L1CAM+ cells are quiescent: post-therapy residual disease

Colorectal Cancer

Similar results in breast and lung cancer

SEQUENCE LISTING

<160> NUMBER OF SEQ ID NOS: 6

<210> SEQ ID NO 1
<211> LENGTH: 58
<212> TYPE: DNA
<213> ORGANISM: Artificial Sequence
<220> FEATURE:
<223> OTHER INFORMATION: RNAi hairpin

<400> SEQUENCE: 1
ccggacgggc aacaacagca actttctcga gaaagttgct gttgttgccc gtttttg         58

<210> SEQ ID NO 2
<211> LENGTH: 21
<212> TYPE: DNA
<213> ORGANISM: Artificial Sequence
<220> FEATURE:
<223> OTHER INFORMATION: RNAi target

<400> SEQUENCE: 2
acgggcaaca acagcaactt t                                                21

<210> SEQ ID NO 3
<211> LENGTH: 58
<212> TYPE: DNA
<213> ORGANISM: Artificial Sequence
<220> FEATURE:
<223> OTHER INFORMATION: RNAi hairpin

<400> SEQUENCE: 3
ccggccactt gtttaaggag aggatctcga gatcctctcc ttaaacaagt ggtttttg        58

<210> SEQ ID NO 4
<211> LENGTH: 21
<212> TYPE: DNA
<213> ORGANISM: Artificial Sequence
<220> FEATURE:
<223> OTHER INFORMATION: RNAi target

<400> SEQUENCE: 4
ccacttgttt aaggagagga t                                                21

```
<210> SEQ ID NO 5
<211> LENGTH: 58
<212> TYPE: DNA
<213> ORGANISM: Artificial Sequence
<220> FEATURE:
<223> OTHER INFORMATION: RNAi hairpin

<400> SEQUENCE: 5
ccgggccaat gcctacatct acgttctcga gaacgtagat gtaggcattg gcttttg          58

<210> SEQ ID NO 6
<211> LENGTH: 21
<212> TYPE: DNA
<213> ORGANISM: Artificial Sequence
<220> FEATURE:
<223> OTHER INFORMATION: RNAi target

<400> SEQUENCE: 6
gccaatgcct acatctacgt t                                                  21
```

TREATING METASTATIC CANCER AND MODEL SYSTEMS FOR METASTATIC DISEASE

CROSS-REFERENCE TO RELATED APPLICATIONS

This application is a Continuation of International Patent Application No. PCT/US2017/045145, filed Aug. 2, 2017, which claims priority to U.S. Provisional Application No. 62/370,108 filed Aug. 2, 2016, the contents of each of which are hereby incorporated by reference in their entireties herein, and to each of which priority is claimed.

GRANT INFORMATION

This invention was made with government support under Grant Nos. CA163167 awarded by the National Institutes of Health and W81XWH-12-1-0074 awarded by the United States Army Medical Research and Materiel Command. The government has certain rights in the invention.

SEQUENCE LISTING

The specification further incorporates by reference the Sequence Listing submitted herewith via EFS on Jan. 31, 2019. Pursuant to 37 C.F.R. § 1.52(e)(5), the Sequence Listing text file, identified as 0727340822SL.txt, is 1,434 bytes and was created on Jan. 31, 2019. The Sequence Listing, electronically filed herewith, does not extend beyond the scope of the specification and thus does not contain new matter.

1. INTRODUCTION

The present invention relates to methods and compositions for inhibiting metastatic spread of cancer and/or inhibiting progression of pre-existing metastatic disease in a subject In particular embodiments, it provides for methods comprising treating the subject with an L1CAM inhibitor using a regimen that targets slow-growing metastatic cancer stem-like cells ("MetCSCs") as exist, for example, in post-chemotherapy residual disease. It further provides for models of metastatic disease comprising MetCSC-expressing L1CAM that may be used to study metastatic progression of cancer and to identify useful therapeutic agents.

2. BACKGROUND OF THE INVENTION

Despite recent advances in cancer therapeutics, metastasis remains the main cause of cancer death. Chemotherapy and targeted therapies for metastatic disease may induce tumor responses, but are nearly always followed by resistance and lethal relapse. The residual disease that persists after therapy and drives regrowth has been proposed to contain metastatic cancer stem-like cells (MetCSCs) that are particularly capable of self-renewal, and that are slow cell-cycling, tumor re-initiating and therapy resistant (Oskarsson et al., 2014; Hanahan et al., 2011; Malladi et al., 2016). Targeting MetCSCs may offer an important approach for treating metastatic cancer and micrometastatic residual disease in the adjuvant setting.

L1CAM was originally identified as a neuronal adhesion molecule (Rathjen et al., 1984; Maness and Schachner, 2007). L1CAM is a large, multidomain protein ectopically expressed at the invasion fronts of many solid tumors and universally associated with metastasis and poor prognosis (e.g., Altevogt et al., 2015). Metastatic lung and breast cancer single cells invading the brain use L1CAM to intimately stretch along blood vessels, in a process termed vascular co-option (Valiente et al., 2014; PCT/US2014/056379). RNAi-mediated L1CAM knockdown inhibits vascular co-option and prevents the outgrowth of brain macrometastases (PCT/US2014/056379).

3. SUMMARY OF THE INVENTION

The present invention relates to methods of preventing and treating metastatic disease, assay systems for identifying therapeutic agents, and compositions useful therefor.

It is based, at least in part, on the discovery that L1CAM is a marker of MetCSCs, and is expressed on these quiescent, very slowly dividing cells that can therefore escape standard chemotherapy and later re-initiate tumor growth. It is further based on the discovery that L1CAM-depletion inhibits the initiation of metastasis not only in the brain, but also in the lungs, liver and bone from breast, lung, colon and renal cancer xenografts, demonstrating the importance of L1CAM in the initiation of multi-organ metastasis. In particular, inducible L1CAM knockdown in advanced macrometastatic xenografts was observed to inhibit the progression of metastases, highlighting the clinical relevance of L1CAM inhibition in established metastatic disease. It is further based, in part, on the discoveiesy that L1CAM inhibition inhibited the growth of chemoresistant lung cancer xenografts, supporting a distinct mechanism of action from cytotoxic agents, and that inhibition of L1CAM was observed to render chemoresistant tumor cells sensitive to chemotherapy.

4. BRIEF DESCRIPTION OF THE FIGURES

FIGS. 1A-1D. L1CAM is required for multi-organ metastasis, and knockdown of L1CAM expression in cancer cells inhibits (reduces) (A) breast cancer metastasis to lung; (B) breast cancer metastasis to bone; (C) colon cancer metastasis to liver; and (D) renal cell cancer metastasis to brain.

Figure 2:
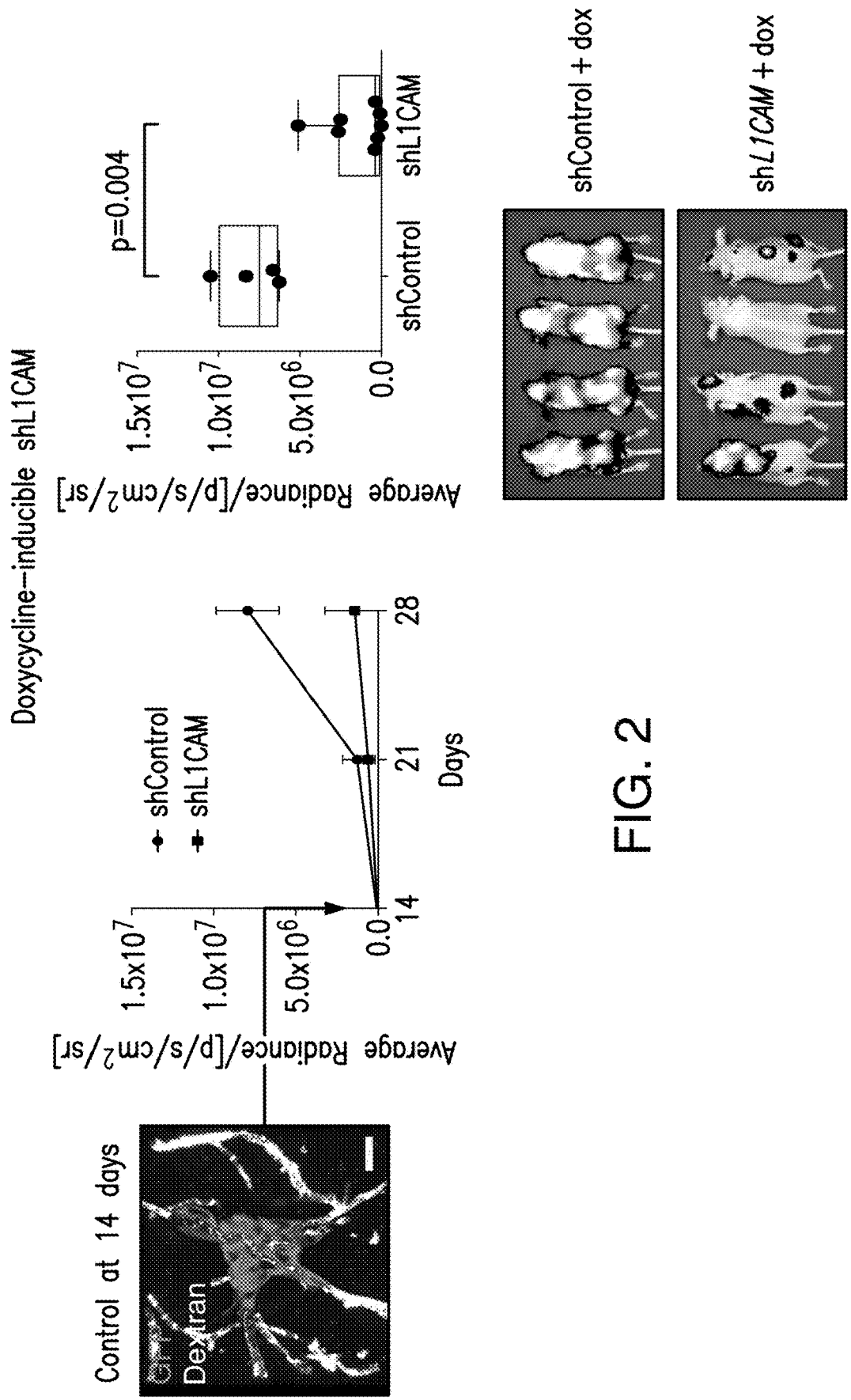

FIG. 2. Use of doxycycline-inducible "knockdown" of L1CAM to determine effect of L1CAM inhibition on established metastases.

Figure 3A:
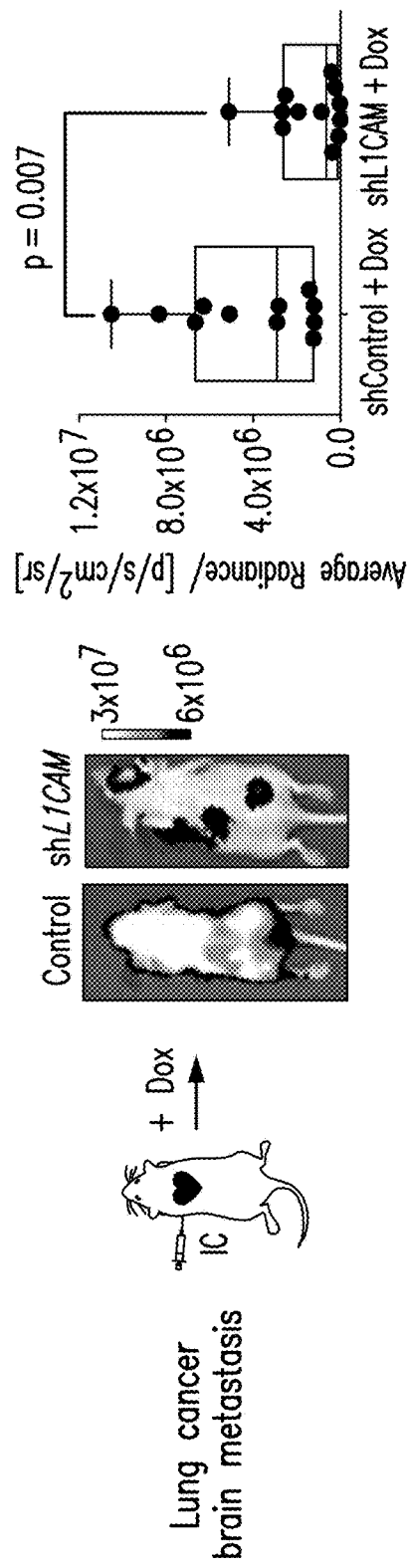
Figure 3B:
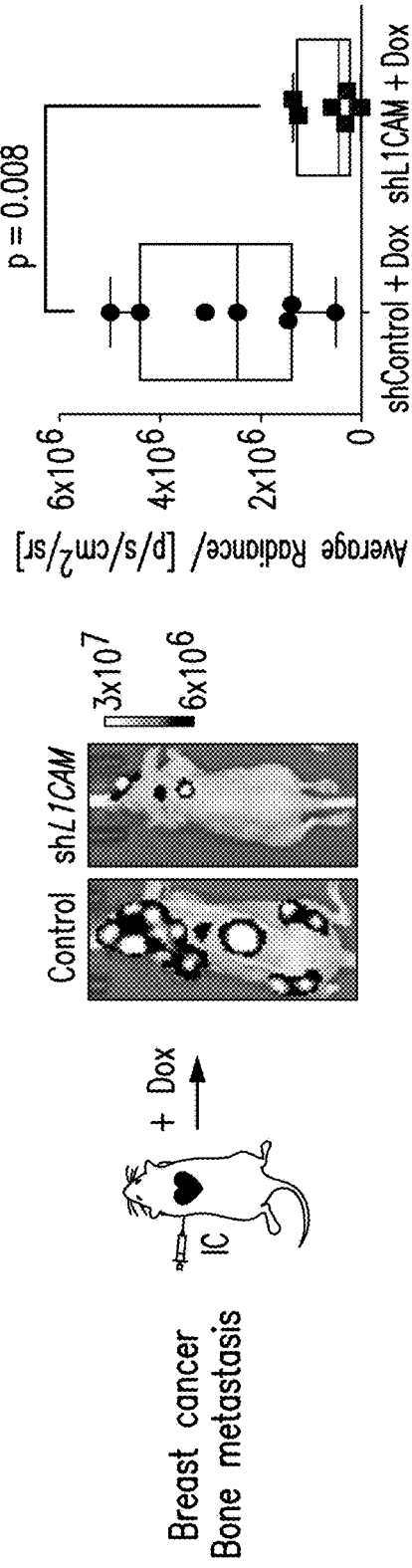
Figure 3C:
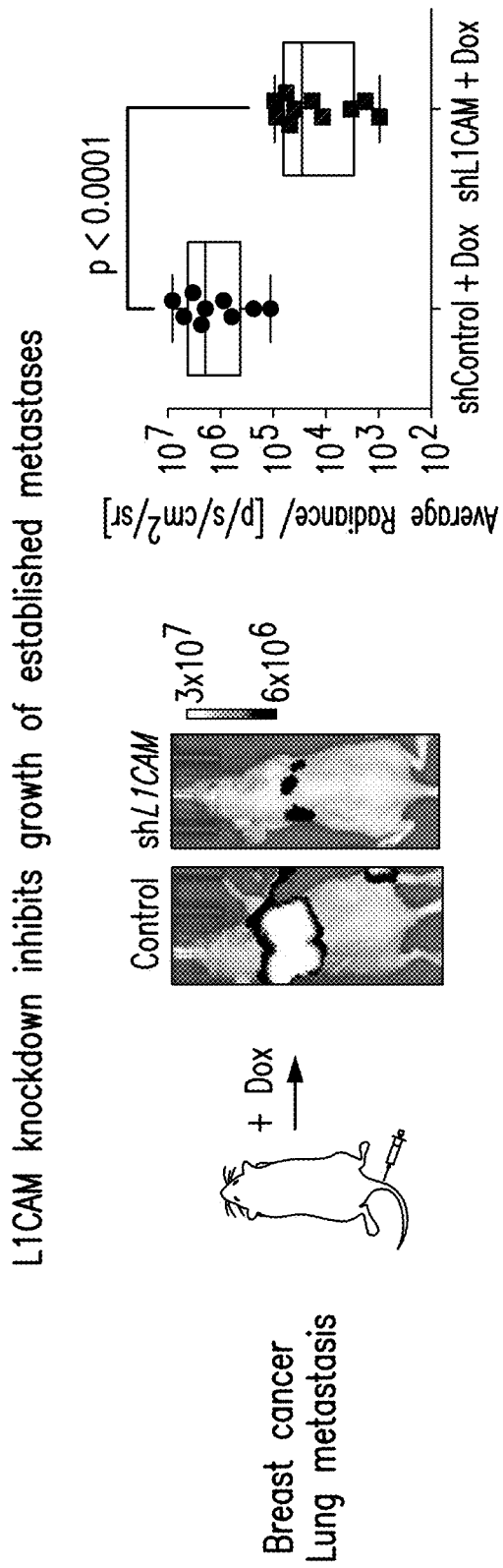

FIGS. 3A-3C. L1CAM knockdown inhibits the growth of established metastases, including (A) metastasis of lung cancer to brain; (B) metastasis of breast cancer to bone; and (C) metastasis of breast cancer to lung.

Figure 4B:
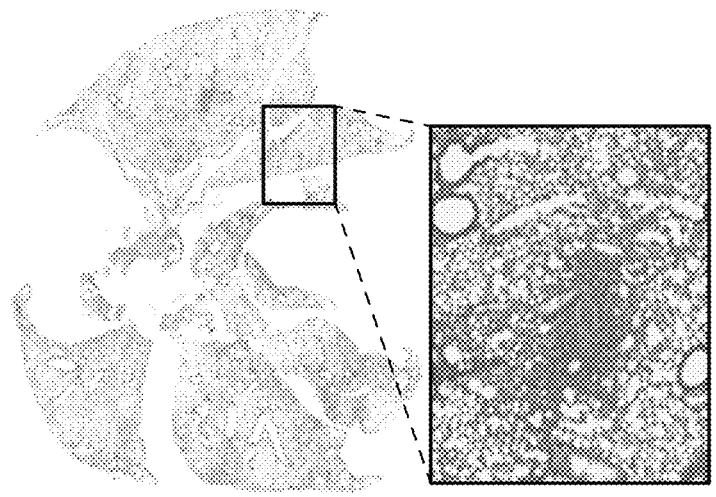
Figure 4A:
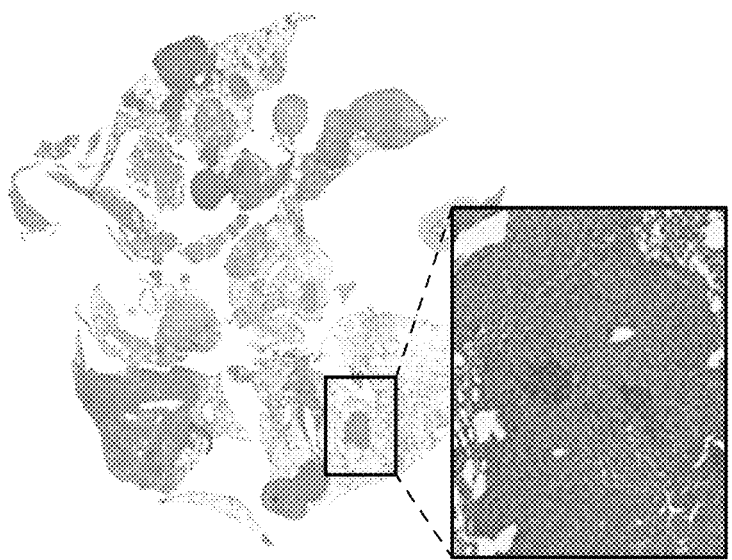

FIGS. 4A-4B. Histologic comparison of established metastasis (A) without or (B) with, L1CAM inhibition.

Figure 5A:
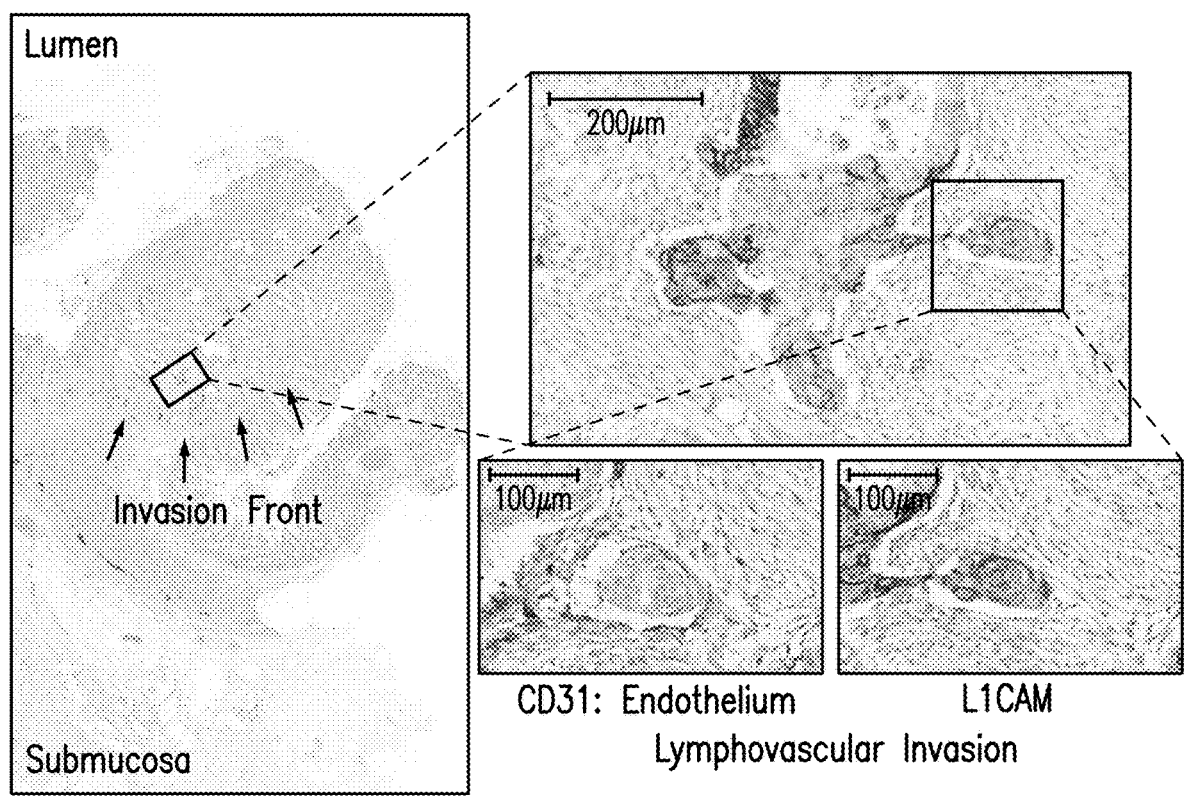
Figure 5B:
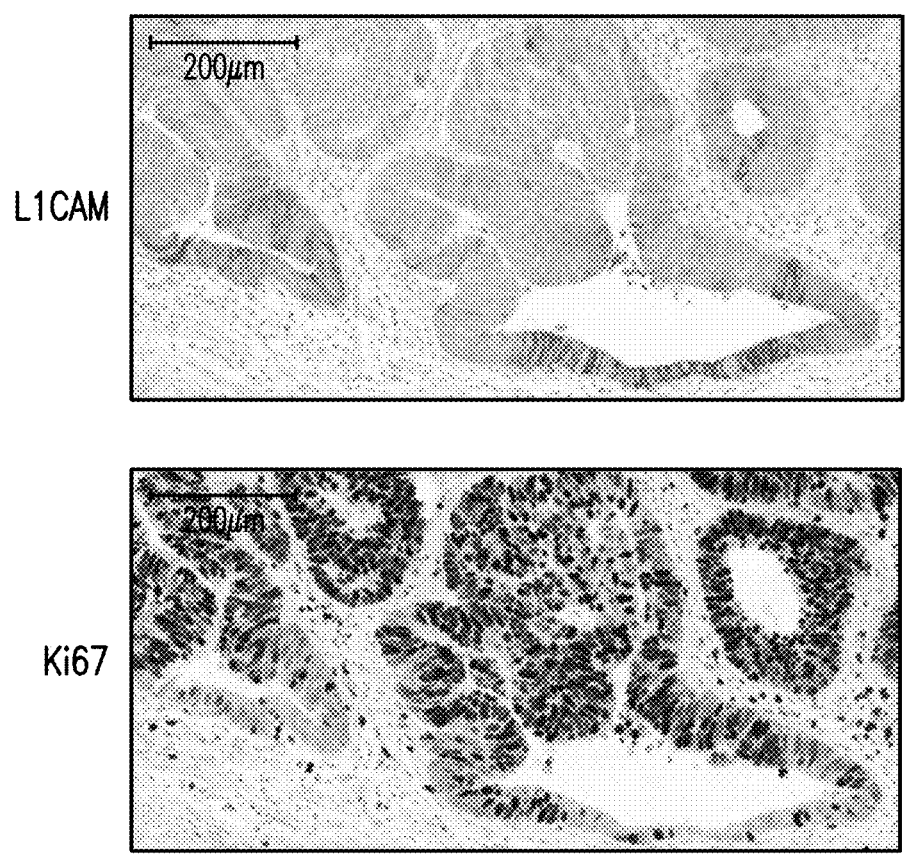

FIGS. 5A and 5B. Expression of L1CAM at the primary tumor invasion front. (A) The primary tumor invasion front is strongly L1CAM+; (B) L1CAM+ cells at the invasion front are quiescent (comparative low KI67 expression).

FIGS. 6A-6D. Comparison of expression of L1CAM in (A) primary colorectal tumor and (B) a liver metastasis. (C) shows the percent of the total area that is L1CAM+. (D) shows lack of detectable L1CAM expression in normal colon.

Figure 7C:
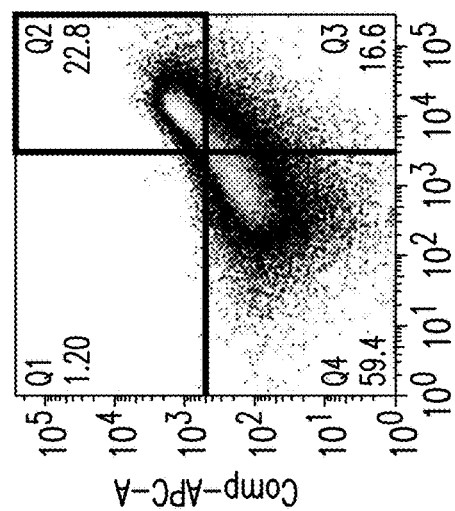
Figure 7B:
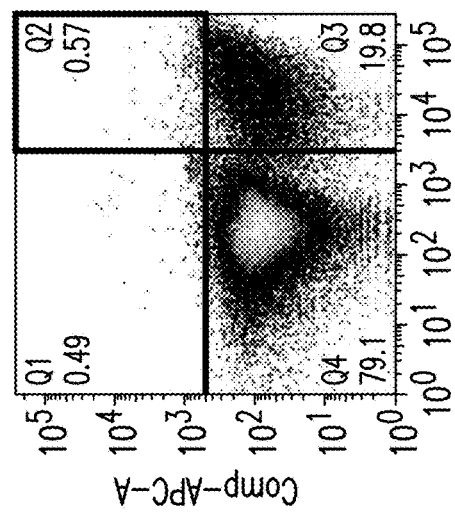
Figure 7A:
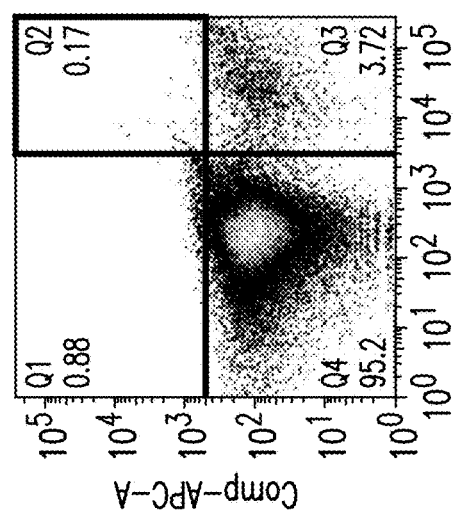

FIGS. 7A-7C. Amounts of L1CAM+ cells in (A) normal colon; (B) primary colorectal tumor and (C) liver metastasis.

Figure 8A:
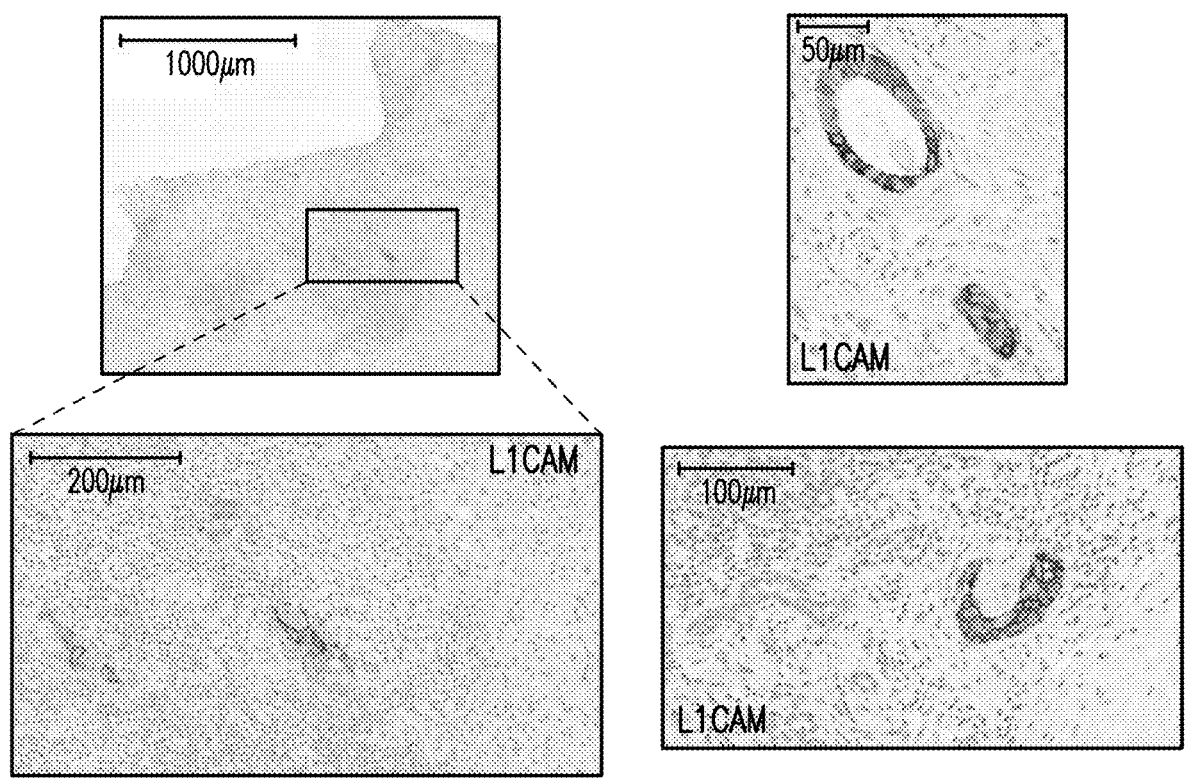
Figure 8B:
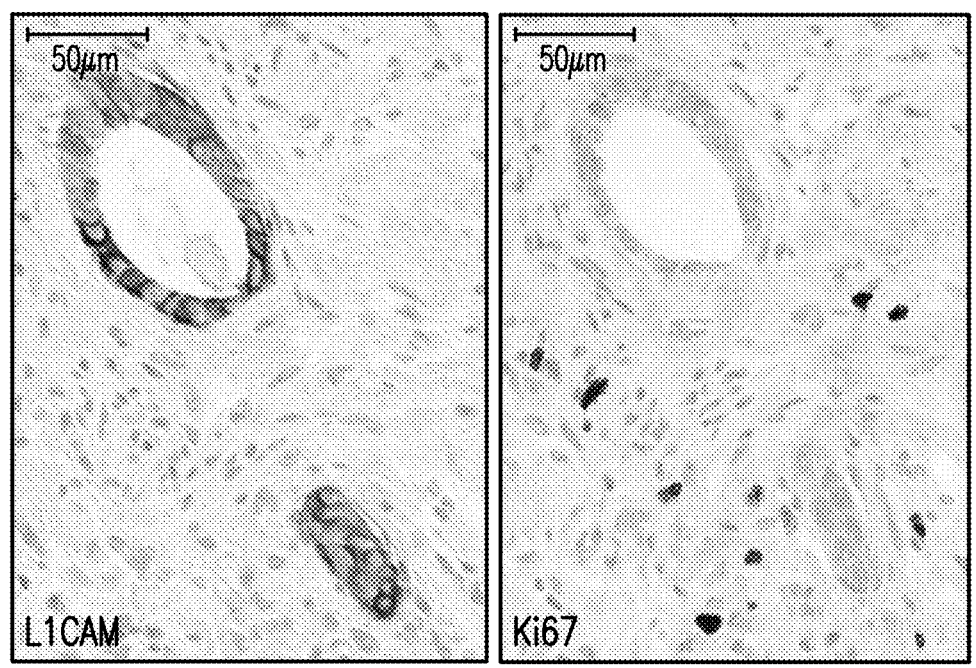

FIGS. 8A and 8B. L1CAM expression in post-chemotherapy residual disease. (A) Post-chemotherapy residual disease is strongly L1CAM+; (B) L1CAM+ cells are quiescent (comparative low KI67 expression).

FIGS. 9A-9D. Expression of L1CAM in tumor (A) pre-chemotherapy; (B) post-chemotherapy (after neo-adjuvant chemotherapy); and (C) graphical comparison of (A) and (B). (D) Relationship between number of organoids formed and L1CAM expression.

Figure 10:
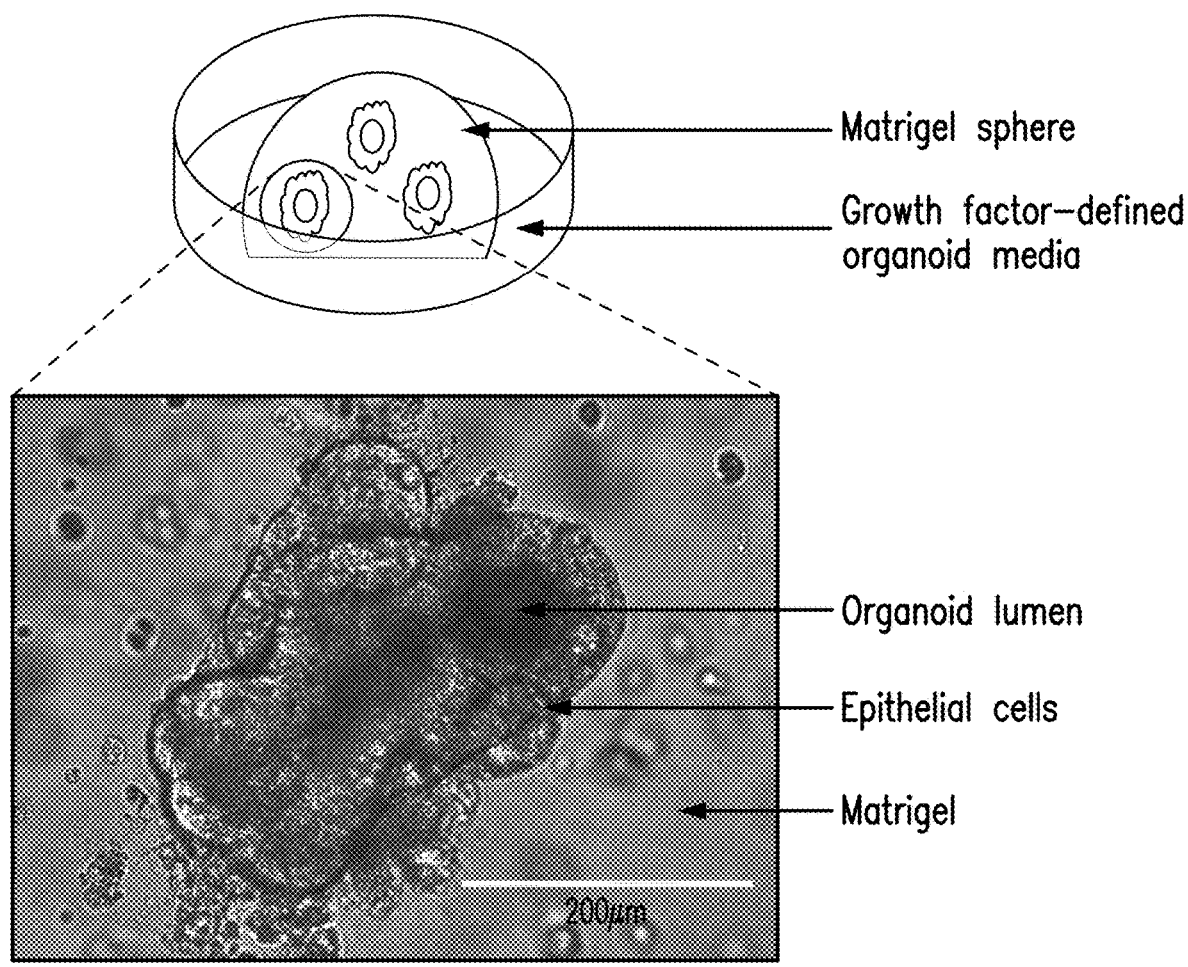

FIG. 10. Schematic showing general organoid culture.

Figure 11:
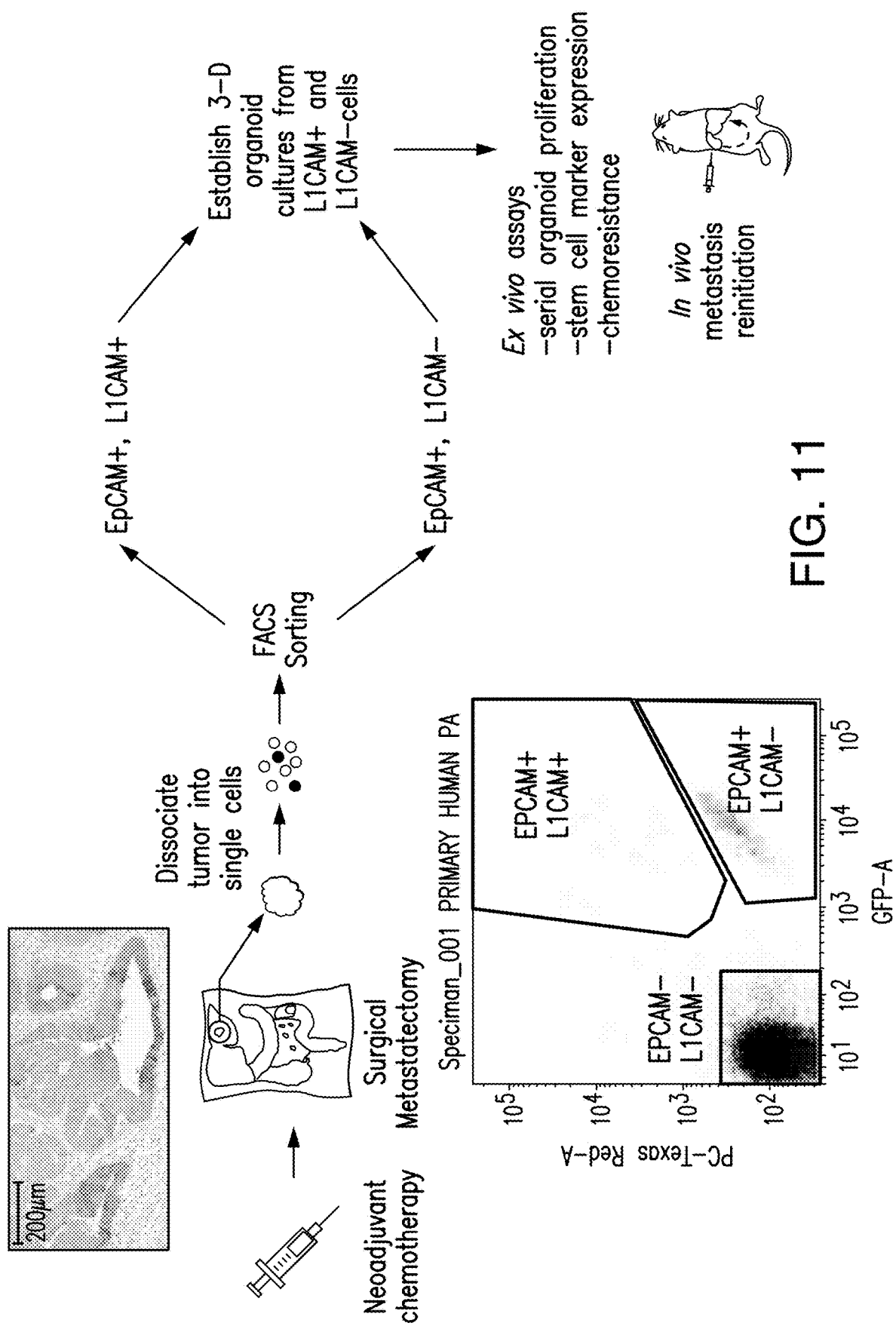

FIG. 11. Schematic showing obtention of metastatic cells from patient and selection of EpCAM+, L1CAM+ cells for organoid culture.

Figure 12:
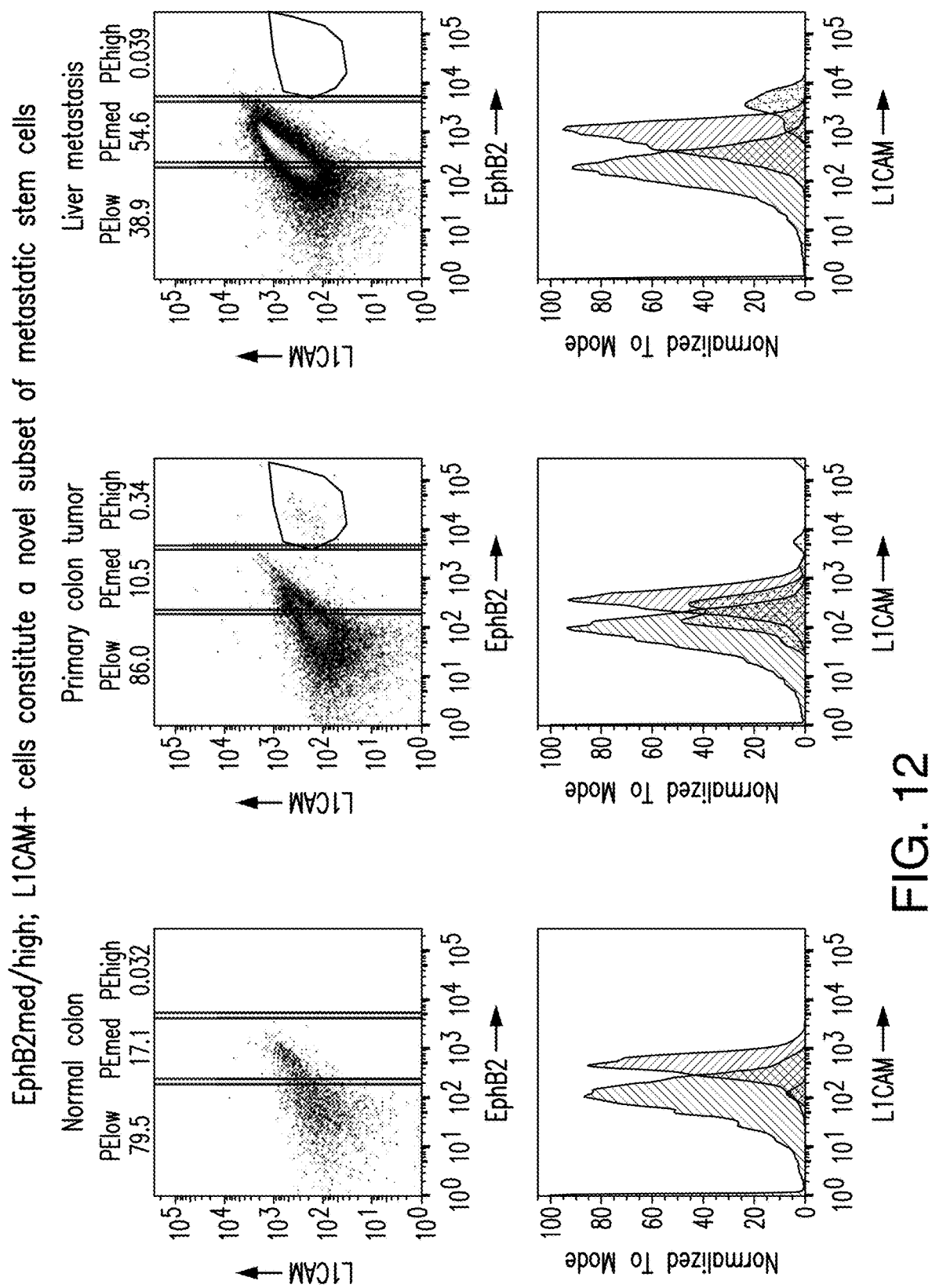

FIG. 12. FACS results sorting for EphB22med/high and L1CAM+ cells.

Figure 13:
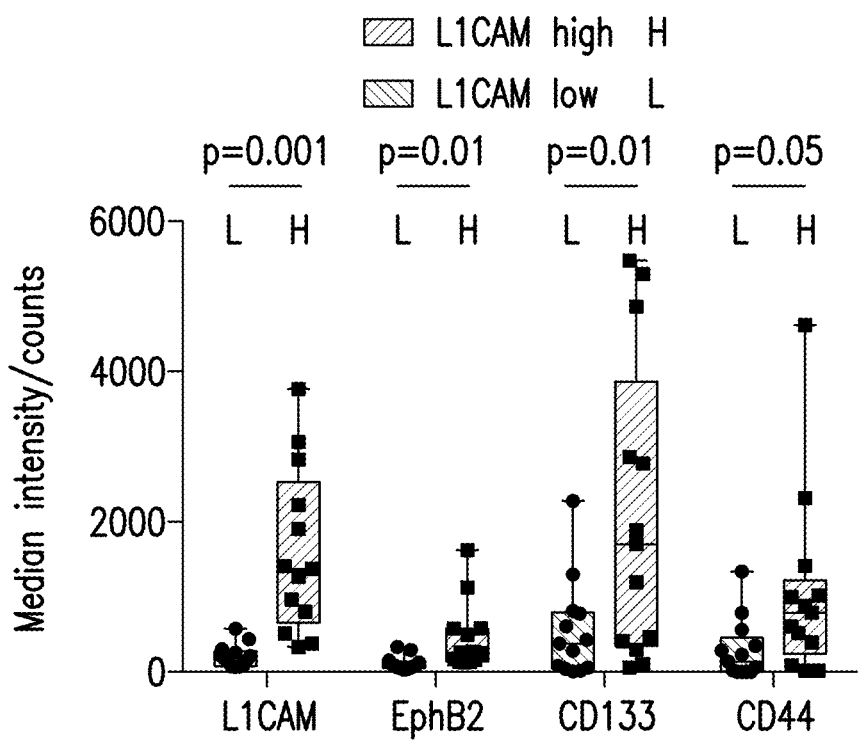

FIG. 13. Co-expression of EphB22, CD133 and CD44 markers on L1CAM high and low-expressing cells.

Figure 14:
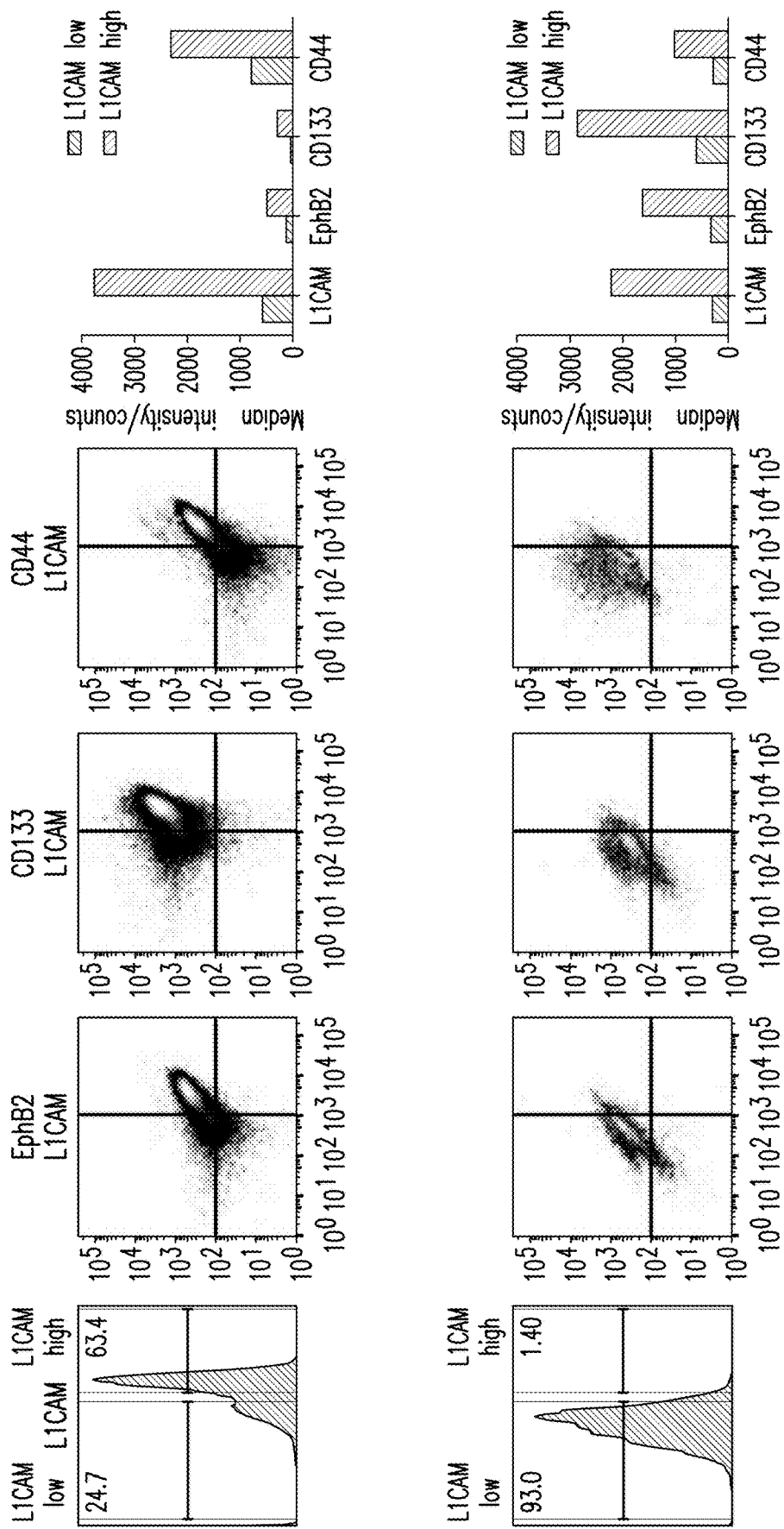
Figure 14:
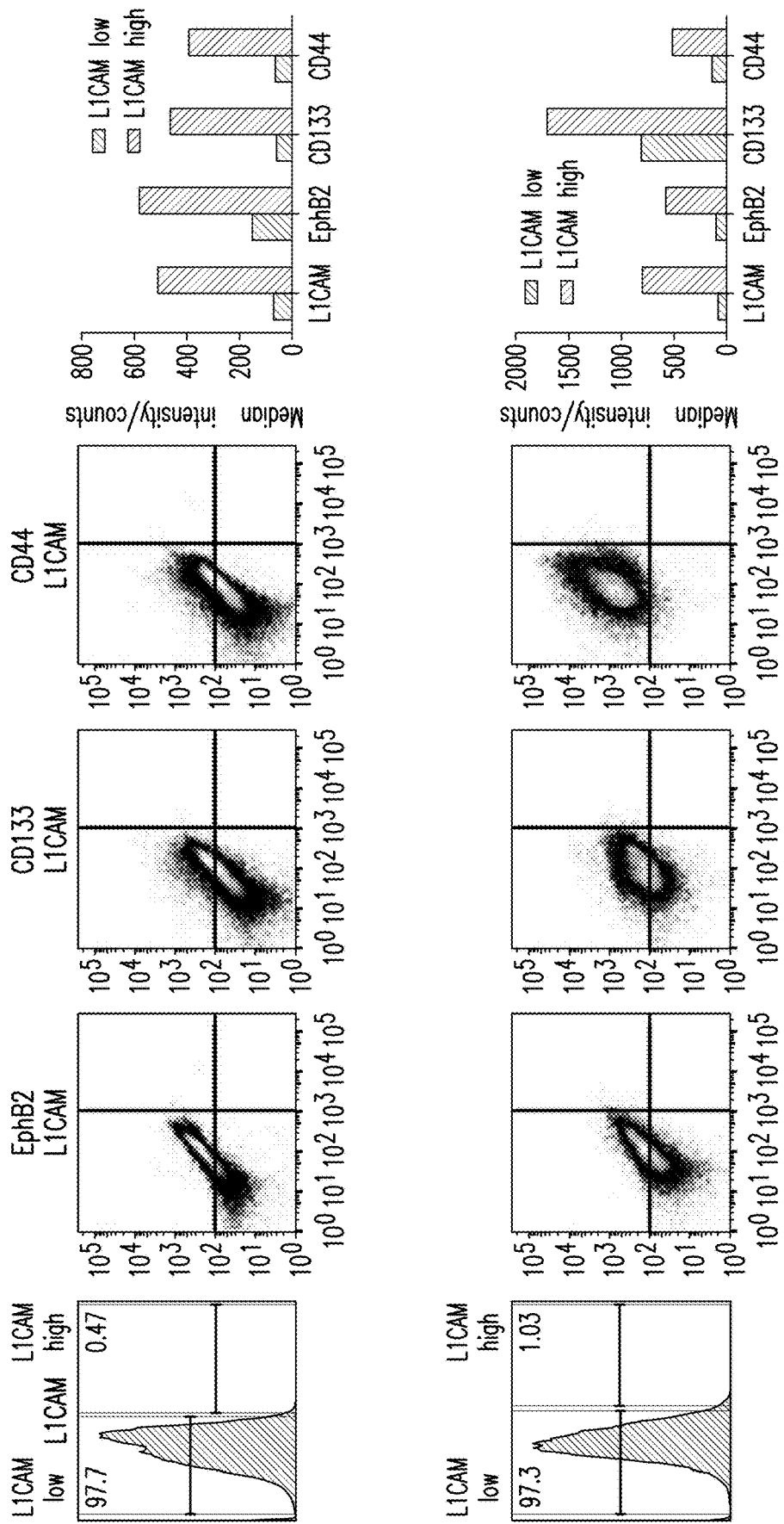
Figure 14:
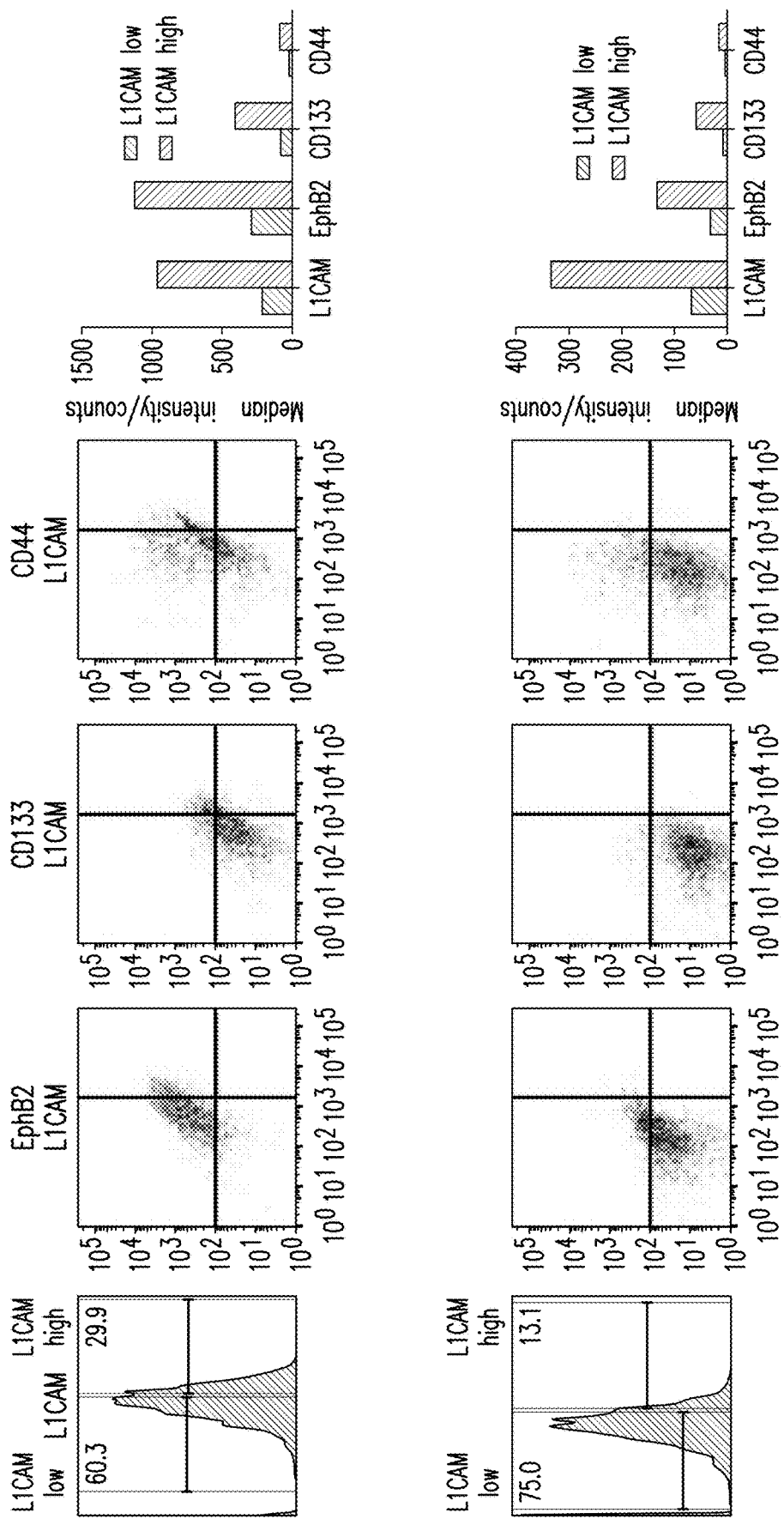
Figure 14:
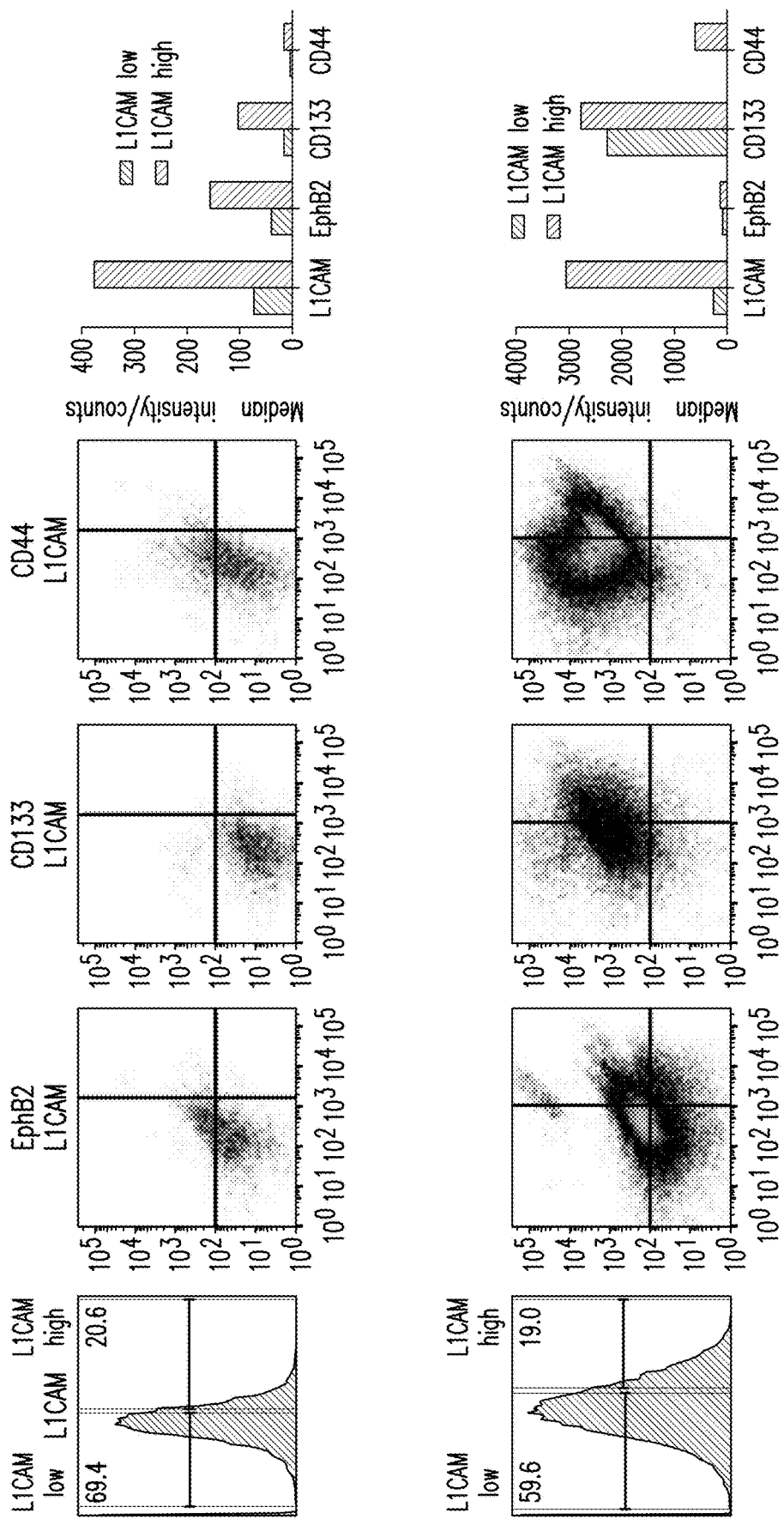
Figure 14:
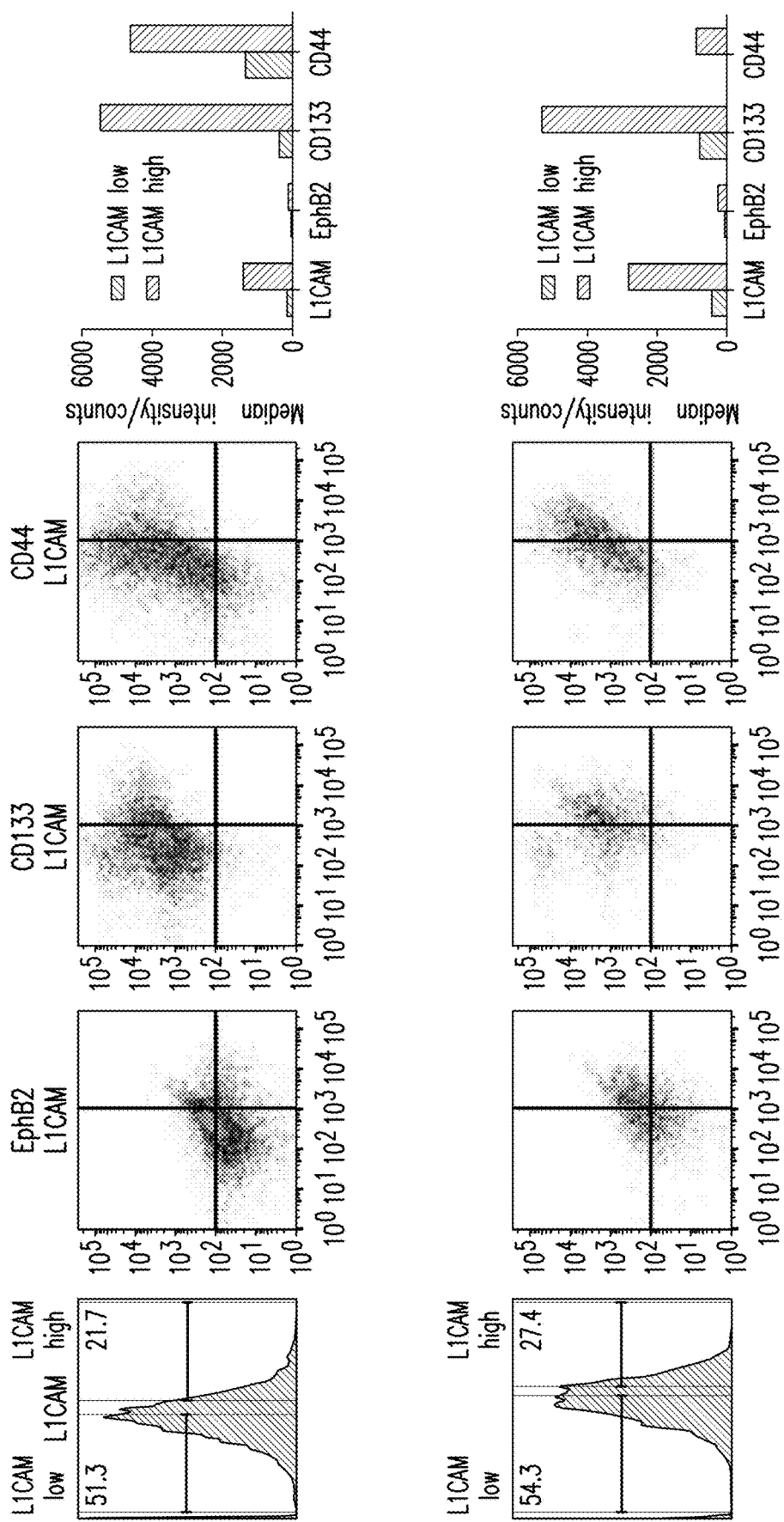
Figure 14:
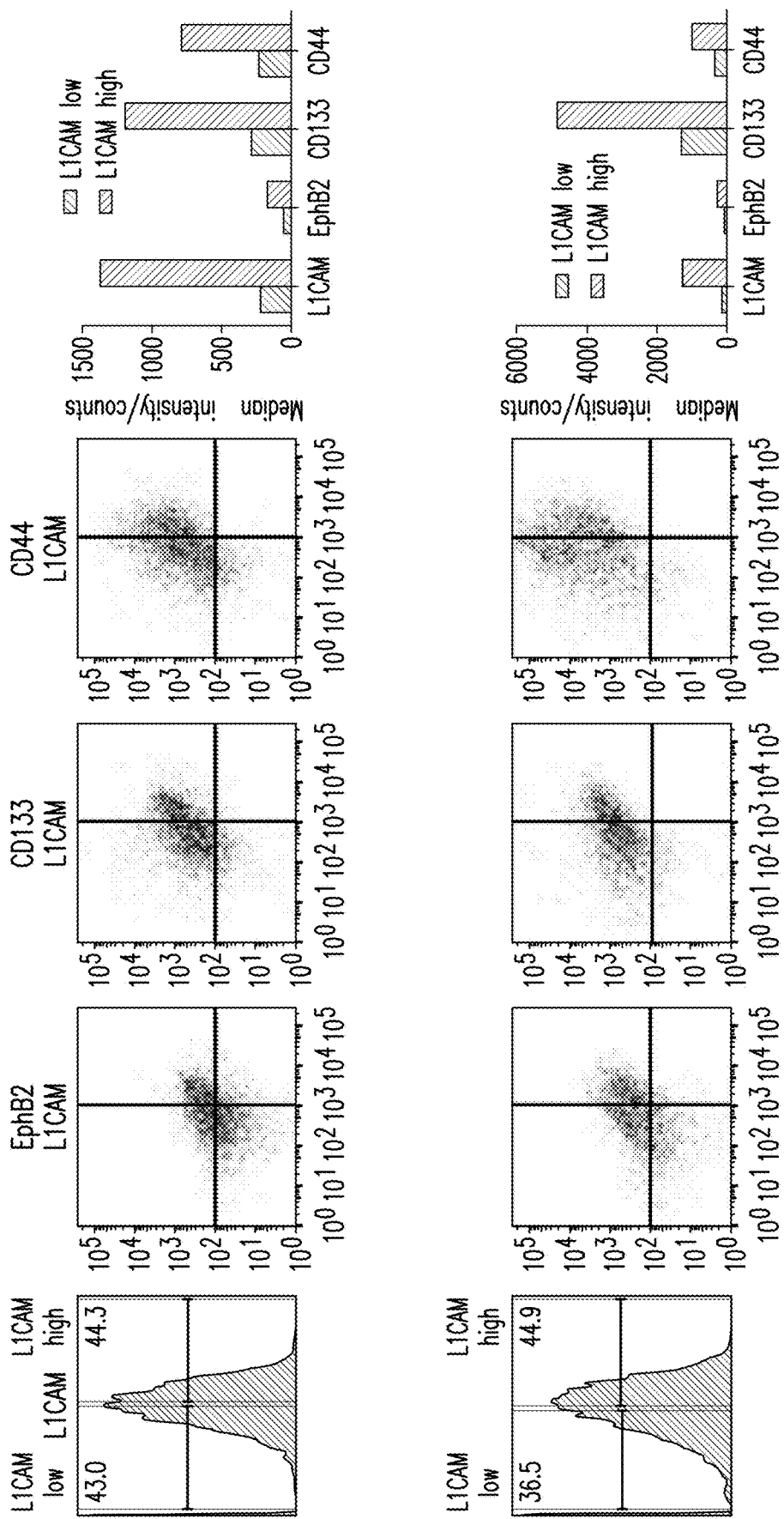
Figure 14:
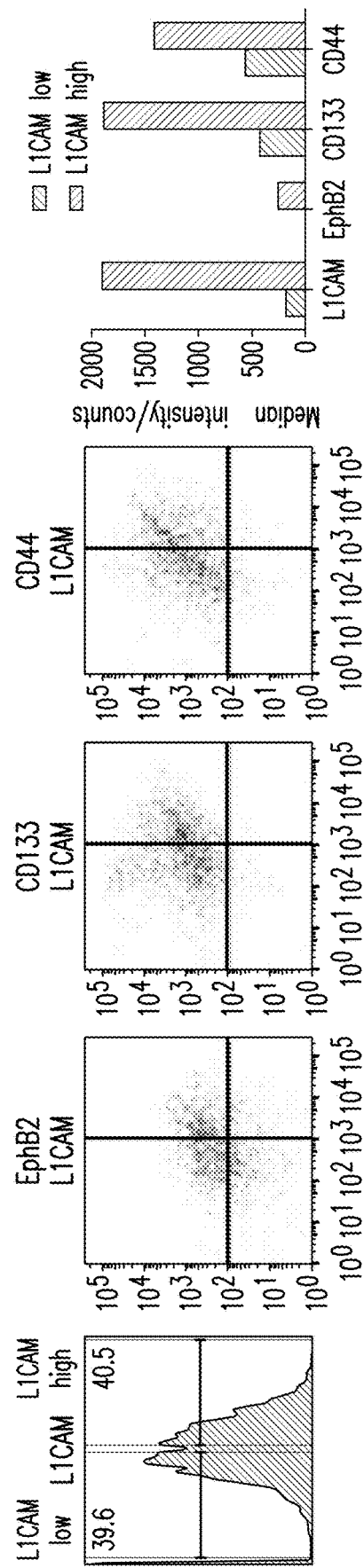

FIG. 14. FACS analysis for L1CAM, EphB22, CD133 and CD44.

Figure 15:
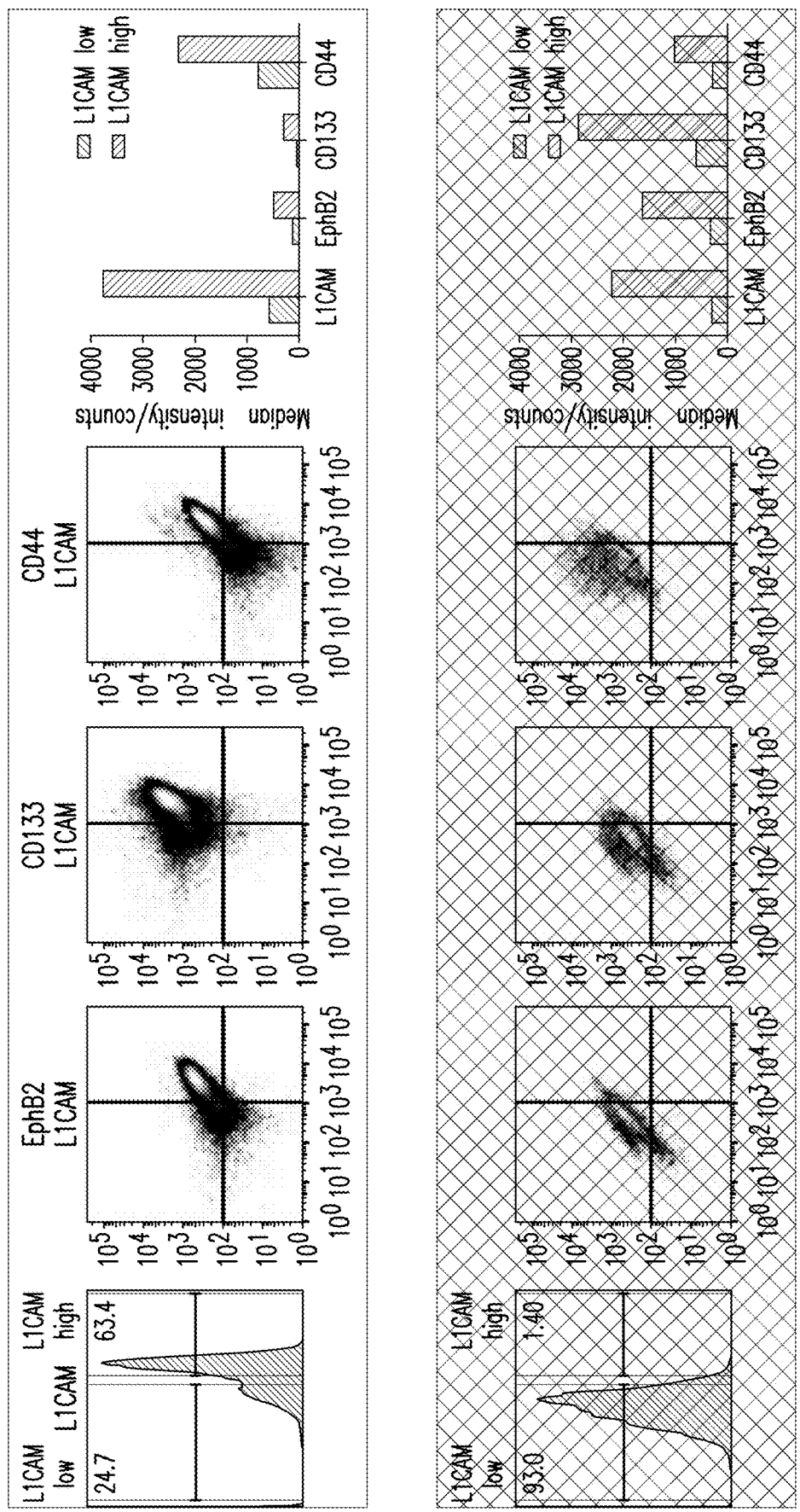
Figure 15:
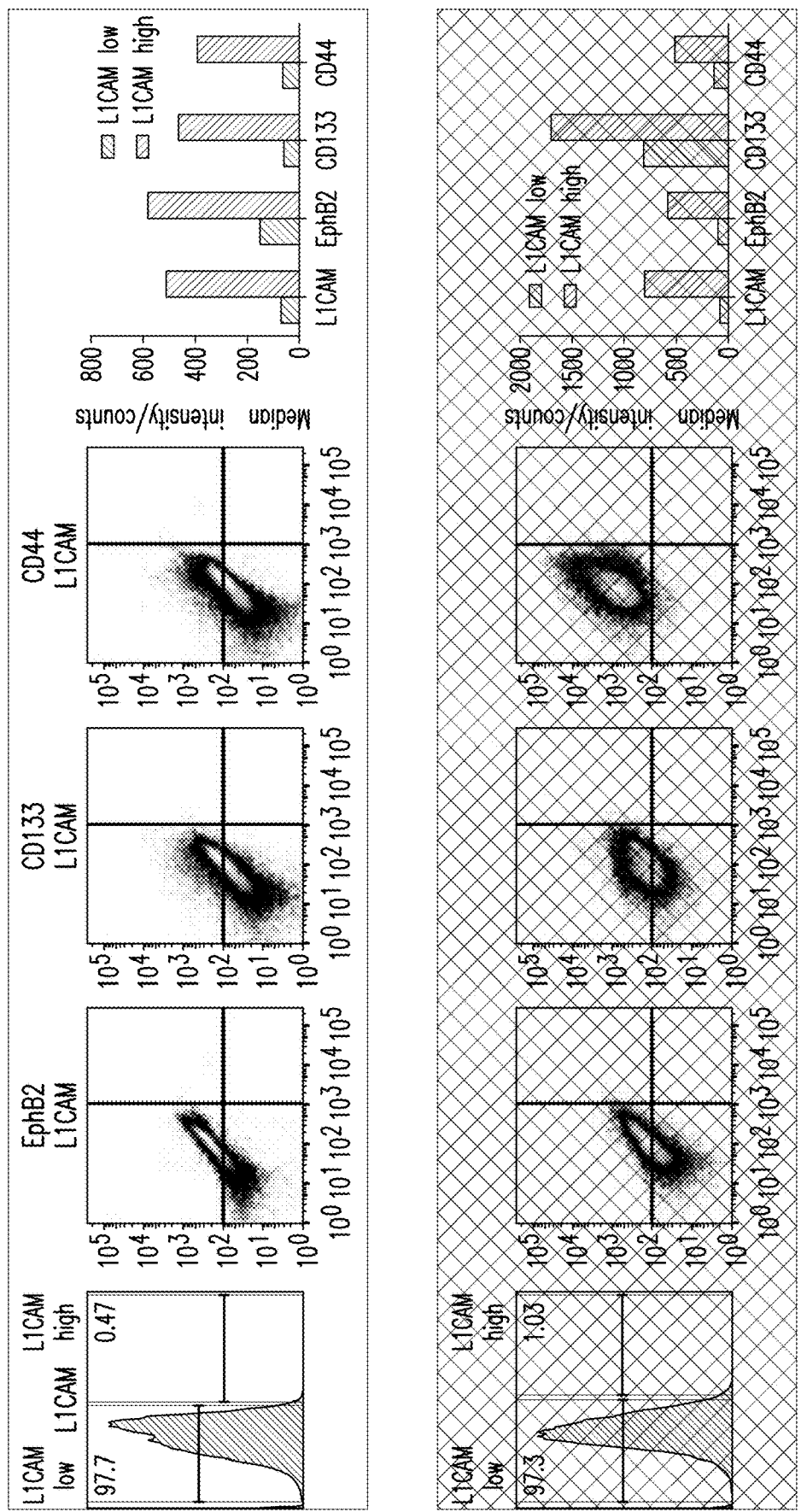
Figure 15:
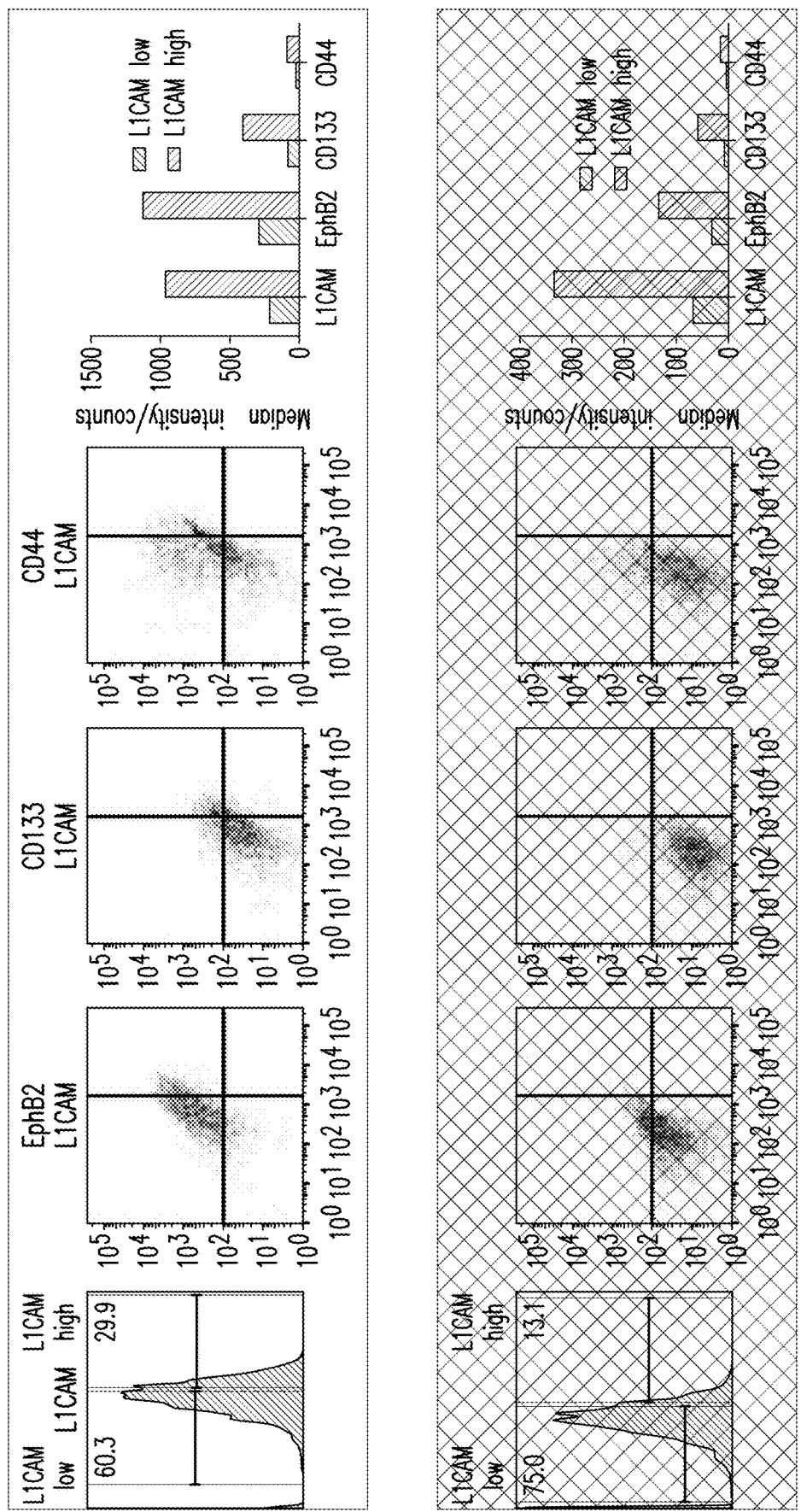
Figure 15:
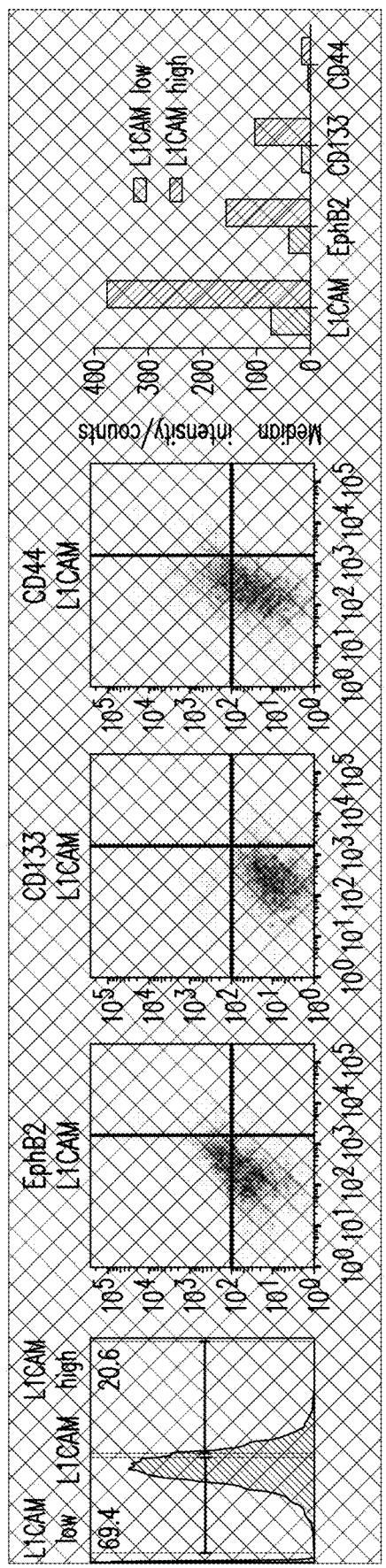
Figure 15:
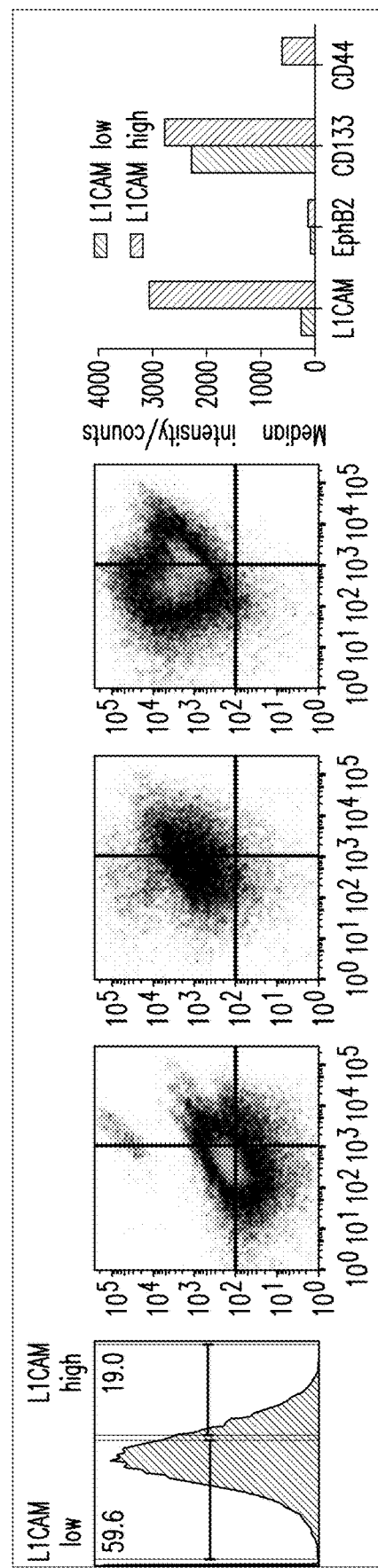
Figure 15:
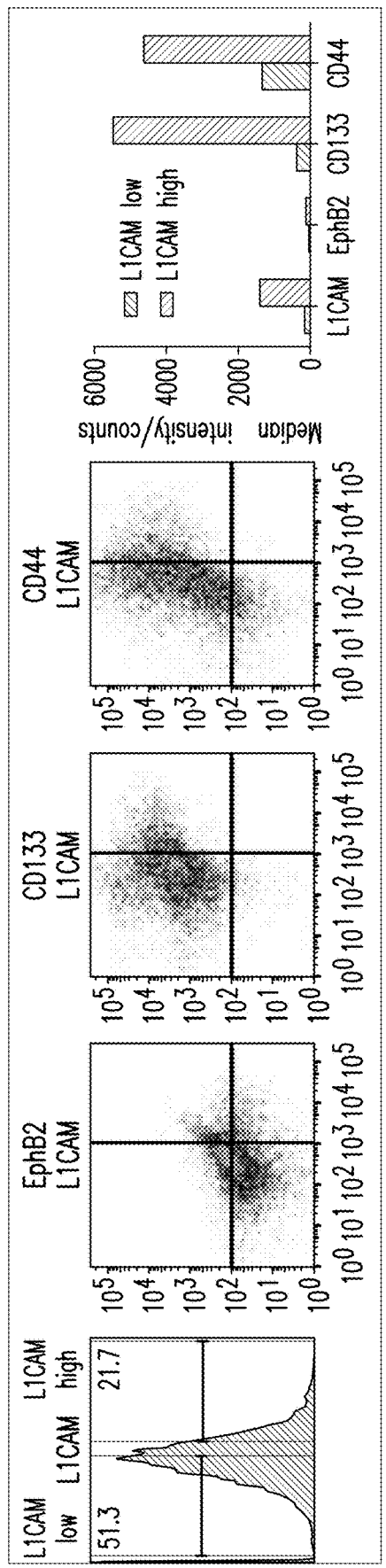
Figure 15:
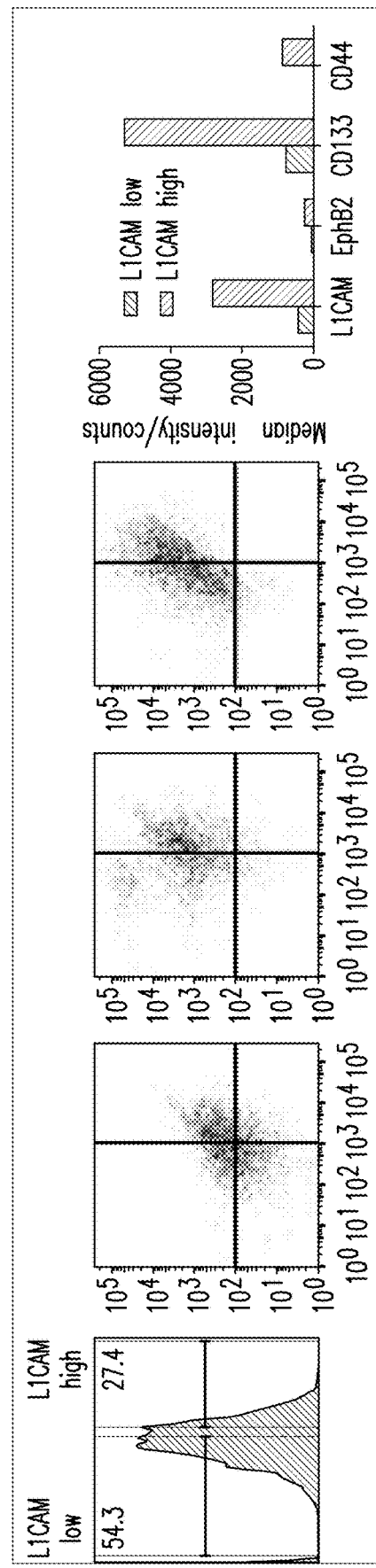
Figure 15:
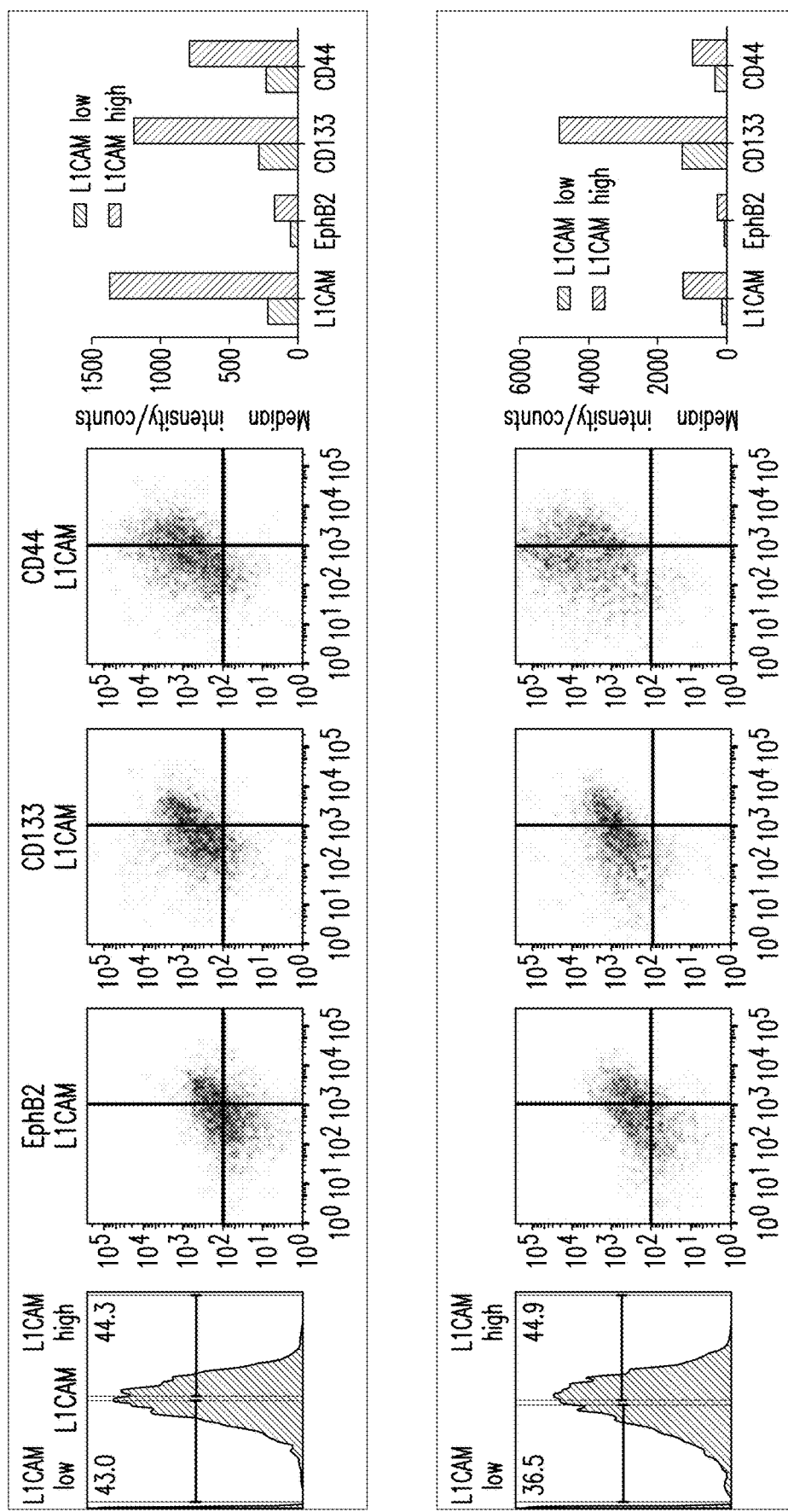
Figure 15:
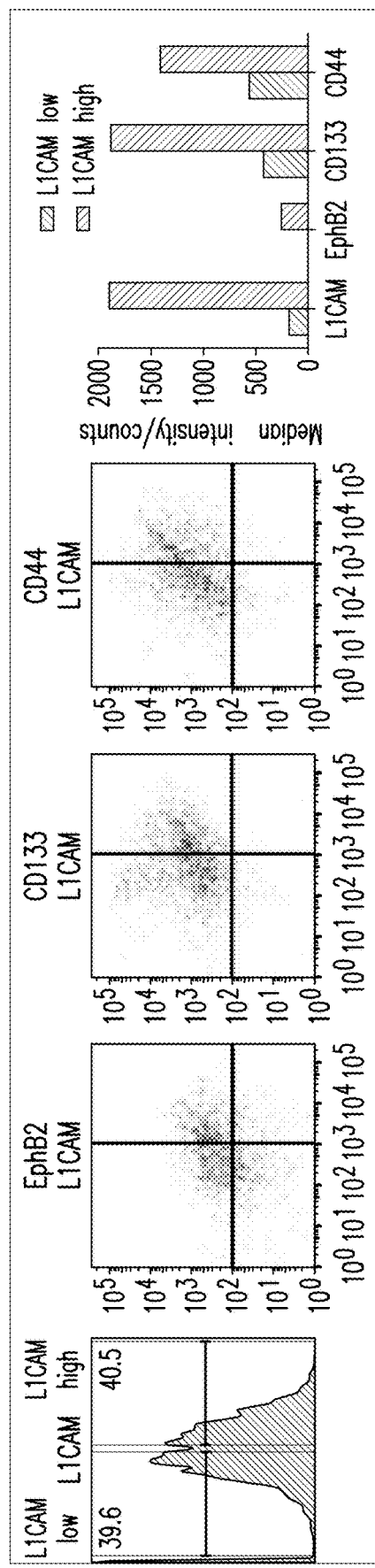

FIG. 15. FACS analysis for L1CAM, EphB22, CD133 and CD44.

Figure 16:
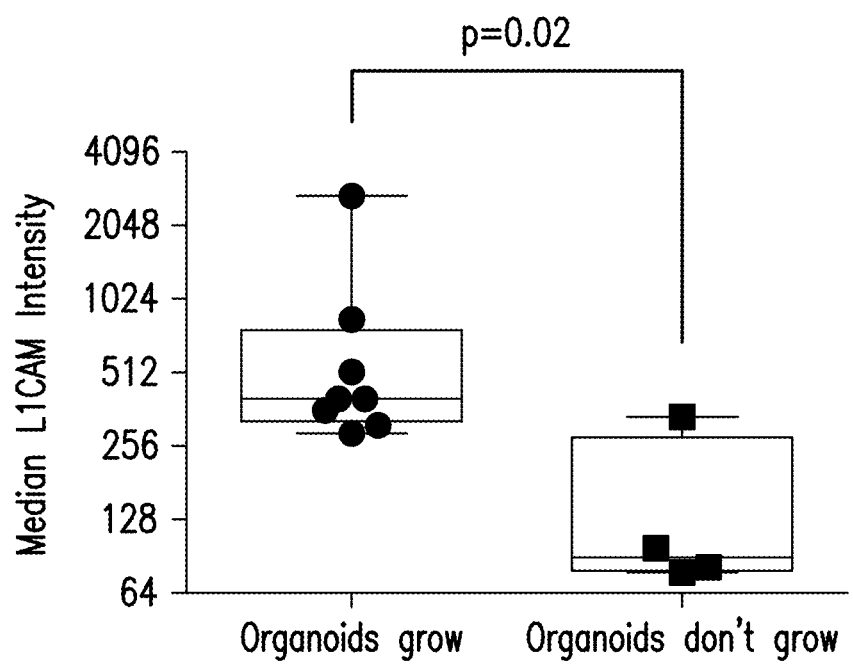

FIG. 16. Relationship between L1CAM expression and organoid growth.

Figure 17:
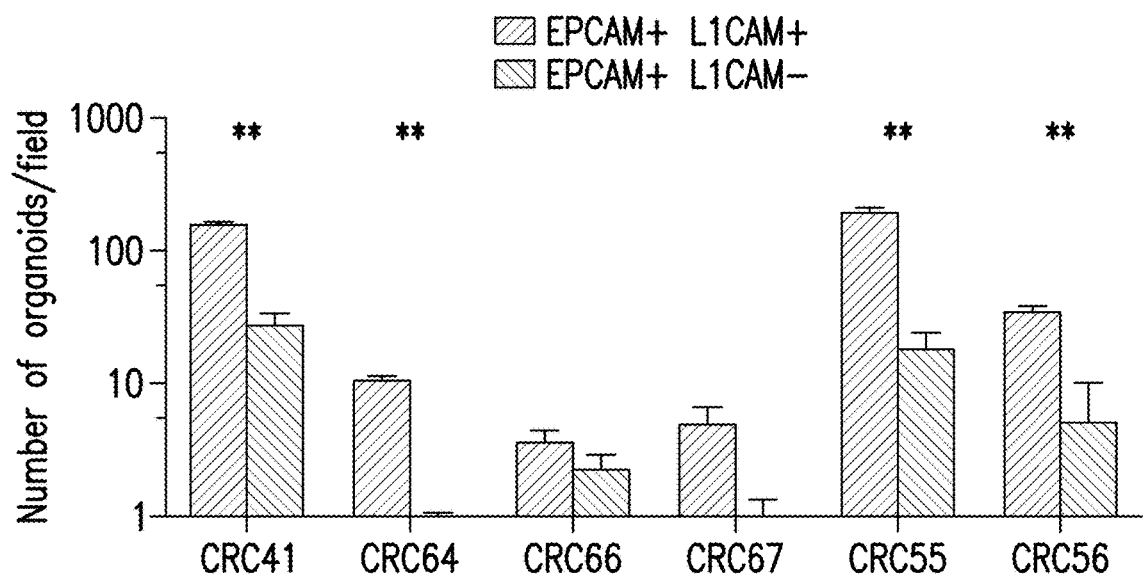

FIG. 17. For particular tumor samples, relationship between L1CAM expression and organoid formation.

Figure 18:
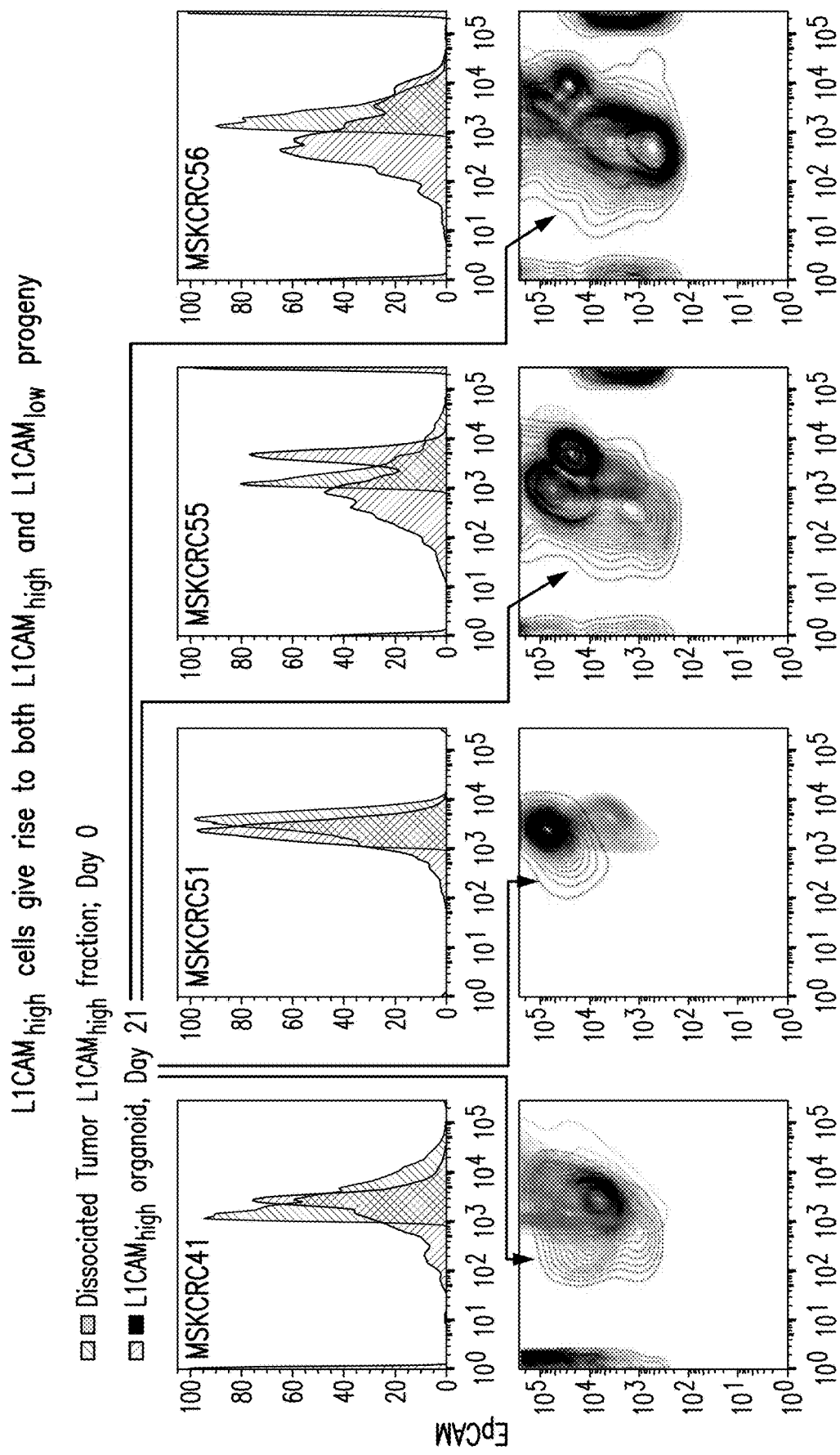

FIG. 18. L1CAM expression by L1CAM$^{high}$ cells in organoid culture.

Figure 19:
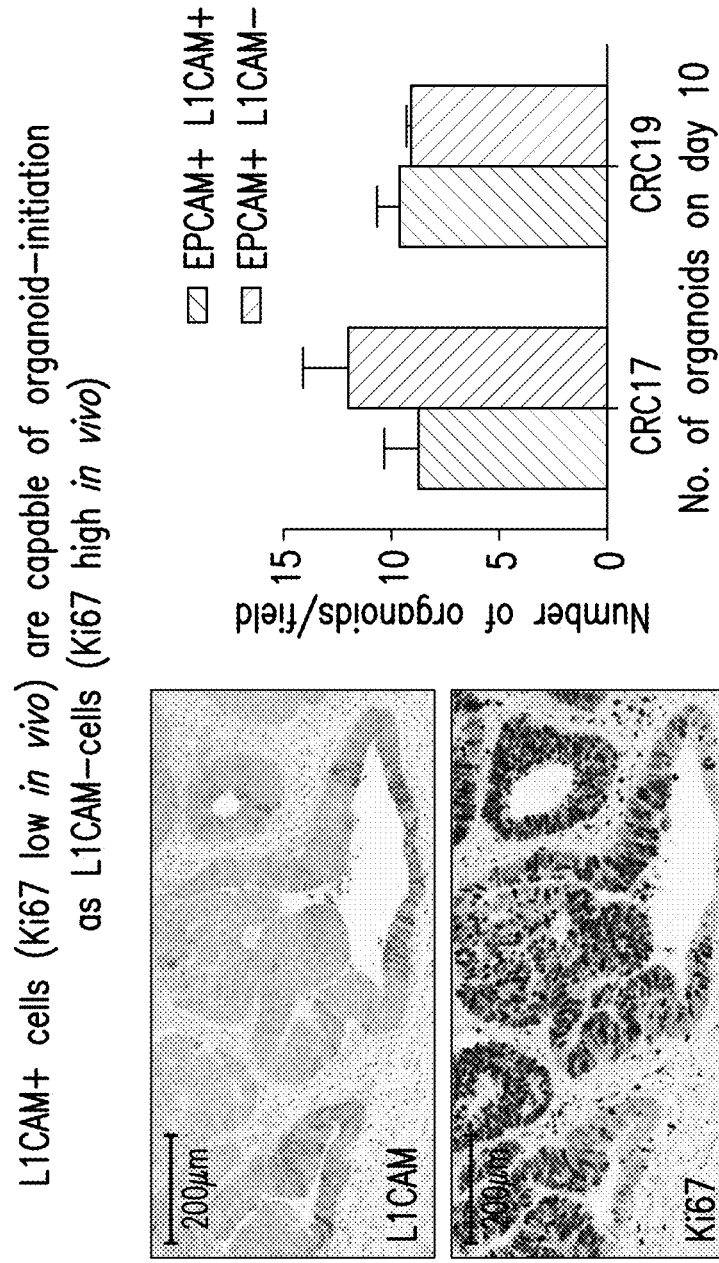

FIG. 19. Capability of change in L1CAM status during organoid culture in vivo.

Figure 20A:
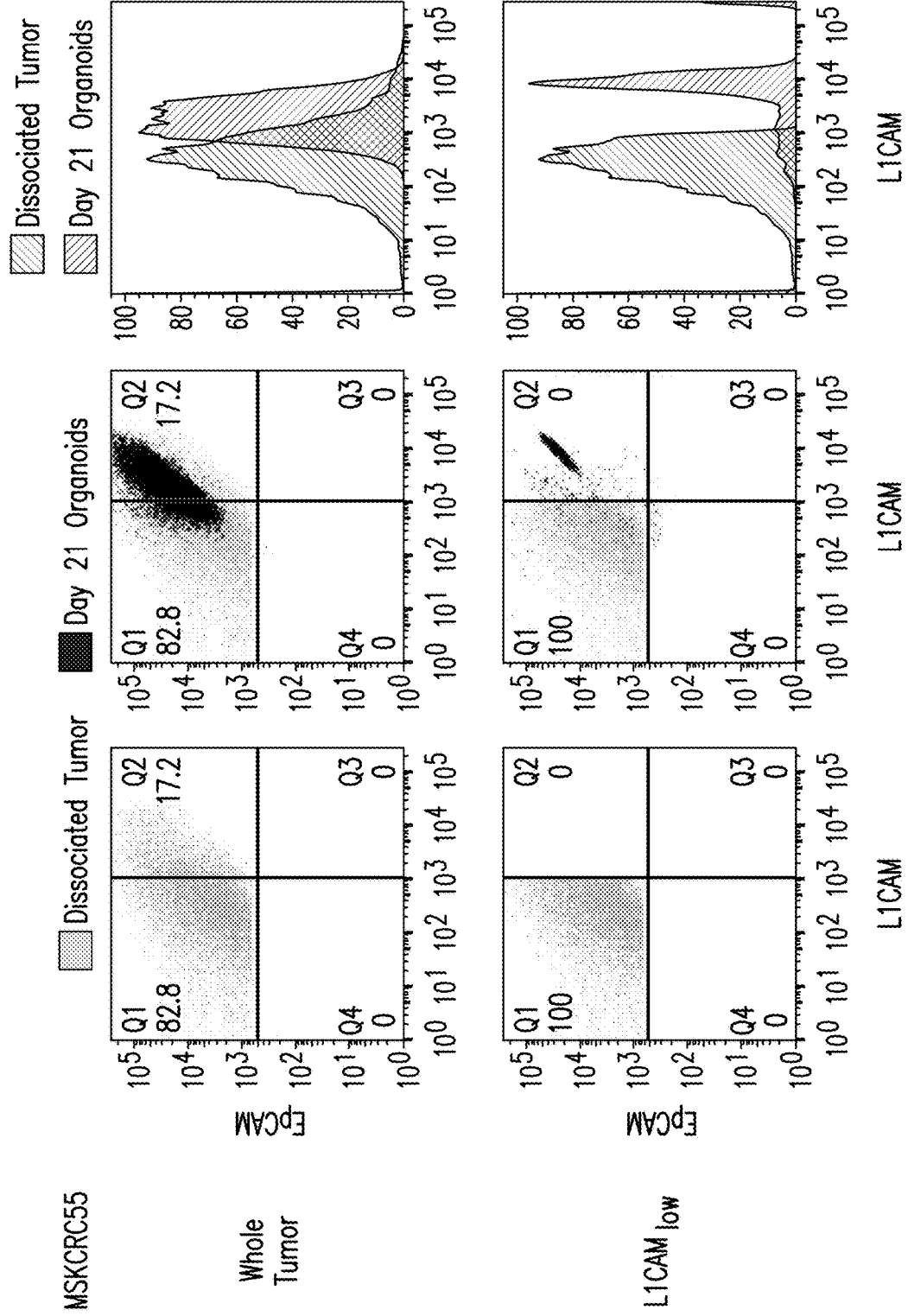
Figure 20B:
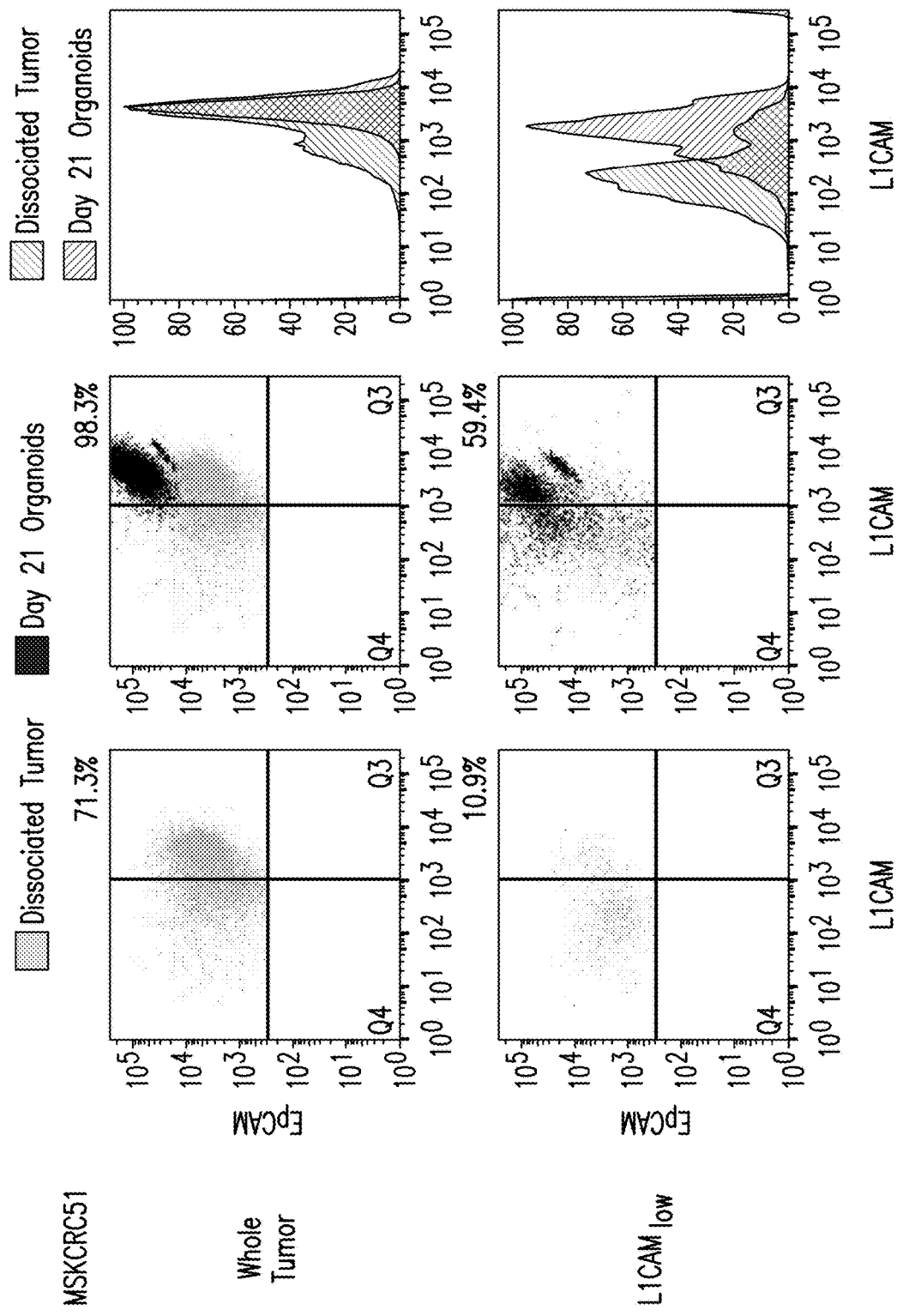

FIGS. 20A and 20B. L1CAM-expression is a trait selected for during organoid generation (A) patient MSKCRC55; (B) patient MSKCRC51.

Figure 21:
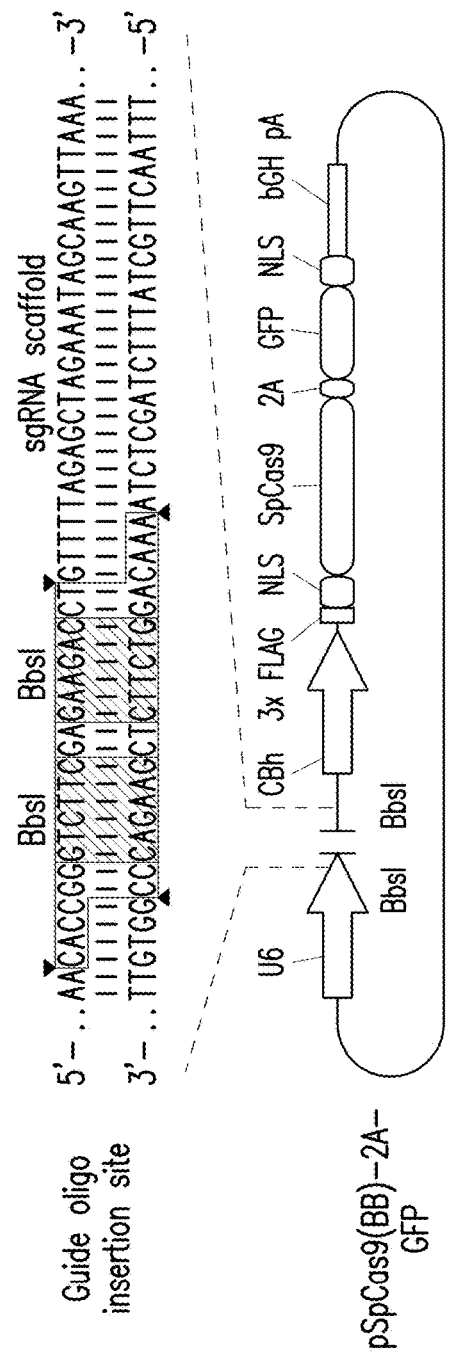
Figure 21:
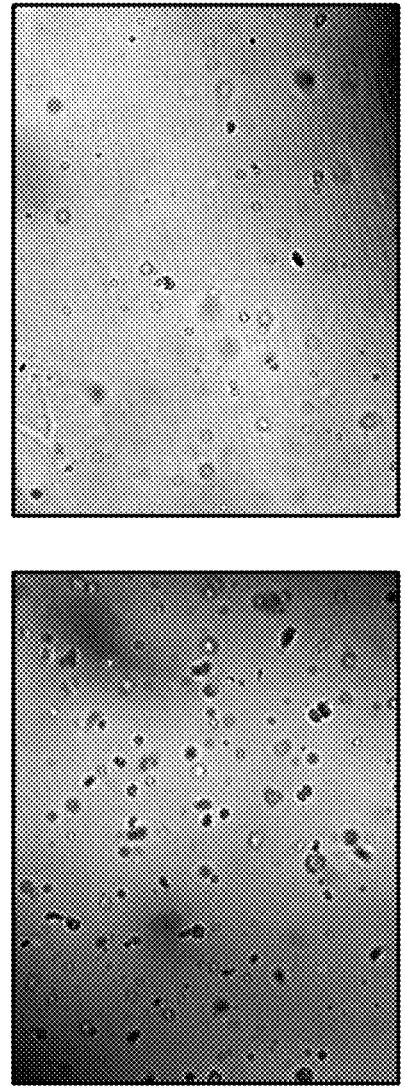

FIG. 21. Organoid formation following L1CAM deletion.

Figure 22:
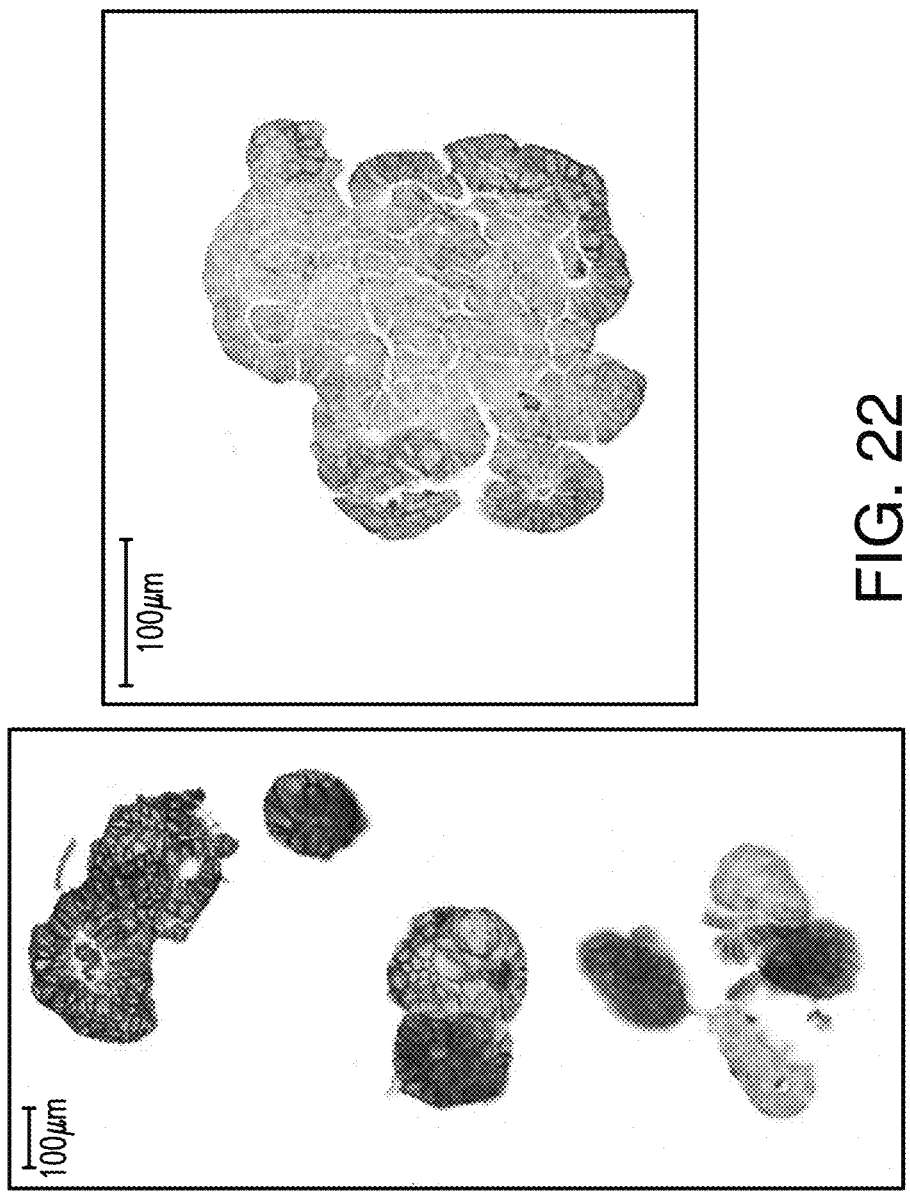

FIG. 22. L1CAM expression as a function of organoid size.

Figure 23:
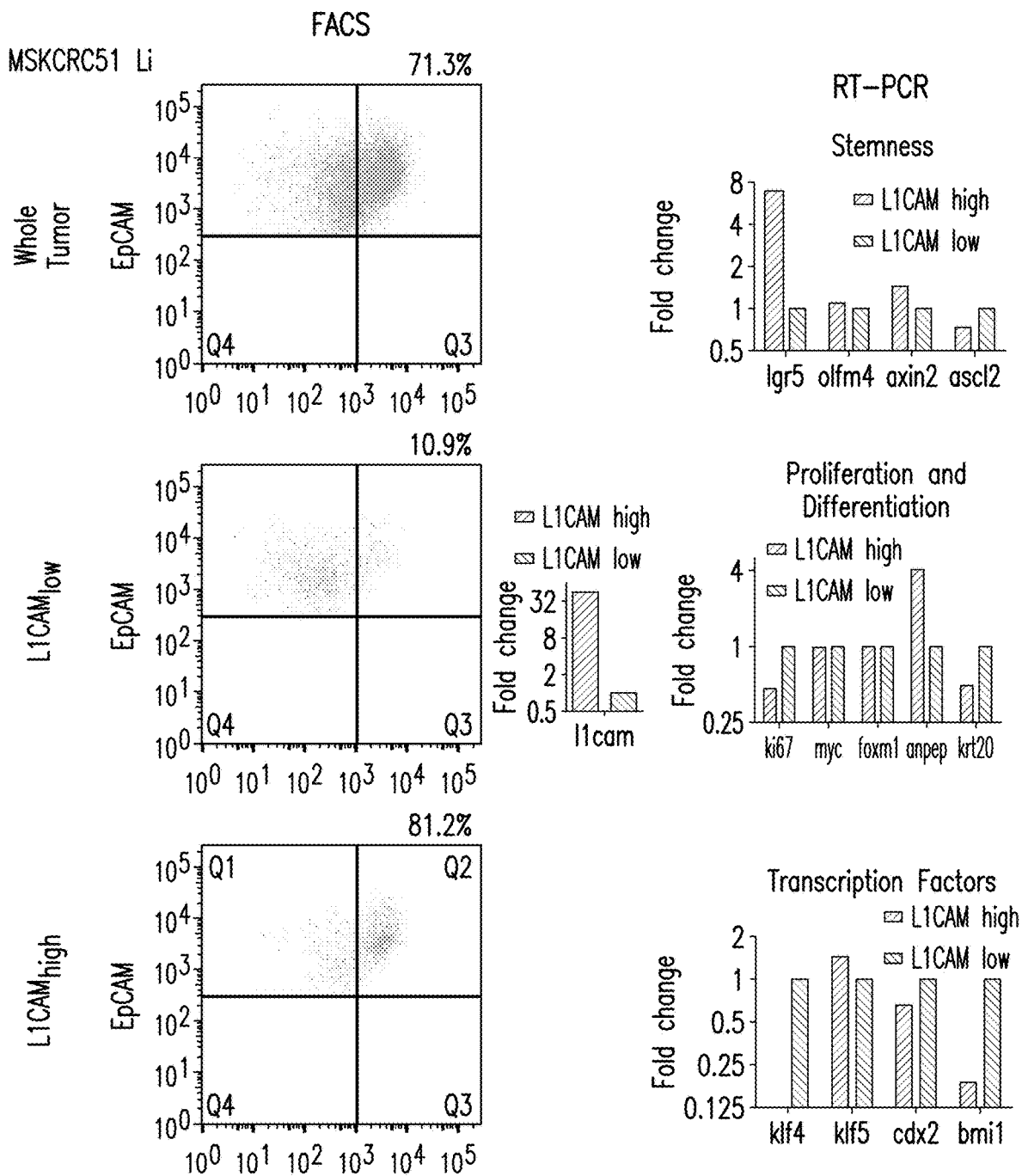

FIG. 23. Nascent small organoids are comprised of universally L1CAM+ cells, but as the organoids grow, the cells divide to generate mostly L1CAM-differentiated progeny that populate the bulk of the organoid FIG. 24. Inducible L1CAM knockdown reverses chemoresistance of Kras-mutant lung cancer cells.

Figure 25A:
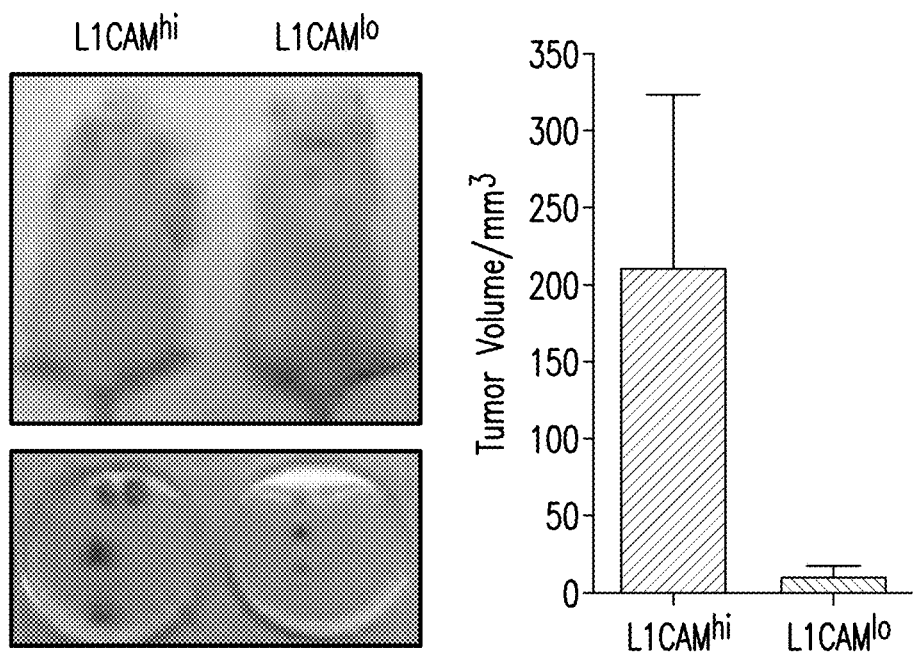
Figure 25B:
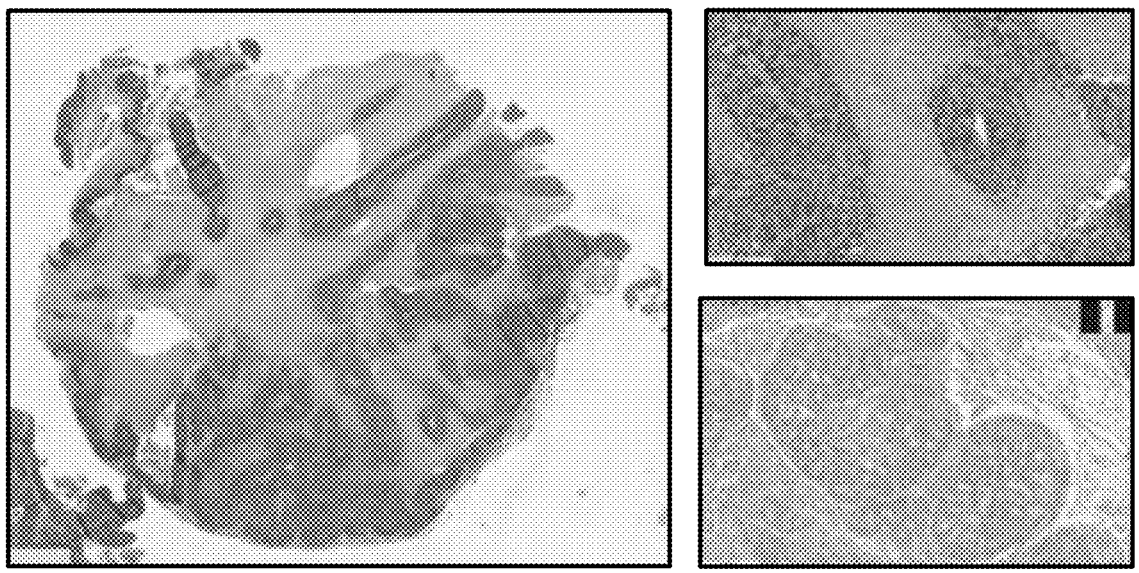
Figure 25C:
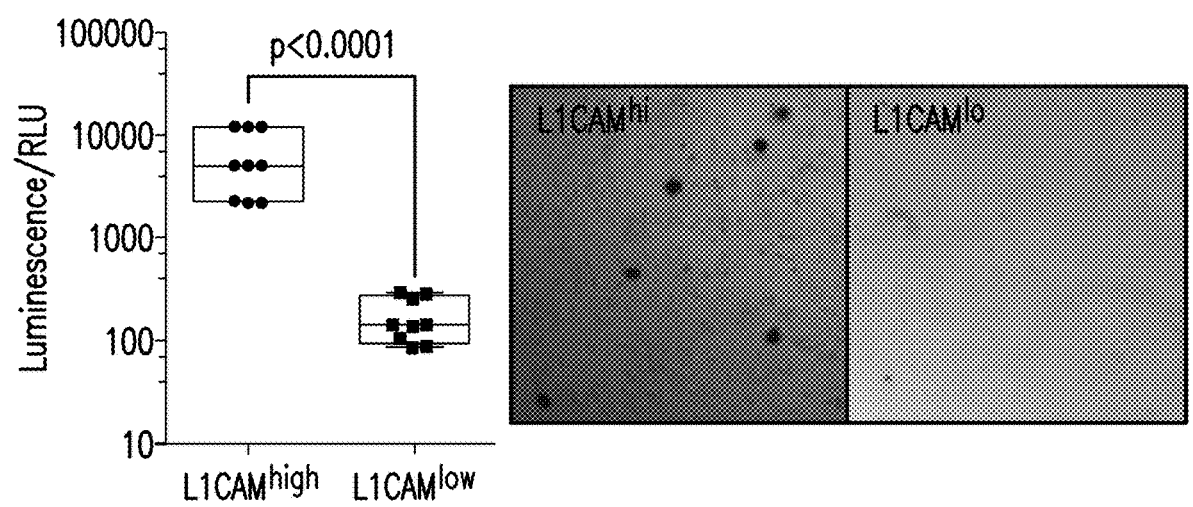
Figure 26A:
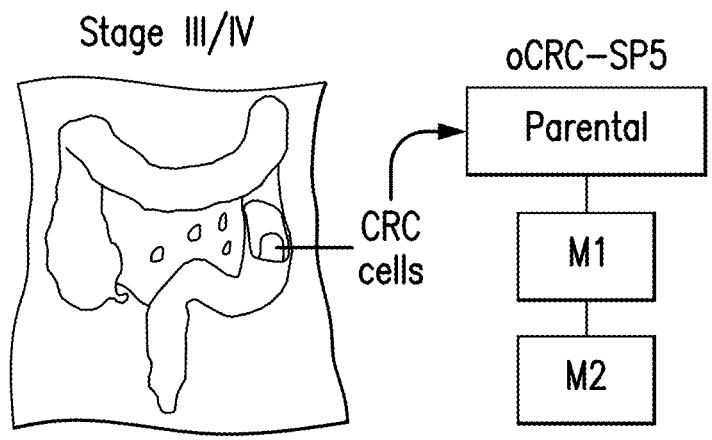
Figure 26B:
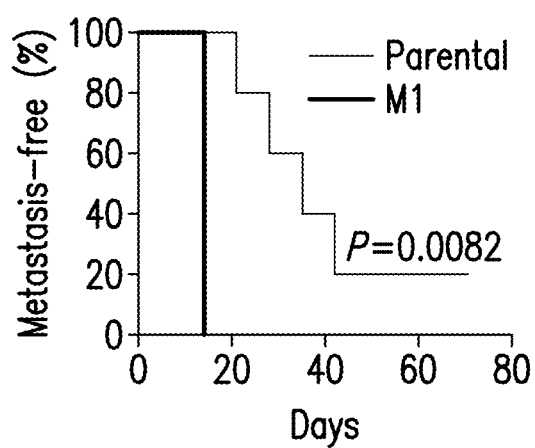
Figure 26C:
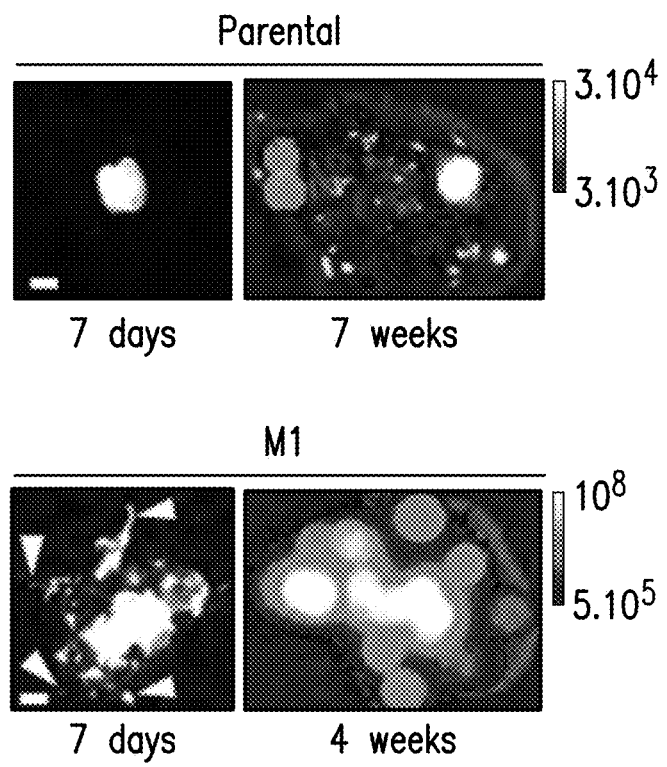
Figure 26D:
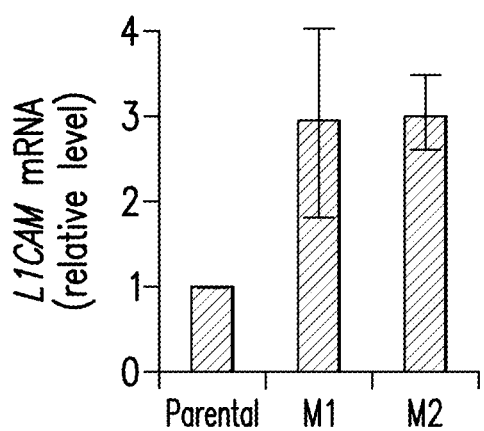

FIGS. 25A-25C. (A) Tumor re-initiation by L1CAM$^{high}$ versus L1CAMW cells in NSG mice. (B) Histology of tumors formed. (C) Organoid formation by L1CAM$^{high}$ versus L1CAMW tumor cells.

FIGS. 26A-26D. (A) Schematic of procedure to produce serial generations of metastatic cells. (B) Metastasis-free survival of mice inoculated with parental (light gray) or M1 generation (dark gray) cells. (C) Macroscopic images showing relative numbers of metastases resulting from Parental Cells at 7 days and 7 weeks (top panels) and of M1 generation cells at 7 days and 4 weeks. (D) Levels of L1CAM mRNA in Parental, M1, and M2 cells.

Figure 27:
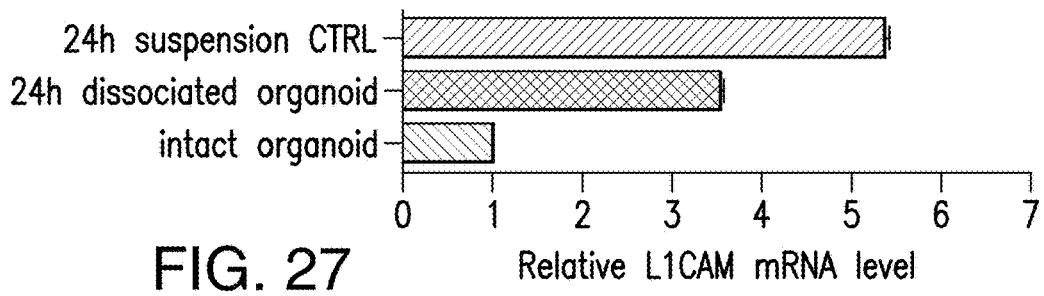

FIG. 27. Relative L1CAM expression in intact organoid, 24 hour-dissociated organoid, and 24 hr-suspension culture (control).

FIGS. 28A-28M. (A) Percent median L1CAM expression after CRISPR-Cas9 mediated L1CAM knockout. (B) Number of organoids per 2000 cells after CRISPR-Cas9 mediated L1CAM knockout. (C) Relative luminescence after CRISPR-Cas9 mediated L1CAM knockout. (D) Fluorescence microscopy showing organoids generated per 2000 cells from after CRISPR-Cas9 mediated L1CAM knockout. (E) Luminescence days after doxycycline-mediated knockdown of L1CAM. (F) Relative luminescence with or without doxycycline-induced L1CAM knockdown. (G) Fluorescence microscopy showing organoids with or without doxycycline-induced L1CAM knockdown (H) Luminescence, where doxycycline was withdrawn after 14 days. (I) Similar experiment as (H), with an independent L1CAM-targeting shRNA. (J) Caspase activity after dissociation, with or without doxycycline-induced L1CAM knockdown. (K) Tumor regrowth with or without doxycycline-induced L1CAM knockdown. (L) Average radiance of tumor regrowth after 3 weeks, with or without doxycycline-induced L1CAM knockdown. (M) Relative differences in levels of L1CAM and YAP target genes in intact organoids (left-most bar of pairs) versus dissociated cells.

FIGS. 29A-29F. (A) L1CAM expression in human normal colon, dissociated crypts, and d14 organoids (top panels, left to right) and in mouse normal colon and d14 organoids. Bar graphs show respective fold change in expression in crypts (left-most bar of pairs) versus organoids in three distinct humans or mice. (B) L1CAM expression (line marked with circles) over time in normal mouse colon organoids (relative to 1-Ki67 expression, line marked with squares). (C) Schematic and histology results showing L1CAM expression in mouse colon after epithelial injury. (D) Larger magnification showing L1CAM expression in regenerating transit-amplifying colon cells. (E) Consequence of L1CAM ablation on body weight and survival of mice sustaining colon epithelial injury. (F) Macroscopic and microscopic histology of results of (E).

FIGS. 30A-30F. (A) Relative L1CAM mRNA levels in intact organoids, dissociated organoid, or various cell suspensions. (B) Change in L1CAM levels in organoid or suspension cultures, with addition of various inflammatory mediators (represented by bars, left to right, corresponding top to bottom to the list in the key). (C) Effect of e-cadherin knockdown on expression of L1CAM, CDH1, CYR61 and ANKRD1. (D) Effect of REST knockdown on L1CAM expression. (E) CHIP-PCR results for binding of REST to first intron of the L1CAM locus. (F) Immunohistochemistry studies using antibodies directed toward L1CAM, e-cadherin and REST (p120-catenin) at primary CRC invasion fronts.

5. DETAILED DESCRIPTION OF THE INVENTION

For clarity of description, and not by way of limitation, the detailed description of the invention is divided into the following subsections:
(i) methods of treatment;
(ii) assay systems; and
(iii) kits.

5.1 Methods of Treatment

In various non-limiting embodiments, the present invention provides for a method of reducing the risk, in a subject who has received or is receiving treatment for a primary cancer, of metastatic spread of the primary cancer, comprising administering to the subject a therapeutic amount of a L1CAM inhibitor. In certain non-limiting embodiments, the L1CAM inhibitor is administered after one or more cycle of chemotherapy, targeted therapy, and/or immunotherapy of the primary cancer has been completed. In certain non-limiting embodiments, the L1CAM inhibitor is administered after a radiotherapy regimen of the primary cancer has been completed. In certain non-limiting embodiments, the L1CAM inhibitor is administered after an essentially complete (no cancer in the margins) surgical excision of the primary cancer or a metastasis has been completed. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after a cycle of treatment, or surgical excision, of the primary cancer. The period of time for maintenance therapy may be at least about three months or at least about 6 months or at least about one year or at least about 2 years. In certain non-limiting embodiments, the L1CAM inhibitor is administered after the subject has achieved remission of the primary cancer. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after achieving remission of the primary cancer. The period of time for maintenance therapy may be at least about three months or at least about 6 months or at least about one year or at least about 2 years.

In various non-limiting embodiments, the present invention provides for a method of inhibiting metastatic spread of a primary cancer in a subject who has received treatment for the primary cancer, comprising administering to the subject a therapeutic amount of a L1CAM inhibitor. In certain non-limiting embodiments, the L1CAM inhibitor is administered after one or more cycle of chemotherapy, targeted therapy, and/or immunotherapy of the primary cancer has been completed. In certain non-limiting embodiments, the L1CAM inhibitor is administered after a radiotherapy regimen of the primary cancer has been completed. In certain non-limiting embodiments, the L1CAM inhibitor is administered after an essentially complete (no cancer in the margins) surgical excision of the primary cancer or a metastasis has been completed. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after a cycle of treatment, or surgical excision, of the primary cancer. The period of time for maintenance therapy may be at least about three months or at least about 6 months or at least about one year or at least about 2 years. In certain non-limiting embodiments, the L1CAM inhibitor is administered after the subject has achieved remission of the primary cancer. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after achieving remission of the primary cancer. The period of time for maintenance therapy may be at least about three months or at least about 6 months or at least about one year or at least about 2 years.

In various non-limiting embodiments, the present invention provides for a method of inhibiting progression of metastatic disease in a subject comprising administering to the subject a therapeutic amount of a L1CAM inhibitor. In various non-limiting embodiments, the present invention provides for a method of inhibiting progression of metastatic disease in a subject who has received treatment for the primary cancer, comprising administering to the subject a therapeutic amount of a L1CAM inhibitor. In certain non-limiting embodiments, the L1CAM inhibitor is administered after one or more cycle of chemotherapy, targeted therapy, and/or immunotherapy of the primary cancer has been completed. In certain non-limiting embodiments, the L1CAM inhibitor is administered after a radiotherapy regimen of the primary cancer has been completed. In certain non-limiting embodiments, the L1CAM inhibitor is administered after an essentially complete (no cancer in the margins) surgical excision of the primary cancer or a metastasis has been completed. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after a cycle of treatment, or surgical excision, of the primary cancer. The period of time for maintenance therapy may be at least about three months or at least about 6 months or at least about one year or at least about 2 years. In certain non-limiting embodiments, the L1CAM inhibitor is administered after the subject has achieved remission of the primary cancer. In certain non-limiting embodiments, the L1CAM inhibitor is administered in a maintenance regimen (e.g., administered at regular intervals (e.g., at least once a week, at least once a month, at least once every two months, at least once every three months, at least once every six months)) for a period of time after achieving remission of the primary cancer. The period of time for maintenance therapy may be at least about three months or at least about 6 months or at least about one year or at least about 2 years.

In various non-limiting embodiments, the present invention provides for a method of inhibiting progression of metastatic disease in a subject comprising administering to the subject a therapeutic amount of an agent that reduces L1CAM expression in cancer cells, for example via CRISPR/Cas9 mediated gene editing.

A metastasis is a population of cancer cells at a location that is not physically contiguous with the original location of the cancer.

"Reducing the risk of metastatic spread" is relative to the risk of metastatic spread in a comparable control subject not treated with an L1CAM inhibitor.

"Inhibiting metastatic spread of a primary cancer" means one or more of: reducing the number, location(s), and/or size, of metastasis/es, and/or increasing the period of time to occurrence of metastasis/es, and/or prolonging survival, relative to a comparable control subject not treated with an L1CAM inhibitor.

"Inhibiting progression of metastatic disease" means one or more of the following: decreasing the size of existing metastasis/es, reducing the rate of growth of existing metastasis/es, reducing the incidence of newly detectable metastasis/es, improving quality of life, and/or increasing time to recurrence, and/or prolonging survival, relative to a comparable control subject not treated with an L1CAM inhibitor.

In certain non-limiting embodiments, the invention provides, in a subject having a primary cancer, a method of inhibiting metastatic spread of the cancer, comprising determining whether a cell of the cancer expresses L1CAM and, if the cell does express L1CAM, administering to the subject, in addition to therapy of the primary cancer, a therapeutic amount of a L1CAM inhibitor.

In non-limiting embodiments, a further indicator of increased risk is high/medium surface expression of EphB2.

In various non-limiting embodiments, the subject is a human or a non-human animal, for example a dog, a cat, a horse, a rodent, a mouse, a rat, a hamster, a non-human primate, a rabbit, a sheep, a cow, a cetacean, etc.

In various non-limiting embodiments, the cancer is a breast cancer, a lung cancer, a renal cancer, a colorectal cancer, an ovarian cancer, a prostate cancer, a liver cancer, or a melanoma.

The site of metastasis may be, for example but not by way of limitation, brain, lung, bone, or liver.

In various non-limiting embodiments of the invention, an L1CAM inhibitor may be administered concurrently with a chemotherapy and/or targeted therapy and/or immunotherapy and/or radiotherapy regimen. However, in alternative non-limiting embodiments, an L1CAM inhibitor may be administered after a course of chemotherapy, targeted therapy, immunotherapy and/or radiotherapy is complete. In specific, non-limiting examples, the L1CAM inhibitor may be administered at the conclusion of the treatment regimen, or at least one month thereafter, or at least three months thereafter, or at least six months thereafter, or at least one year thereafter. In related non-limiting embodiments, an L1CAM inhibitor may be administered after an essentially complete (no cancer in the margins) surgical excision of the primary cancer or metastasis has been completed.

In various non-limiting embodiments, an L1CAM inhibitor may be administered in a maintenance regimen (e.g., administered at regular intervals (e.g., at least once a week, at least once a month, at least once every two months, at least once every three months, at least once every six months) for a period of time after a course of chemotherapy or radiation therapy is complete or after achieving complete or partial remission of the primary cancer. Said maintenance regimen may be followed whether or not active disease is determined to be present.

In various embodiments of the invention, a decision to use L1CAM inhibition as a treatment may be supported by determining that the cancer and/or its metastasis to be treated expresses L1CAM and optionally one or more of EphB2, CD133 and/or CD44. Expression of L1CAM may be determined by any method known in the art, for example as discussed in the sections below. In certain non-limiting embodiments, expression of L1CAM may be detected using an antibody specific for L1CAM or amplification of L1CAM-encoding mRNA using polymerase chain reaction (PCR).

In various non-limiting embodiments, the invention provides for a method of reversing chemoresistance of a cancer cell to a chemotherapy agent, comprising administering, to the cancer cell, an effective amount of L1CAM inhibitor. In non-limiting embodiments, the cancer cell is a metastatic cancer. In non-limiting embodiments, the cancer is a breast, lung, renal, or colorectal cancer. In non-limiting embodiments, the chemotherapeutic agent is carboplatin or methotrexate. In a specific non-limiting embodiment, the cancer is Kras-mutant lung cancer and the chemotherapeutic agent is carboplatin or methotrexate. "Reversing chemoresistance" means that administration of L1CAM inhibitor increases the sensitivity of the cancer cell, cells or tumor to the anti-cancer effect of the chemotherapeutic agent relative to a control cancer cell not treated with L1CAM inhibitor (for example, where the cancer cell is deemed to have a lower than expected response to the chemotherapeutic agent). In a specific non-limiting embodiment, the increase in sensitivity is at least about 30 percent.

An L1CAM inhibitor is an agent that reduces the ability of L1CAM to co-opt blood vessels and/or reduces the ability of L1CAM to reinitiate or promote tumor growth or spread (e.g., the inhibitor reduces tumor cell invasiveness) and can be used to eliminate quiescent cells within tumors. An L1CAM inhibitor may act, for example and not by way of limitation, by reducing expression of L1CAM in the cancer cell or removing L1CAM from the cancer cell surface or binding to L1CAM such that its ability to bind to an endothelial cell or other cancer cells or normal tissue is reduced, for example by reducing the amount of L1CAM available for cell binding, by physical inhibition or by labeling L1CAM-expressing cells and thus marking them for destruction by the immune system.

In non-limiting embodiments, where the subject is a human, L1CAM to be inhibited is human L1CAM having an amino acid sequence as set forth in UniProtKB Accession No. P32004 and/or NCBI Accession Nos. NM_000425 version NM_000425.4 and/or NM_001278116 version NM_001278116.1.

In non-limiting embodiments, an L1CAM inhibitor may be an immunoglobulin, for example an antibody or antibody fragment or single chain antibody that specifically binds to L1CAM, or a therapeutic molecule that comprises one or more immunoglobulin region(s). Non-limiting examples of such antibodies are disclosed in U.S. Pat. No. 8,138,313, International Patent Application Publication No. WO 2007114550, and International Patent Application Publication No. WO 2008151819, as well as antibodies that compete with the antibodies described in these citations for L1CAM binding. In certain non-limiting embodiments an anti-L1CAM antibody or antibody fragment may be used to prepare a human, humanized, or otherwise chimeric antibody that is specific for L1CAM for use according to the invention. In certain non-limiting embodiments, an L1CAM antibody, antibody fragment, or single chain antibody may inhibit binding of L1CAM to an endothelial cell or a blood capillary, to L1CAM or other molecules on neighboring cancer or stromal cells, or to other components of the extracellular matrix under physiologic conditions, for example in vitro or in vivo. In certain non-limiting embodiments, an L1CAM inhibitor comprises immunoglobulin regions that bind to L1CAM and CD133 (the immunoglobulin is bi-specific). In certain non-limiting embodiments, an L1CAM inhibitor comprises immunoglobulin regions that bind to L1CAM and CD44. In certain non-limiting embodiments, an L1CAM inhibitor binds to L1CAM as well as a T cell antigen. In certain non-limiting embodiments, an L1CAM inhibitor binds to L1CAM as well as an NK cell antigen. In certain non-limiting embodiments, an L1CAM inhibitor binds to L1CAM and EphB2.

In non-limiting embodiments, an L1CAM inhibitor may be a nucleic acid, for example, a short hairpin, interfering, antisense, or ribozyme nucleic acid comprising a region of homology to an L1CAM mRNA. For example, such nucleic acids may be between about 15 and 50 or between about 15 and 30 or between about 20 and 30 nucleotides long, and be able to hybridize to L1CAM mRNA under physiologic conditions. A non-limiting example of a short hairpin (sh) RNA that inhibits L1CAM is set forth in the example below. In non-limiting embodiments, an L1CAM inhibitor which is a nucleic acid may be provided in a L1CAM-expressing cancer cell via a vector, for example a lentivirus, which may be selectively targeted to said cancer cell and/or wherein expression of the L1CAM inhibitor nucleic acid may be directed by a promoter which is selectively active in tumor cells. Non-limiting examples of nucleic acid sequence of an L1CAM mRNA include the sequence set forth in NCBI Accession Nos. NM_000425 version NM_000425.4 and/or NM_001278116 version NM_001278116.1. In one specific non-limiting embodiment, the L1CAM inhibitor is RNAi TRCN0000063916 (The RNAi Consortium, Public TRC Portal), having a hairpin sequence (SEQ ID NO: 1)
5'-CCGGACGGGCAACAACAGCAACTTTCTCGAGAAAGTTGCTGTTGTTG

CCCGTTTTTTG and a target sequence ACGGGCAACAACAGCAACTTT (SEQ ID NO:2);

or the hairpin sequence

5'-CCGGCCACTTGTTTAAGGAGAGGATCTCGAGATCCTCTCCTTAAACA (SEQ ID NO: 3)
AGTGGTTTTTG and a target sequence CCACTTGTTTAAGGAGAGGAT (SEQ ID NO:4);
or the hairpin sequence

5'-CCGGGCCAATGCCTACATCTACGTTCTCGAGAACGTAGATGTAGGCA (SEQ ID NO: 5)
TTGGCTTTTTG and a target sequence GCCAATGCCTACATCTACGTT (SEQ ID NO:6)

In certain non-limiting embodiments, the L1CAM inhibitor may be an antibody directed against a mutated L1CAM protein that is expressed on the surface of a MetCSC at high level. Non-limiting examples of mutated L1CAM proteins are set forth in Vos, Y. J., and Hofstra, R. M. (2010) and in Faltas et al., 2016, Nat. Genet. 48(12): 1490-1499, both incorporated by reference herein. An updated and upgraded L1CAM mutation database. Hum Mutat 31, E1102-1109.

In certain non-limiting embodiments, the L1CAM inhibitor may be an agent or agents that can edit the L1CAM gene, for example via CRISPR/Cas9-mediated knockout of the L1CAM gene (see, e.g. FIG. 21 and working examples below). Genome editing is a technique in which endogenous chromosomal sequences present in one or more cells within a subject, can be edited, e.g., modified, using targeted endonucleases and single-stranded nucleic acids. The genome editing method can result in the insertion of a nucleic acid sequence at a specific region within the genome, the excision of a specific sequence from the genome and/or the replacement of a specific genomic sequence with a new nucleic acid sequence. A non-limiting example of a genome editing technique is the CRISPR/Cas9 system. Non-limiting examples of such genome editing techniques are disclosed in PCT Application Nos. WO 2014/093701 and WO 2014/165825, the contents of which are hereby incorporated by reference in their entireties. In certain embodiments, the genome editing technique can include the use of one or more guide RNAs (gRNAs), complementary to a specific sequence within a genome, including protospacer adjacent motifs (PAMs), to guide a nuclease, e.g., an endonuclease, to the specific genomic sequence, for example a sequence necessary for expression of L1CAM (including but not limited to the coding region of the gene itself and/or its promoter); the complementary region may be at least about 10 nucleotides or at least about 20 nucleotides or at least about 30 nucleotides in length. A non-limiting example of an endonuclease includes the clustered, regularly interspaced short palindromic repeat (CRISPR) associated protein 9 (Cas9). In certain embodiments, the endonuclease can result in the cleavage of the targeted genome sequence and allow modification of the genome at the cleavage site through nonhomologous end joining (NHEJ) or homologous recombination. In certain embodiments, a genome editing technique of the present disclosure can include the introduction of an expression vector comprising a nucleic acid sequence that encodes a Cas protein or a mutant thereof, e.g., Cas9D10A, into one or more cells of the subject. In certain embodiments, the vector can further comprise one or more gRNAs for targeting the Cas9 protein to a specific nucleic acid sequence within the genome. In certain embodiments, the nucleic acid sequence encoding the Cas protein can be operably linked to a regulatory element, and when transcribed, the one or more gRNAs can direct the Cas protein to the target sequence in the genome and induce cleavage of the genomic loci by the Cas protein. In certain embodiments, the Cas9 protein cuts about 3-4 nucleotides upstream of the PAM sequence present adjacent to the target sequence. In certain embodiments, the regulatory element operably linked to the nucleic acid sequence encoding the Cas protein can be a promoter, e.g., an inducible promoter such as a doxycycline inducible promoter. The term "operably linked," when applied to DNA sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal. In certain embodiments, the Cas9 enzyme encoded by a vector of the present invention can comprise one or more mutations. The mutations may be artificially introduced mutations or gain- or loss-of-function mutations. Non-limiting examples of such mutations include mutations in a catalytic domain of the Cas9 protein, e.g., the RuvC and HNH catalytic domains, such as the D10 mutation within the RuvC catalytic domain and the H840 in the HNH catalytic domain. In certain embodiments, a mutation in one of the catalytic domains of the Cas9 protein results in the Cas9 protein functioning as a "nickase," where the mutated Cas9 protein cuts only one strand of the target DNA, creating a single-strand break or "nick." In certain embodiments, the use of a mutated Cas9 protein, e.g., Cas9D10A, allows the use of two gRNAs to promote cleavage of both strands of the target DNA. Additional non-limiting examples of Cas9 mutations include VP64, KRAB and SID4X. In certain embodiments, the genome editing technique of the present disclosure can further include introducing into the one or more cells an additional vector comprising a nucleic acid. In certain embodiments, this vector can further comprise one or more targeting sequences that are complementary (e.g., can hybridize) to the same and/or adjacent to the genomic sequences targeted by the gRNAs to allow homologous recombination to occur and insertion of the nucleic acid sequence (i.e., donor nucleic acid sequence) into the genome.

5.2 Assay Systems

In various embodiments, the present invention relates to assay systems and components thereof for producing models of metastatic disease and using such models as assay systems for identifying therapeutic agents.

In various non-limiting embodiments, the invention provides for an assay for identifying an agent that inhibits metastasis, comprising an organoid culture comprising cancer cells that express L1CAM. Said cells may express high levels of L1CAM and/or medium or high levels of EphB2. In certain non-limiting embodiments, said cancer cells are MetCSCs and optionally express an exogenous marker, for example a fluorescent exogenous marker. Certain non-limiting embodiments provide for a method of identifying a MetCSC, comprising determining that the cell expresses L1CAM, for example surface expression of a high level of L1CAM. In certain non-limiting embodiments, the MetCSC further expresses a medium or high level of EphB2. Expression of L1CAM and optionally EphB2 may be determined by any method known in the art, including but not limited to antibody-based or PCR-based methods. In certain non-limiting embodiments, the MetCSC is isolated from a primary cancer of a subject. In certain non-limiting embodiments, the MetCSC is isolated from a metastasis of a subject. In certain non-limiting embodiments, the cancer, either primary or metastatic, is of breast, lung, renal, or colorectal origin.

In certain non-limiting embodiments, where the cancer, primary or metastatic, is of colorectal origin, the MetCSC may further be identified as exhibiting surface expression of one or more of CD133 and/or CD44 in addition to L1CAM and optionally EphB2.

Certain non-limiting embodiments provide for an isolated MetCSC cell expressing L1CAM. In certain non-limiting embodiments, the MetCSC expresses a high level of L1CAM. In certain non-limiting embodiments, the isolated MetCSC comprises an introduced exogenous marker. In certain non-limiting embodiments, the exogenous marker is a fluorescent marker. In particular embodiments, the invention provides for a composition comprising cells that are an essentially pure population of MetCSCs expressing L1CAM. In non-limiting embodiments, the MetCSCs may be isolated using FACS or other cell-isolating methods known in the art.

The above MetCSCs may be used to prepare a model system of metastasis that may be used to study the metastatic process and may be used as an assay system to identify agents for inhibiting and thereby treating metastatic disease in a subject.

In certain non-limiting embodiments, the invention provides for a model system of metastasis/assay system comprising an organoid culture formed of cancer cells that express L1CAM and optionally EPCAM. In certain non-limiting embodiments, the cancer cells further express EphB2. In certain embodiments the cancer cells express high levels of L1CAM and med/high levels of EphB2.

In certain non-limiting embodiments, the invention provides for a model system of metastasis/assay system comprising an organoid culture formed of MetCSC cells that express L1CAM and EPCAM. In certain non-limiting embodiments, the MetCSC cells further express EphB2. In certain embodiments the MetCSC cells express high levels of L1CAM and med/high levels of EphB2. See, for example, Drost et al., 2016, Nature Protocols 11:347-358 for description of organoid culturing techniques. For example, the culture medium for organoid culture may comprise Wnt. MetCSC cells, as described above, may be used as the basis for organoid development. A non-limiting example of an in vitro assay system comprises said MetCSC, under conditions that promote organoid formation. An agent effective in inhibiting metastasis from forming and/or progressing may be identified as an agent that reduces the occurrence or growth of organoids in said system.

In certain non-limiting embodiments, a MetCSC, as described above, optionally having been cultivated to form an organoid, may be introduced into a laboratory animal such as an athymic mouse or other immunocompromised non-human host, and used to test whether an administered agent is effective at delaying, reducing the number, or inhibiting the growth or dispersal of metastatic growth resulting from said MetCSC, thereby identifying it as having antimetastasis therapeutic activity.

In related non-limiting embodiments, the invention provides for a method of identifying an agent that inhibits metastasis, comprising:

(i) providing an organoid culture comprising cancer cells that express L1CAM;

(ii) contacting the organoid culture with a test agent;

(iii) determining whether the level of L1CAM expression decreases in the test agent-contacted culture relative to a control organoid culture that has not been contacted with the test agent;

wherein a decrease in the level of L1CAM expression, interactions, and/or signaling in response to contacting with the test agent indicates that the test agent inhibits metastasis.

5.3 Kits

In certain non-limiting embodiments, the invention provides for a kit for determining whether a subject having a cancer is at increased risk for metastatic spread of the cancer, comprising means for determining whether a cell of the cancer expresses L1CAM, and, optionally, instructional material that indicates that expression, on a cancer cell, of L1CAM indicates that the subject may benefit from L1CAM inhibitor therapy.

In certain non-limiting embodiments, the invention provides for a kit for identifying an agent that inhibits metastasis, comprising (i) cancer cells that express L1CAM and (ii) means for determining the L1CAM expression level. In various non-limiting embodiments, the cancer cells can express high levels of L1CAM and optionally further express one or more of CD133, CD44 and/or EphB2. In certain non-limiting embodiments, the means for detecting L1CAM expression is an oligonucleotide probe that detectably binds to L1CAM. In certain non-limiting embodiments, the means for detecting L1CAM expression is a pair of primers that can be used in polymerase chain reaction to determine the L1CAM expression level. In certain non-limiting embodiments, the means for detecting L1CAM expression is an immunoglobulin that specifically binds to L1CAM.

Non-limiting examples of types of kits include, but are not limited to, arrays/microarrays, L1CAM-specific antibodies and beads, which may contain one or more primer, probe, antibody, or other detection reagent(s) for detecting L1CAM and optionally other markers set forth above (EphB2, CD133, CD44).

In non-limiting embodiments, the present invention provides for a kit for determining whether a subject having a cancer is at increased risk of having or developing a metastasis of the cancer, comprising a means for detecting the protein level (directly or via mRNA) of L1CAM and optionally EphB2, CD133 and/or CD44.

In certain non-limiting embodiments, surface expression of L1CAM and optionally EphB2, C44, and/or CD133 is detected.

In non-limiting embodiments, a kit may comprise at least one antibody for immunodetection of L1CAM and optionally EphB2, CD44 and/or CD133. Antibodies, both polyclonal and monoclonal, including molecules comprising an antibody variable region or subregion thereof, specific for these proteins, may be prepared using conventional immunization techniques, as will be generally known to those of skill in the art. The immunodetection reagents of the kit may include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels (3H, 35S, 32P, 14C, 1311) or enzymes (alkaline phosphatase, horseradish peroxidase). Alternatively, a detectable moiety may be comprised in a secondary antibody or antibody fragment which selectively binds to the first antibody or antibody fragment (where said first antibody or antibody fragment specifically recognizes a serpin).

In a further non-limiting embodiment, a L1CAM-specific antibody (or optionally EphB2, CD44 and/or CD133-specific antibody) may be provided bound to a solid support, such as a column matrix, an array, or well of a microtiter plate. Alternatively, the support may be provided as a separate element of the kit.

In certain embodiments, types of kits include, but are not limited to, packaged probe and primer sets (e.g. TaqMan probe/primer sets), which may further contain one or more probes, primers, or other detection reagents for detecting one or more serpin, for example neuroserpin, serpin B2, serpin E1, serpin E2 or serpin D1.

In a specific, non-limiting embodiment, a kit may comprise a pair of oligonucleotide primers, suitable for polymerase chain reaction (PCR) or nucleic acid sequencing, for detecting the protein(s) to be identified. A pair of primers may comprise nucleotide sequences complementary L1CAM or optionally EphB2, CD133 and/or CD44-encoding mRNA and be of sufficient length to selectively hybridize with said mRNA. Multiple marker protein-specific primers may be included in the kit to simultaneously assay a plurality of proteins (e.g. L1CAM and optionally one or more of EphB2, CD44 and/or CD133). The kit may also comprise one or more polymerase, reverse transcriptase, and nucleotide bases, wherein the nucleotide bases can optionally be further detectably labeled.

In non-limiting embodiments, a primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In a further non-limiting embodiment, an oligonucleotide primer may be immobilized on a solid surface or support, for example, on a nucleic acid microarray, and optionally the position of each oligonucleotide primer bound to the solid surface or support is known and identifiable.

In a specific, non-limiting embodiment, a kit may comprise at least one nucleic acid probe, suitable for in situ hybridization or fluorescent in situ hybridization, for detecting the protein to be identified.

In one specific non-limiting embodiment, a kit may comprise one or more of: a probe, primers, microarray, antibody or antibody fragment suitable for detecting L1CAM and one or more of EphB2, CD44, and/or CD133.

In certain non-limiting embodiments, a kit may comprise one or more detection reagents and other components (e.g. a buffer, enzymes such as alkaline phosphatase, antibodies, and the like) necessary to carry out an assay or reaction to determine the expression levels of a biomarker.

In certain non-limiting embodiments, the invention provides for a diagnostic method for determining whether a subject having a cancer is at increased risk for metastatic spread of the cancer, comprising means for determining whether a cell of the cancer expresses L1CAM and EphB2, where if the cancer cell is found to express L1CAM and EphB2, and particularly high L1CAM and med/high EphB2, the subject is at increased risk for developing metastatic disease relative to a subject having a cancer lacking those markers, and may benefit from L1CAM inhibitor therapy. The method may further include informing the subject or a health care worker of the result of the determination and the associated risk. The method may further include, where an increased risk is indicated, recommending or performing an additional diagnostic procedure, for example an imaging study, to determine whether the subject has detectable metastatic disease. Non-limiting examples of imaging modalities include magnetic resonance imaging, computerized tomography and positron emission tomography. In a related embodiment, the invention provides for a method of treatment comprising performing the diagnostic method and then, where increased risk is indicated, administering a therapeutic amount of L1CAM inhibitor.

6. EXAMPLE: L1CAM INHIBITION INHIBITS/REDUCES METASTASES AND INHIBITS PROGRESSION OF ESTABLISHED METASTASES

Metastasis is a highly inefficient process, in that primary tumor cells must first undergo epitheial-mesenchymal transition and escape from the primary tumor. After dissemination in the bloodstream, the vast majority of tumor cells die, leaving only a tiny fraction capable of surviving in a hostile foreign organ. These remaining few tumor cells may lie dormant for months or years, and then, when conditions are right, start to proliferate and reinitiate tumor growth. Once this so-called macrometastatic growth has been initiated, it is usually still possible to kill the bulk of tumor cells with chemotherapy, radiation, targeted therapy and/or immunotherapy—sometimes even to the point of no measurable disease—but a true cure is rarely possible.

This suggests that the tumor cells that form macrometastases—the MetCSCs—are resistant to chemotherapy, radiation, targeted therapy and/or immunotherapy, as they must survive these therapies applied to treat, first, the primary tumor and, later, its metastases. In addition, MetCSCs are able to undergo long-term self-renewal, have the ability to generate heterogeneous progeny (recapitulating tumor heterogeneity) and are capable of entering and exiting a dormant state, in which they can, potentially, exist for years (even decades, as seen in the case of ER/PR positive breast cancer).

Because chemotherapy may not be a treatment option for controlling metastatic growth, it is important to understand MetCSC mechanistically and identify therapeutic targets that will specifically kill these cells. To date, model systems for studying metastases have been imperfect.

L1CAM is a molecule associated with various cancers. Aberrant L1CAM expression has been demonstrated at the leading edge of primary tumors, and is associated with invasion, metastasis and poor prognosis in many human cancers including lung, breast and colon carcinomas (Voura et al., 2001; Ben et al., 2010; Tsutsumi et al., 2011; Schroder et al., 2009; Tischler et al., 2011; Boo et al., 2007; Chen et al., 2013; Fogel et al., 2003a; Doberstein et al., 2011; Fogel et al., 2003b; Kim et al., 2009; Maness et al., 2007). L1CAM expression is normally restricted to neurons where it mediates axonal guidance through interactions of the growth cone with surrounding components (Castellani et al., 2002; Wiencken-Barger et al., 2004).

Figure 6A:
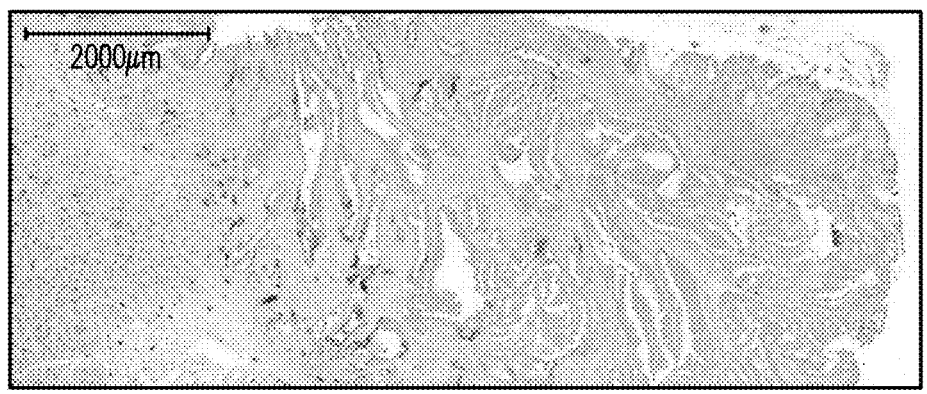
Figure 6B:
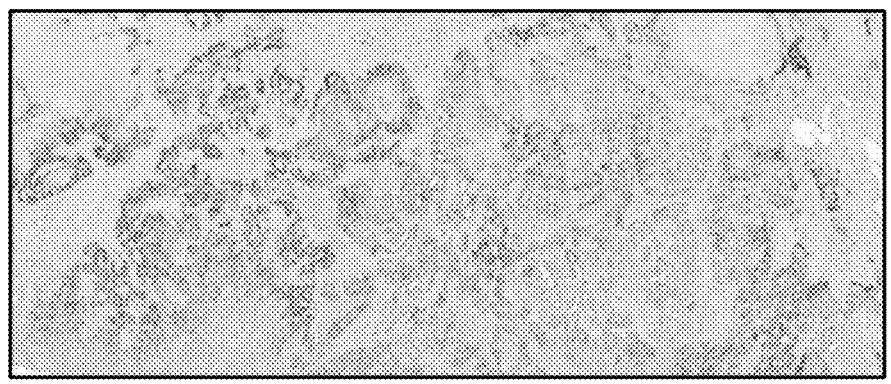
Figure 6C:
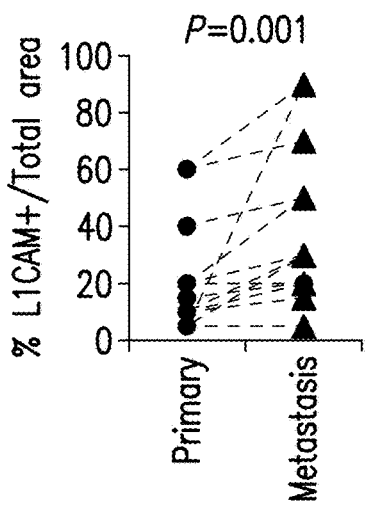
Figure 6D:
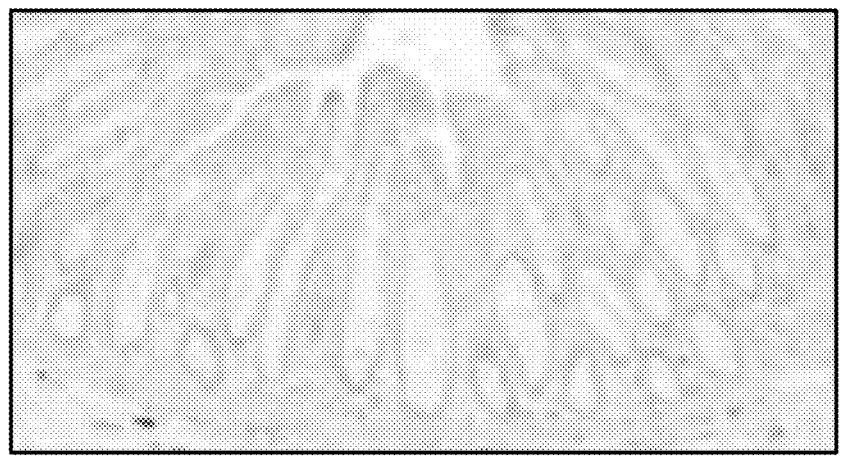

A number of immunohistologic studies were performed to further study the expression of L1CAM during the metastatic process. L1CAM was found to be expressed at the primary tumor invasion front (FIG. 5A) where the cells remain quiescent (low Ki67; FIG. 5B). Strikingly, well-differentiated areas of tumors with intact glandular morphology expressed L1CAM predominantly in Ki67-low, quiescent cells; while in poorly-differentiated areas with loss of epithelial integrity, L1CAM expression could be observed in Ki67-high cells (FIGS. 5A, 5B). L1CAM was not expressed in adjacent normal colonic epithelial cells (FIG. 6D). The expression of L1CAM is increased in tumor relative to normal tissue, and in metastasis relative to tumor (FIG. 6A-C, FIG. 7A-C). Finally, post-chemotherapy residual disease is strongly LCAM1+, and the cells are quiescent (low Ki67; FIG. 8A-B). All these features are consistent with L1CAM being a marker—and functionally relevant molecule—of MetCSCs.

Figure 1D:
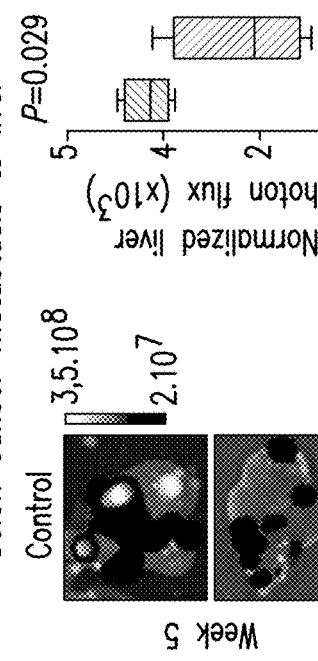

Experiments were performed to determine whether inhibition of L1CAM could impact metastasis. Cancer cells which either were transfected with shL1CAM (to knock down L1CAM expression) or control cancer cells were introduced into athymic mice (by intracardiac injection to assess brain or bone metastasis and by tail vein injection to assess lung metastasis) and the amount of metastases determined after several weeks using bioluminescence imaging. As shown in FIG. 1A-D, the extent of metastatic disease was dramatically reduced in mice that had received L1CAM-depleted cancer cells. L1CAM depletion (L1CAM inhibition) significantly reduced the progression of metastatic disease, including metastasis of breast cancer to lung (FIG. 1A), metastasis of breast cancer to bone (FIG. 1B), metastasis of colon cancer to liver (FIG. 1C), and metastasis of renal cell cancer to brain (FIG. 1D).

Experiments were also performed to determine whether L1CAM inhibition could be used to treat existing metastatic disease. In these experiments, expression of shL1CAM was placed under the control of an inducible promoter which could be activated by the drug doxycycline, so that knockdown of L1CAM could be turned on after dissemination of tumor cells had occurred. Athymic mice receiving either shL1CAMind-transfected cancer cells or control cancer cells were treated with doxycycline at day 14 and then assessed for metastatic disease by bioluminescence imaging at day 28 (FIG. 2). The results are shown in FIGS. 2 and 3A-C, which show that L1CAM knockdown inhibited the growth of established metastases and, in particular, metastasis of lung cancer to brain (FIG. 3A), metastasis of breast cancer to bone (FIG. 3B), and metastasis of breast cancer to lung (FIG. 3C). L1CAM has been determined to play a role in vascular co-option, but established metastases outgrow the need for vascular-co-option, making it interesting to observe that L1CAM inhibition also was able to inhibit progression of established metastases (FIG. 4A-B).

7. EXAMPLE: MODEL SYSTEM FOR METASTATIC DISEASE

Experiments were performed to develop models for metastatic disease. In particular, patient-derived cells were used to generate organoids in culture, using a modification of the technique developed by Hans Clevers, in which organoids grow in three dimensions in matrigel and stem cell media enriched with Wnt is used for culturing (FIG. 10). For example, metastatic tumor was harvested from a patient, dissociated into single cells, and then a L1CAM+, EpCAM+ fraction of cells was collected by fluorescence activated cell sorting (FACS) and used to establish organoid cultures (FIG. 11). Of note, EphB2 med; L1CAM+ cells were found to constitute a novel subset of MetCSCs (FIG. 12). When collected from a subject having colorectal cancer, the L1CAM$^{high}$ fraction was found to show increased cell surface expression of established colorectal cancer stem cell markers CD133, CD44 and EphB2 relative to L1CAMW cells (FIG. 13). Results of FACS analysis for markers L1CAM, EphB22, CD133, and CD44 are shown in FIGS. 14 and 15.

Figure 9A:
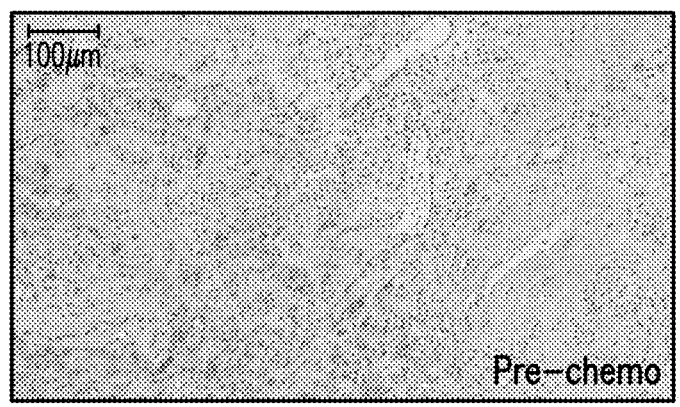
Figure 9B:
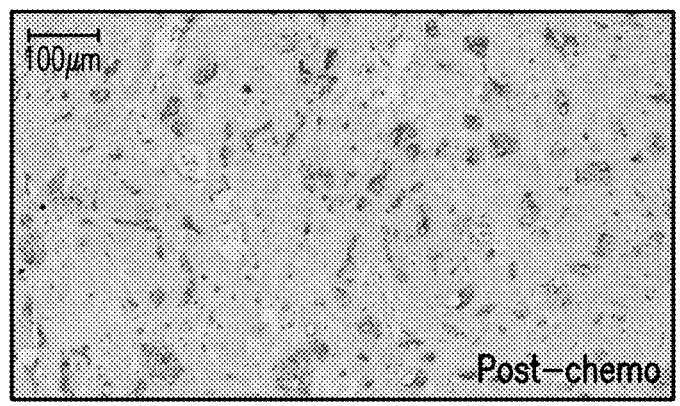
Figure 9C:
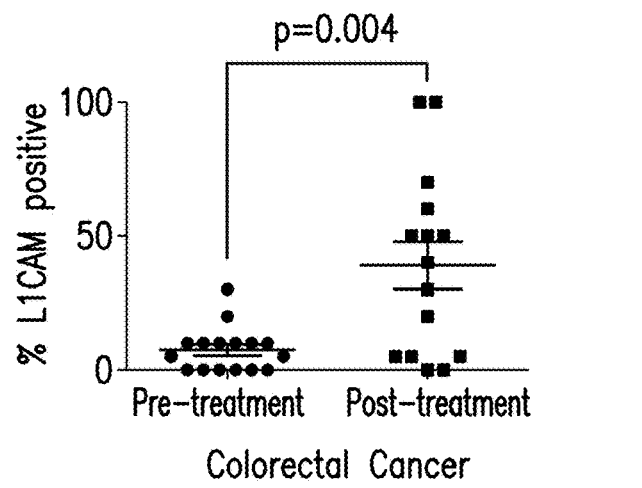
Figure 9D:
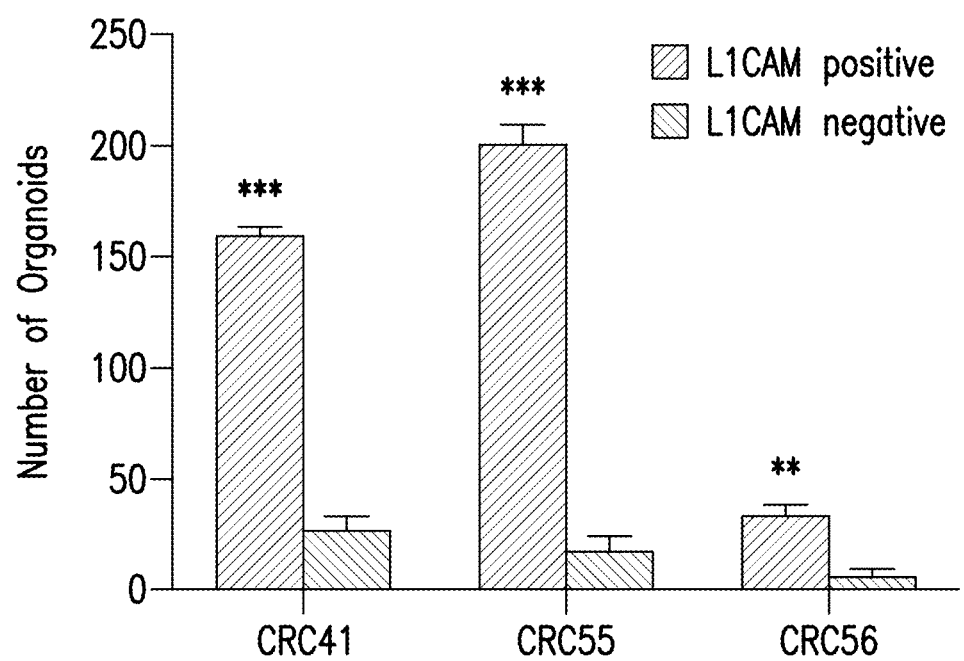

It was further observed that tumor L1CAM expression was associated with organoid-initiating capability (FIGS. 16 and 17). Residual tumors expressing high levels of cell-surface L1CAM could more frequently be cultured as organoids than tumors with low L1CAM levels (FIGS. 9A-C). FACS sorted L1CAMhigh cells from freshly resected residual CRC liver metastases had greater organoid generating-capacity that L1CAMlow cells from the same tumors (FIG. 9D).

Interestingly, L1CAM$_{high}$ cells were found to give rise to both L1CAM$_{high}$ and L1CAM$_{low}$ progeny (FIG. 18). Further, L1CAM+ cells that are Ki67 low in vivo are more capable of organoid-initiation than L1CAM-cells (Ki67 high in vivo) (FIG. 19), suggesting that L1CAM+ cells within patient tumors are slow-cycling reserve cells that can re-enter the cell cycle, reinitiate tumor growth and repopulate heterogenous tumors consisting of both L1CAM$^+$ and L1CAM-cells under permissive conditions. This is demonstrated in FIG. 22, which shows that nascent small organoids are comprised of universally L1CAM+ cells, but as the organoids grow, the cells divide to generate mostly L1CAM-differentiated progeny that populate the bulk of the organoid.

When L1CAM expression was compared between dissociated tumor and the organoids generated from the dissociated tumor, it was found that L1CAM expression was a trait selected for during organoid generation. The results from dissociated tumor collected from two different patients are shown in FIGS. 20A and 20B. When L1CAM was deleted using CRISPR-Cas-9, fewer organoids resulted (FIG. 21), suggesting that L1CAM is required for the survival and/or regrowth of organoid-initiating MetCSCs. Notably, dissociation of intact organoids into single cells markedly upregulated L1CAM expression (FIG. 27).

Patient metastasis-derived organoids were expanded in vitro, FACS sorted into L1CAM$^{high}$ and L1CAM$^{low}$ populations and implanted as subcutaneous xenografts into NSG mice, whereupon the L1CAM$^{high}$ cells displayed greater in vivo tumor re-initiation capacity (FIG. 25A). The subcutaneous tumors displayed well-differentiated glandular epithelial morphology and intestinal mucin secretion (FIG. 25B). FACS sorting of subcutaneous tumor-derived cells based on cell-surface L1CAM expression revealed that L1CAM$^{high}$ cells retained their organoid-reinitiating capacity (FIG. 25C).

Next, we injected Stage III CRC-derived organoids into the splenic vein of immunocompromised NSG mice. Liver metastases thus generated were then passaged as organoids and re-injected into the splenic vein. Such serially passaged liver metastatic organoids not only formed larger liver metastases more rapidly than their parental organoids, but also expressed higher levels of L1CAM (FIG. 26A-D). In sum, L1CAM$^{high}$ cells in therapy-resistant residual metastatic patient tumors are organoid and metastasis-reinitiating stem cells (MetSCs)

8. EXAMPLE: INHIBITION OF L1CAM REVERSES CHEMORESISTANCE

Figure 24:
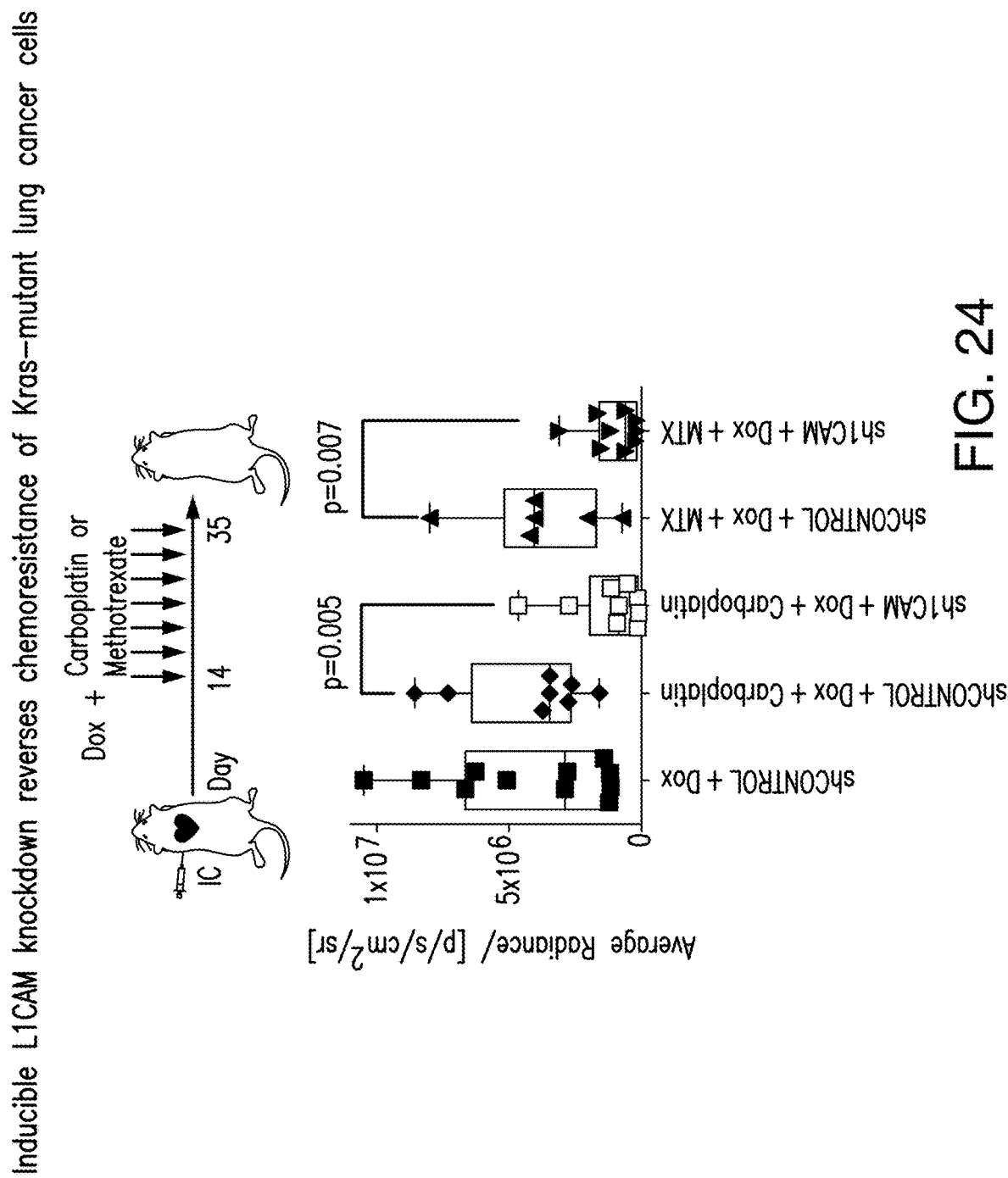

Kras-mutant lung cancer cells that were resistant to carboplatin and methotrexate were transfected with shCONTROL or shL1CAM operably linked to a doxycycline-inducible promoter. shCONTROL or shL1CAM containing cancer cells were then injected, intracardially, into athymic mice (day 0). On day 14, treatment with doxycycline and v=carboplatin or methotrexate was initiated, and tumors were assessed on day 35. As shown in FIG. 24, the cancer cells expressing L1CAM inhibitor were more sensitive to carboplatin or methotrexate than the control cells. This indicates that L1CAM inhibition can render chemoresistant cells more sensitive to chemotherapy.

9. EXAMPLE: L1CAM IS REQUIRED FOR ANOIKIS EVASION AND ORGANOID REGENERATION

Figure 28A:
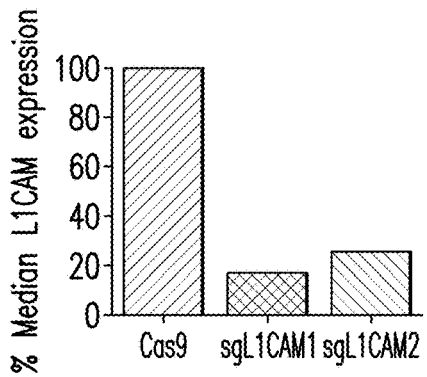
Figure 28B:
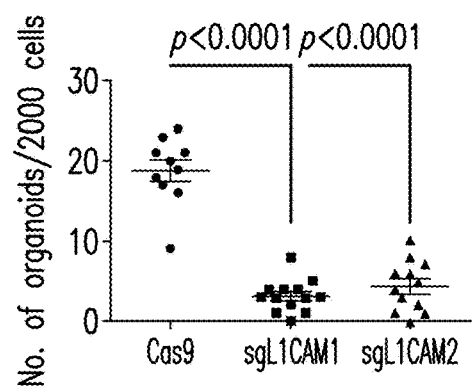
Figure 28C:
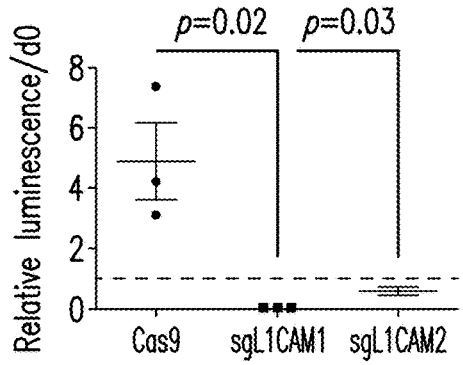
Figure 28D:
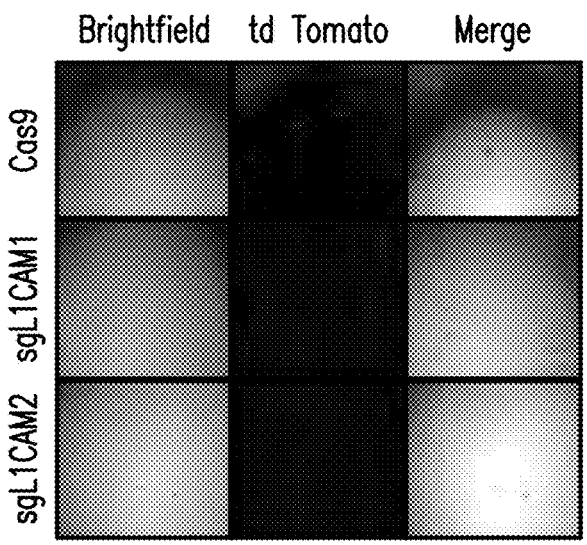
Figure 28E:
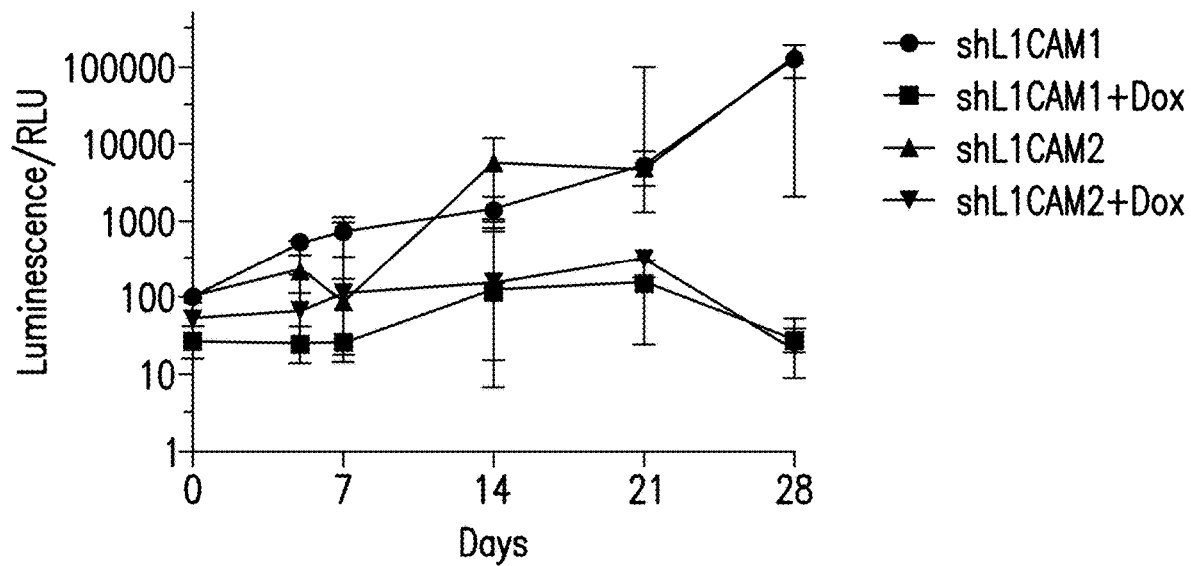
Figure 28F:
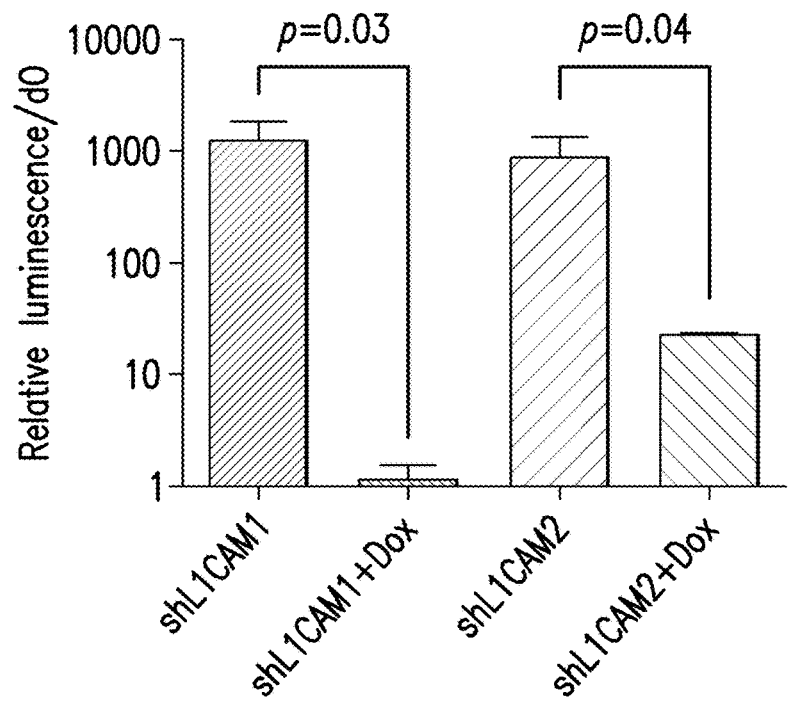
Figure 28G:
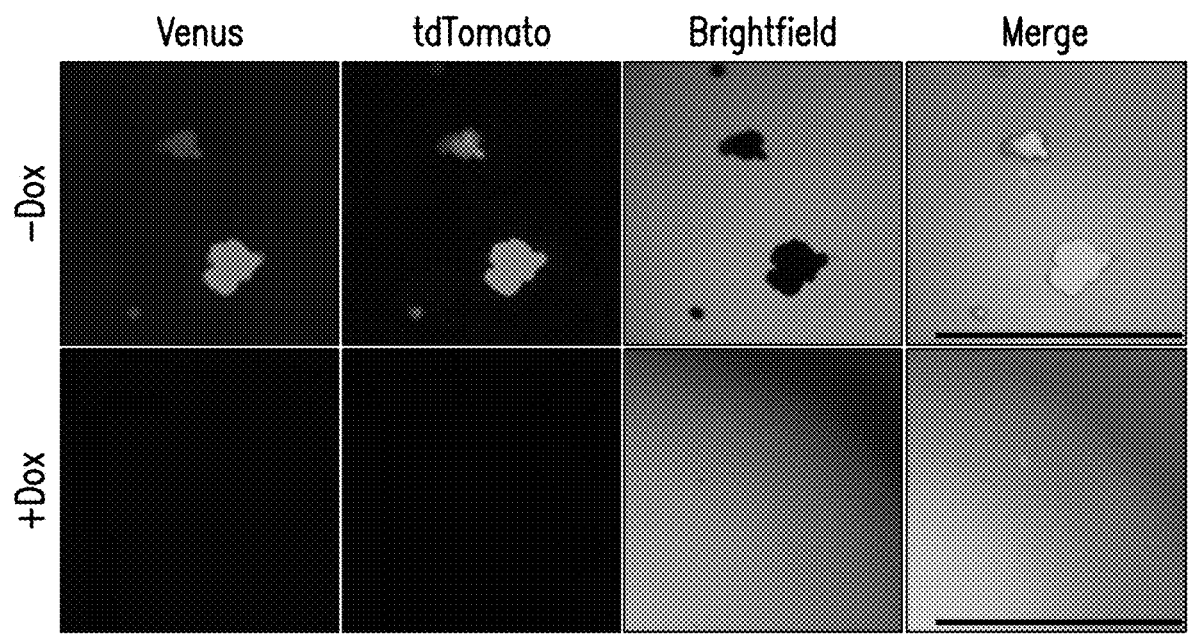
Figure 28H:
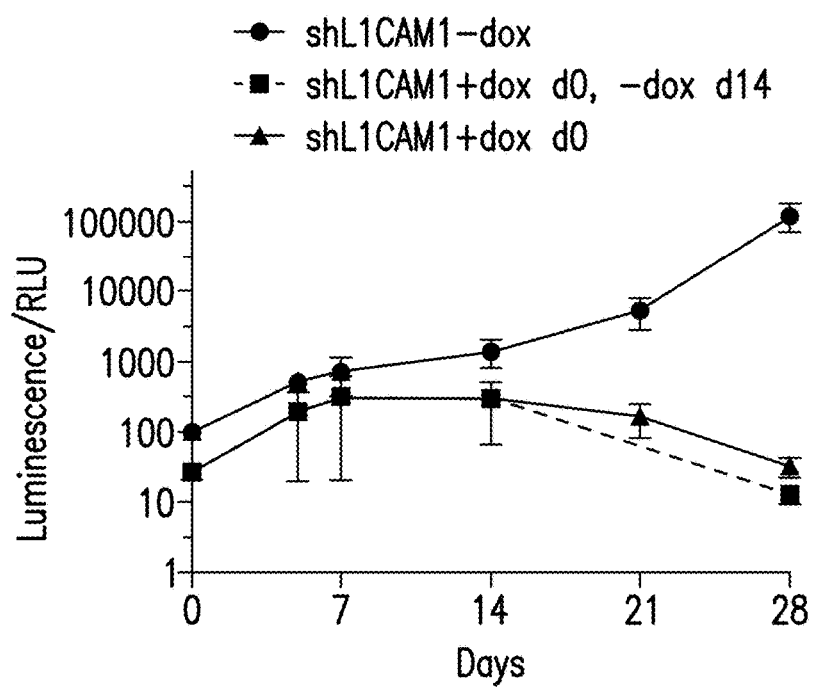
Figure 28I:
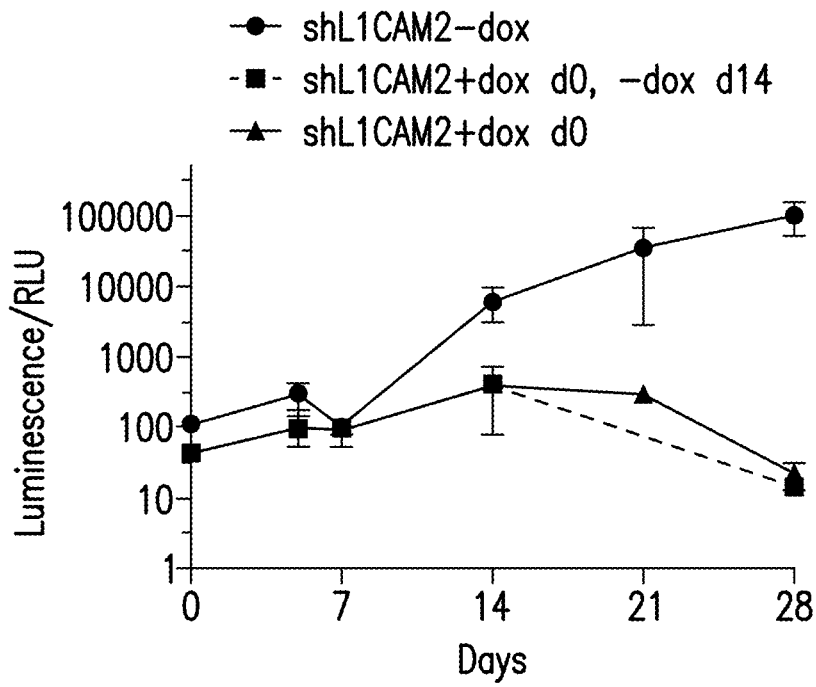

To interrogate whether L1CAM is functionally required for organoid growth or regeneration, we performed CRISPR-Cas9 mediated knockout of L1CAM in metastasis-derived organoids (see FIG. 21). L1CAM-knockout significantly inhibited the ability of organoid-derived single cells to regenerate new organoids (FIG. 28A-D). Similarly, doxycycline inducible knockdown of L1CAM inhibited organoid regeneration (FIG. 28E-G). Notably, withdrawal of doxycycline after 14 days of culture did not permit organoid regrowth, suggesting that L1CAM-deficient metastatic CRC progenitors require L1CAM not only to drive organoid regrowth but also to survive when detached from epithelial structures (FIG. 28H-I).

Figure 28J:
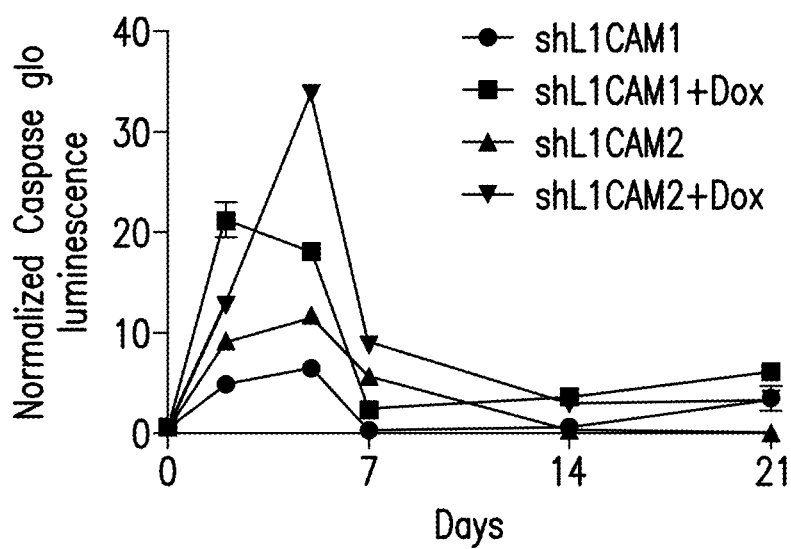
Figure 28K:
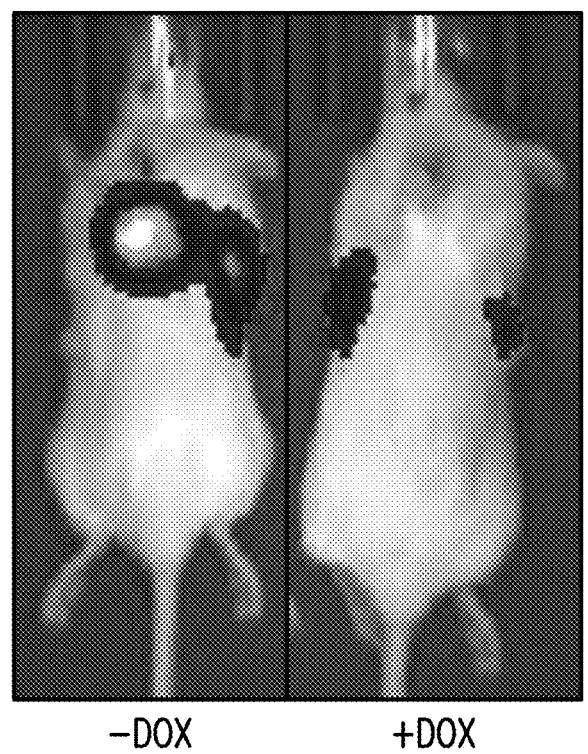
Figure 28L:
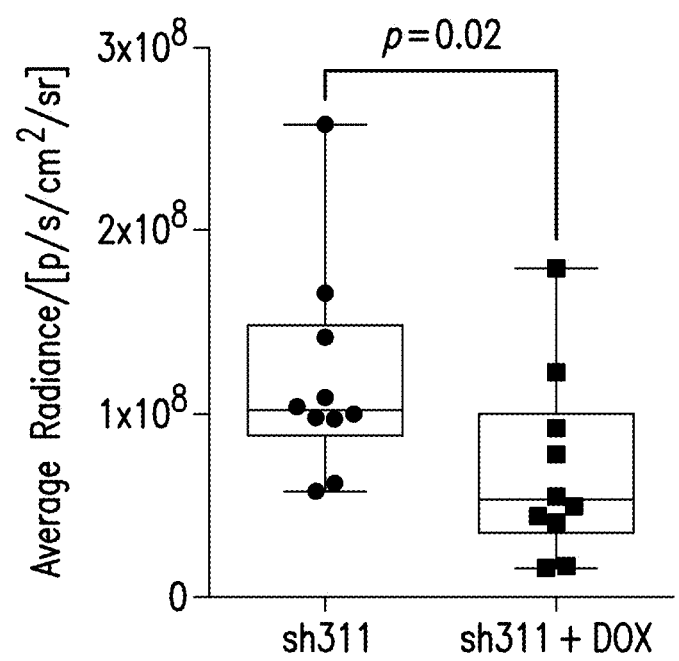

Consistently, L1CAM-deficient cells displayed increased caspase activity in the first week following dissociation (FIG. 28J). Thus, L1CAM-deficient cells demonstrate detachment-induced, caspase-mediated cell death, a.k.a. anoikis. L1CAM knockdown did not alter the expression of genes associated with pluripotency, ISC, wnt-response or differentiation. In vivo, L1CAM knockdown abrogated subcutaneous tumor growth in NSG mice (FIG. 28K-L). In sum, L1CAM does not drive the phenotypic progenitor cell identity of MetSCs, but is required for their survival and regrowth upon epithelial detachment, crucial requirements for successful tumor propagation and metastasis.

Figure 28M:
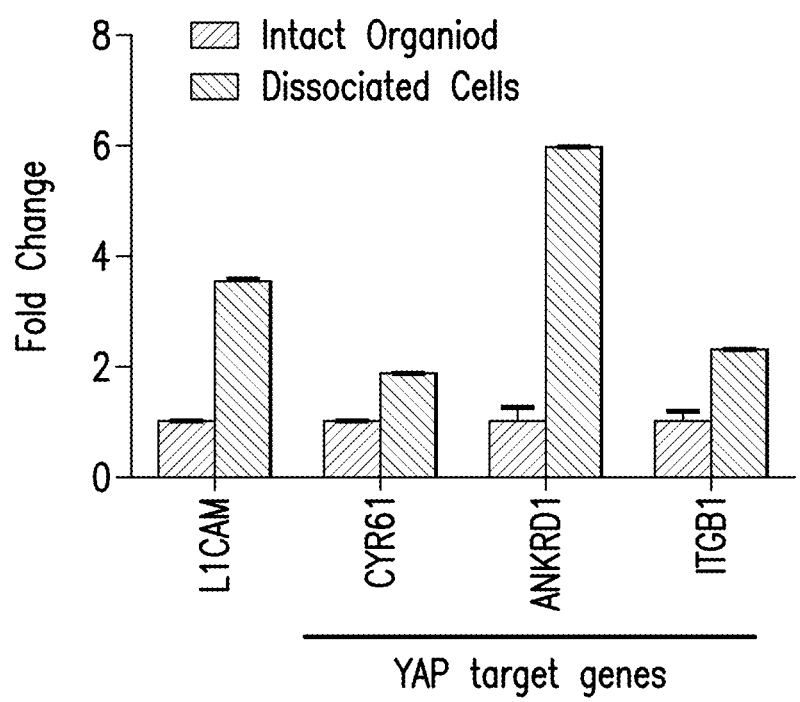

YAP activity is induced by loss of epithelial interaction and contact with stiff basement membrane in multiple contexts (Zhao B, Wei X, Li W, Udan R S, Yang Q, Kim J, Xie J, Ikenoue T, Yu J, Li L, Zheng P, Ye K, Chinnaiyan A, Halder G, Lai Z C, Guan K L. Inactivation of YAP oncoprotein by the Hippo pathway is involved in cell contact inhibition and tissue growth control. Genes Dev. 2007 Nov. 1; 21(21):2747-61, Aragona M, Panciera T, Manfrin A, Giulitti S, Michielin F, Elvassore N, Dupont S, Piccolo S. A mechanical checkpoint controls multicellular growth through YAP/TAZ regulation by actin-processing factors. Cell. 2013 Aug. 29; 154(5):1047-59. Benham-Pyle B W, Pruitt B L, Nelson W J. Cell adhesion. Mechanical strain induces E-cadherin-dependent Yap1 and 3-catenin activation to drive cell cycle entry. Science. 2015 May 29; 348(6238): 1024-7. Gjorevski N, Sachs N, Manfrin A, Giger S, Bragina M E, Ordóñez-Morán P, Clevers H, Lutolf M P. Designer matrices for intestinal stem cell and organoid culture. Nature. 2016 Nov. 24; 539(7630):560-564). Indeed, dissociation of organoids into single cells significantly induced expression of YAP target genes ANKRD1, CYR61 and ITGB1 (FIG. 28M).

10. EXAMPLE: L1CAM-EXPRESSION BY PROGENITOR CELLS IS REQUIRED FOR EPITHELIAL REGENERATION FOLLOWING INJURY

Figure 29A:
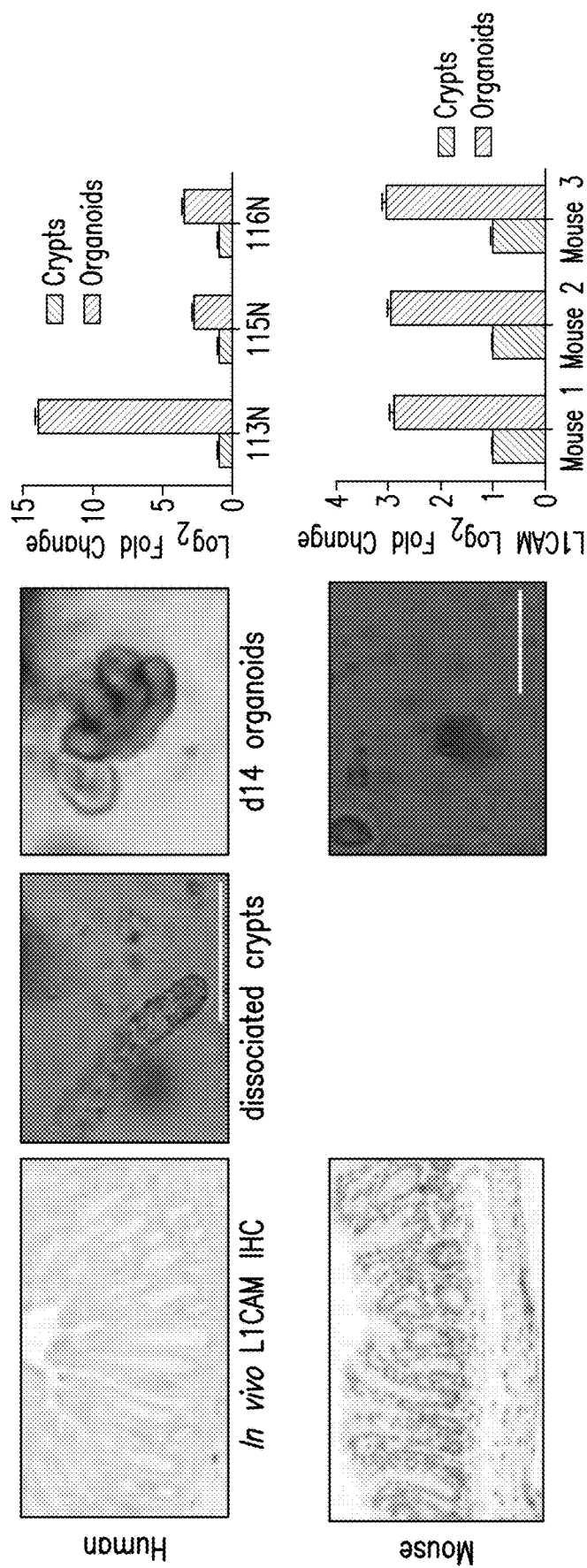
Figure 29B:
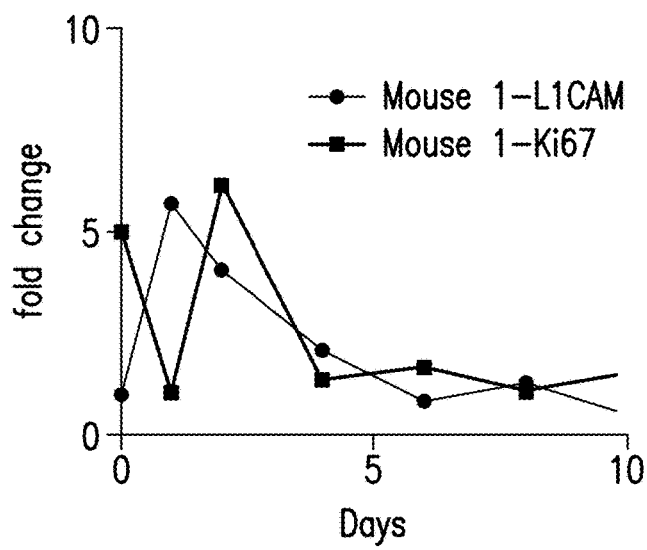
Figure 29C:
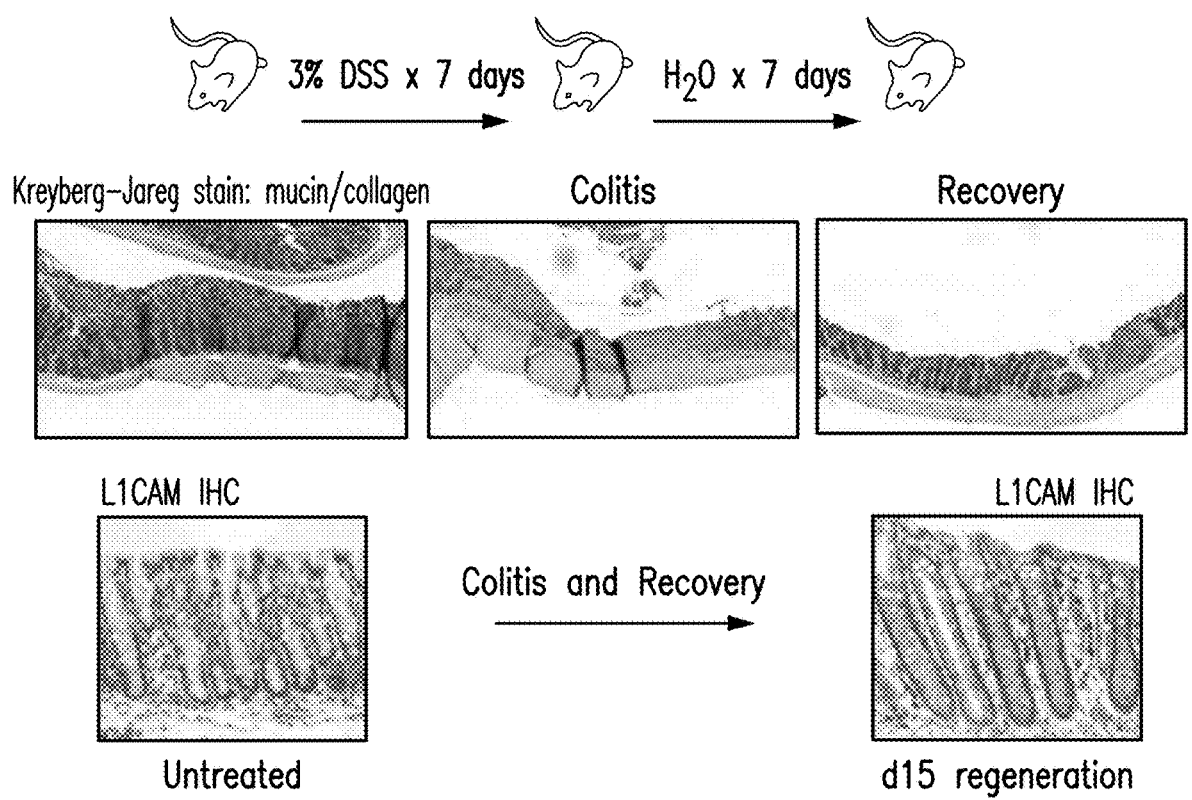
Figure 29D:
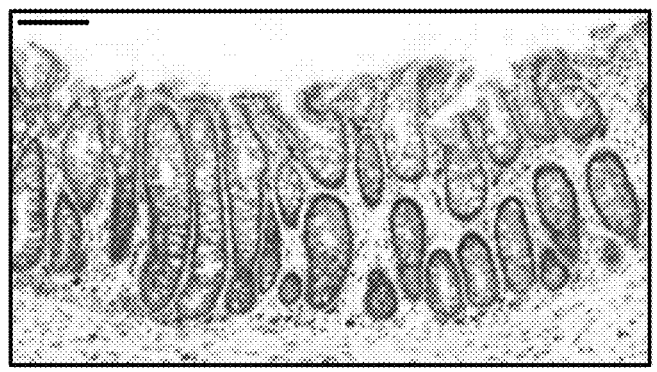
Figure 29E:
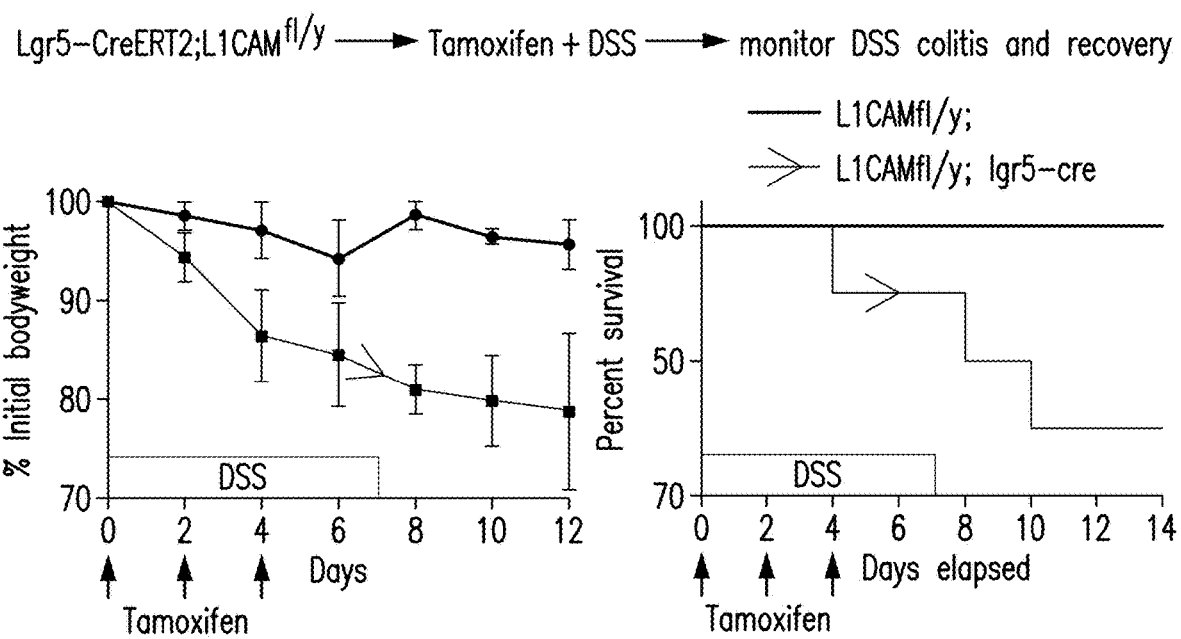

Since L1CAM is required for survival, regrowth and restoration of tissue architecture by transformed epithelial cells, we wondered whether it might also be required in non-transformed epithelia when epithelial integrity is disrupted. As seen in the human, normal mouse colon epithelia did not express significant amounts on L1CAM (FIG. 29A). However, when grown as organoids, non-transformed colon epithelial cells induced L1CAM expression (FIG. 29A). As seen with cancer organoids, normal mouse colon organoids dynamically upregulated L1CAM immediately upon organoid dissociation, with total organoid L1CAM declining over time as the organoids grew larger (FIG. 29B). To test whether L1CAM is induced during epithelial injury in vivo, we treated C57BL6 with dextran sodium sulfate (DSS) water for 7 days. L1CAM was not expressed in control mice given water, but was expressed from day 11-day 16 in regenerating colon crypts in areas that demonstrated DSS damage (FIG. 29C). L1CAM was expressed not in the crypt base compartment associated with rapidly proliferating stem cells, nor in the fully differentiated luminal cells, but instead in the regenerating transit-amplifying colon cells (FIG. 29D).

Figure 29F:
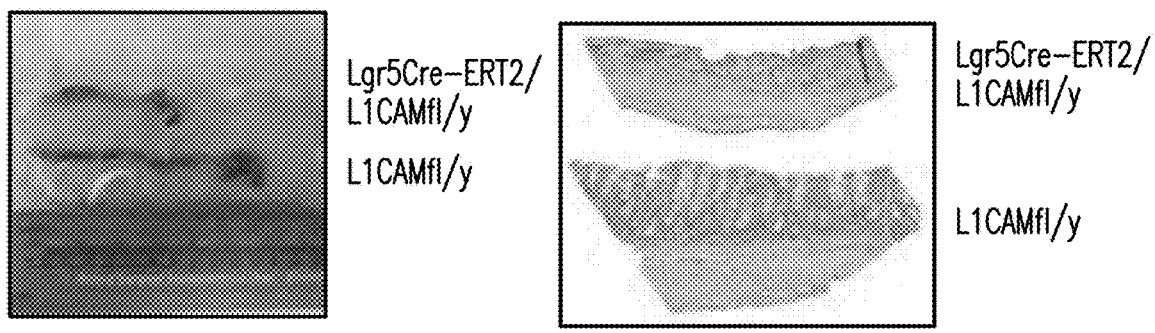

To interrogate the functional significance of L1CAM in colon regeneration, we crossed L1CAM$^{fl/fl}$ mice with the intestinal stem cell-specific Lgr5-GFP-IRES-Cre-ERT2 mice. Cre recombinase expression was induced by treating the mice with IP tamoxifen for three doses concurrent with DSS or water treatment. When given water, tamoxifen-treated mice displayed no alterations in weight (FIG. 29E), behavior or bowel habit. When treated with DSS, tamoxifen-treated Lgr5-GFP-IRES-Cre-ERT2/L1CAM$^{fl/y}$ demonstrated sustained weight loss and reduced survival in comparison to controls. Autopsy revealed significantly shortened colons, with histopathology showing diffuse inflammation with areas of mucosal denudation (FIG. 29F).

11. EXAMPLE: EPITHELIAL DISRUPTION INDUCES L1CAM BY DISPLACING REST FROM THE L1CAM PROMOTER

Figure 30A:
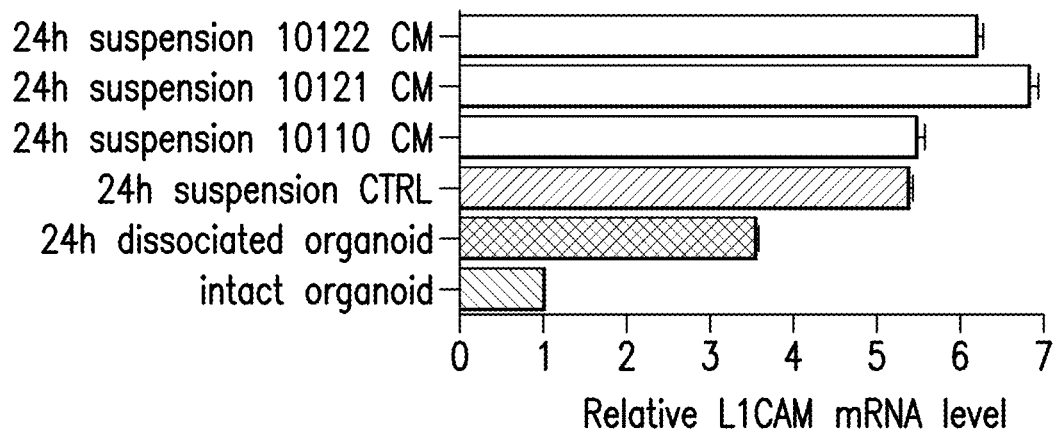
Figure 30B:
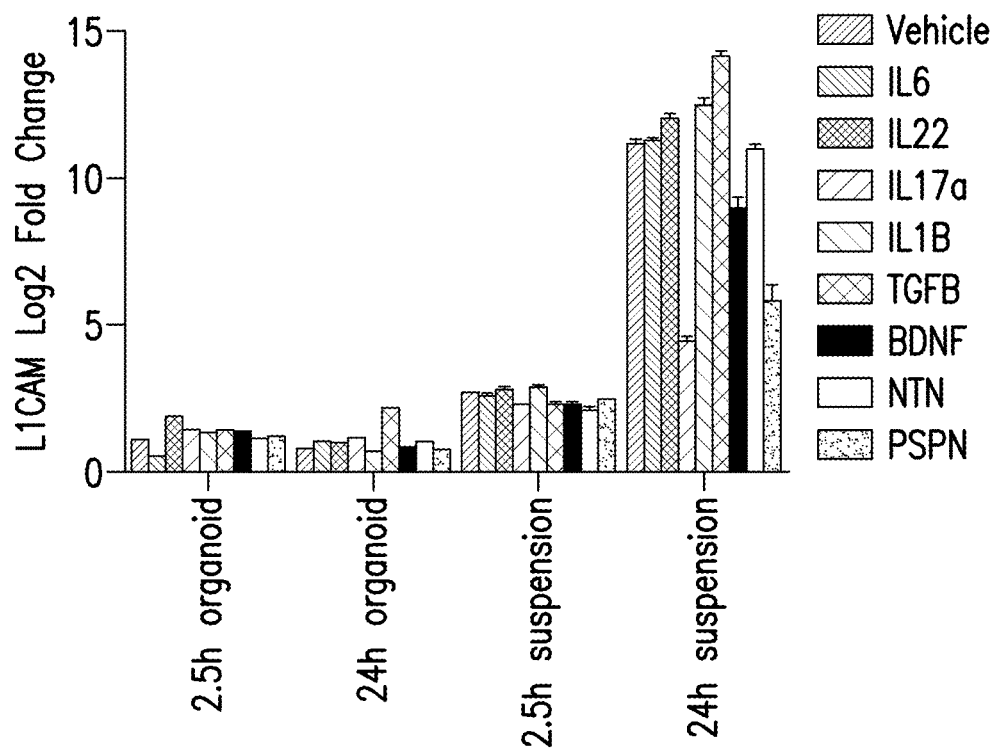
Figure 30C:
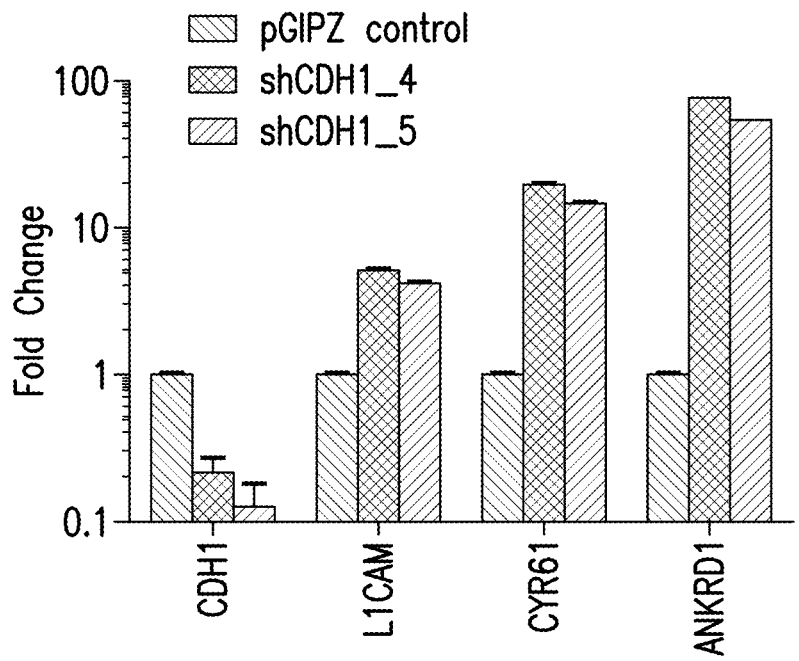

Next, we sought to understand how epithelial progenitor cells induce and regulate L1CAM expression. To determine whether colitis-associated inflammatory cytokines might contribute to L1CAM induction, we incubated human CRC organoids with conditioned media from normal or inflamed colons. Neither colitis conditioned-media nor incubation with recombinant cytokines associated with colitis or neuronal regeneration (where L1CAM has been previously implicated) induced L1CAM (FIG. 30A-B). In contrast, dissociation of organoids into single cells was necessary and sufficient for L1CAM upregulation (FIG. 30A-B). Structural integrity in intact epithelia is secured by e-cadherin homophilic cell-cell contacts in adherens junctions. We therefore hypothesized that loss of e-cadherin from the cell membrane in disrupted epithelia might induce L1CAM expression. Consistent with this hypothesis, shRNA-mediated knockdown of e-cadherin in CRC organoids induced L1CAM and YAP target gene expression (FIG. 30C).

Figure 30D:
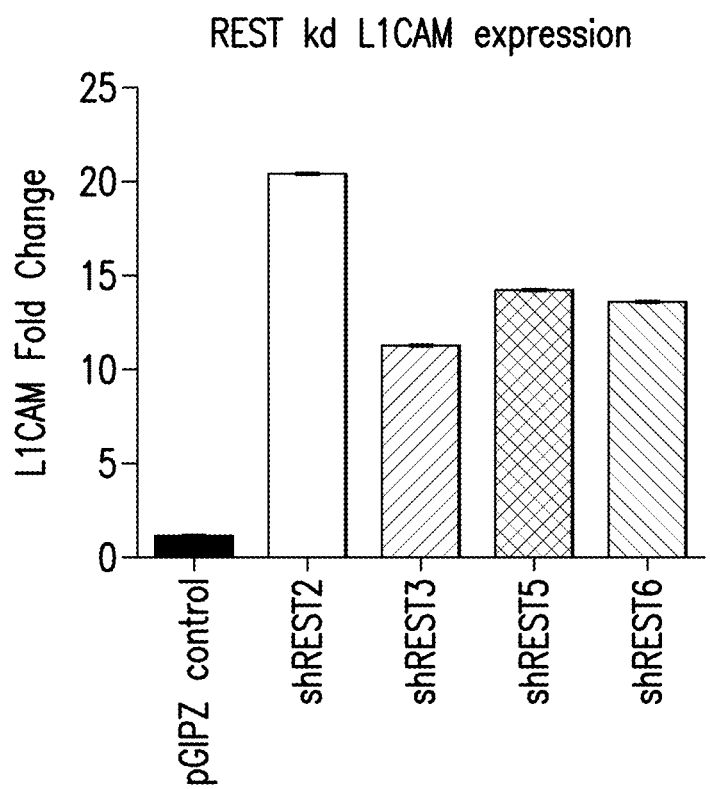
Figure 30E:
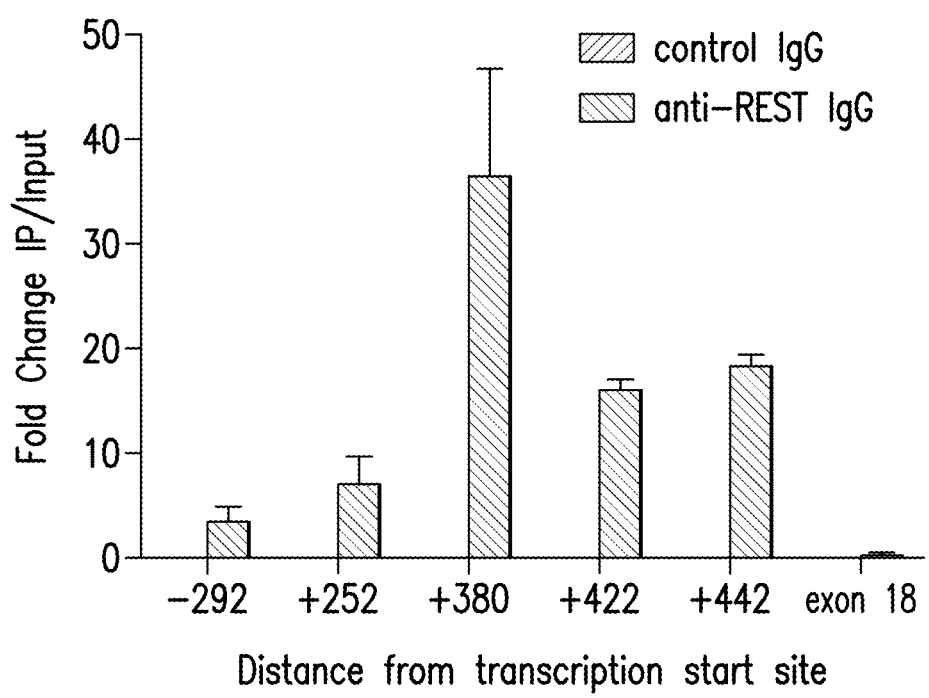
Figure 30F:
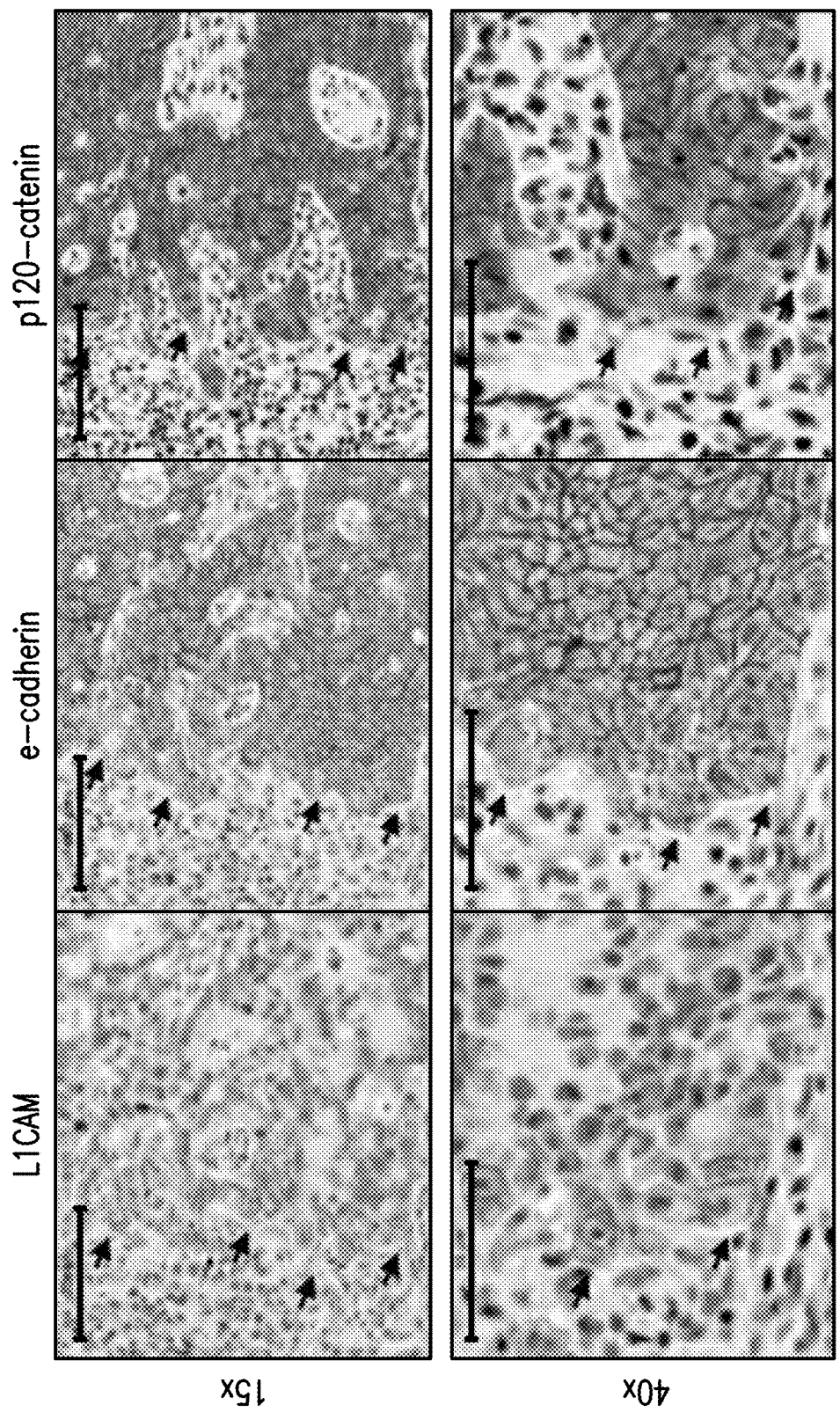

In various non-neuronal tissues, the transcriptional repressor NSRF/REST normally prevents the expression of L1CAM and other neuronal genes. REST has been identified as a tumor suppressor and metastatic colorectal cancers frequently acquire loss-of-function mutations or deletions in the REST gene. We therefore investigated whether REST is functional in repressing L1CAM expression in organoids. REST knockdown in human CRC organoids strongly induced L1CAM expression, suggesting that REST is active in repressing L1CAM expression (FIG. 30D). CHIP-PCR specifically pulled down REST bound to an intronic enhancer in the first intron of the L1CAM locus in CRC organoids (FIG. 30E). To verify whether epithelial disruption is associated with L1CAM expression in patient tumors, we stained serial sections of primary CRC invasion fronts with antibodies against e-cadherin and REST. We identified a strong correlation between loss of membranous e-cadherin and L1CAM expression in patient tumors (FIG. 30F). These results indicate that L1CAM is required for the survival of cells that are deprived of epithelial integrity, and is downregulated in intact epithelia.

12. REFERENCES

Allgayer, H., Heiss, M. M., and Schildberg, F. W. (1997). Prognostic factors in gastric cancer. Br J Surg 84, 1651-1664.

Altevogt P, Doberstein K, Fogel M. L1CAM in human cancer. Int J Cancer. 2015 Jun. 25.

Ashkenazi, A., and Dixit, V. M. (1998). Death receptors: signaling and modulation. Science 281, 1305-1308.

Bao et al. (2008) Cancer Res. 68(15):6043-6048.

Ben Q W, Wang J C, Liu J, Zhu Y, Yuan F, Yao W Y, Yuan Y Z. Positive expression of L1-CAM is associated with perineural invasion and poor outcome in pancreatic ductal adenocarcinoma. Ann Surg Oncol. 2010 August; 17(8): 2213-21.

Ben Q W, Wang J C, Liu J, Zhu Y, Yuan F, Yao W Y, Yuan Y Z. (2010) Positive expression of L1-CAM is associated with perineural invasion and poor outcome in pancreatic ductal adenocarcinoma. Ann Surg Oncol. 17(8):2213-21.

Blouw, B., Song, H., Tihan, T., Bosze, J., Ferrara, N., Gerber, H. P., Johnson, R. S., and Bergers, G. (2003). The hypoxic response of tumors is dependent on their microenvironment. Cancer Cell 4, 133-146.

Boo, Y. J., Park, J. M., Kim, J., Chae, Y. S., Min, B. W., Um, J. W., and Moon, H. Y. (2007). L1 expression as a marker for poor prognosis, tumor progression, and short survival in patients with colorectal cancer. Ann Surg Oncol 14, 1703-1711.

Bos, P. D., Zhang, X. H., Nadal, C., Shu, W., Gomis, R. R., Nguyen, D. X., Minn, A. J., van de Vijver, M. J., Gerald, W. L., Foekens, J. A., et al. (2009). Genes that mediate breast cancer metastasis to the brain. Nature 459, 1005-1009.

Carbonell, W. S., Ansorge, O., Sibson, N., and Muschel, R. (2009). The vascular basement membrane as "soil" in brain metastasis. PloS one 4, e5857.

Castellani, V., De Angelis, E., Kenwrick, S., and Rougon, G. (2002). Cis and trans interactions of L1 with neuropilin-1 control axonal responses to semaphorin 3A. EMBO J 21, 6348-6357.

Chambers, A. F., Groom, A. C., and MacDonald, I. C. (2002). Dissemination and growth of cancer cells in metastatic sites. Nat Rev Cancer 2, 563-572.

Chambers, A. M., I; Schmidt, E; Morris, V; Groom, A (2000). Clinical targets for antimetastasis therapy. Adv Cancer Res 79, 91-121.

Chen D L, Zeng Z L, Yang J, Ren C, Wang D S, Wu W J, Xu R H. (2013) L1CAM promotes tumor progression and metastasis and is an independent unfavorable prognostic factor in gastric cancer. J Hematol Oncol. 6:43.

Cho S, Park I, Kim H, Jeong M S, Lim M, Lee E S, Kim J H, Kim S, Hong H J. (2016) Generation, characterization and preclinical studies of a human anti-L1CAM monoclonal antibody that cross-reacts with rodent L1CAM. MAbs. 8(2):414-25.

Demyanenko, G. P., Tsai, A. Y., and Maness, P. F. (1999). Abnormalities in neuronal process extension, hippocampal development, and the ventricular system of L1 knockout mice. J Neurosci 19, 4907-4920.

Dietrich, P. Y., Walker, P. R., and Saas, P. (2003). Death receptors on reactive astrocytes: a key role in the fine tuning of brain inflammation? Neurology 60, 548-554.

Dippel V, Milde-Langosch K, Wicklein D, Schumacher U, Altevogt P, Oliveira-Ferrer L, Jänicke F, Schroder C. (2013). Influence of L1-CAM expression of breast cancer cells on adhesion to endothelial cells. J Cancer Res Clin Oncol. 2013 January; 139(1): 107-21. doi: 10.1007/s00432-012-1306-z. Epub 2012 Sep. 16.

Doberstein, K., Wieland, A., Lee, S. B., Blaheta, R. A., Wedel, S., Moch, H., Schraml, P., Pfeilschifter, J., Kristiansen, G., and Gutwein, P. (2011). L1-CAM expression in ccRCC correlates with shorter patients survival times and confers chemoresistance in renal cell carcinoma cells. Carcinogenesis 32, 262-270.

Doberstein K, Harter P N, Haberkorn U, Bretz N P, Arnold B, Carretero R, Moldenhauer G, Mittelbronn M, Altevogt P. (2015) Antibody therapy to human L1CAM in a transgenic mouse model blocks local tumor growth but induces EMT. Int J Cancer. 136(5):e326-39.

Donier, E., Gomez-Sanchez, J. A., Grijota-Martinez, C., Lakoma, J., Baars, S., Garcia-Alonso, L., and Cabedo, H. (2012). L1CAM binds ErbB receptors through Ig-like domains coupling cell adhesion and neuregulin signalling. PloS one 7, e40674.

Drost et al., 2016, Organoid culture systems for prostate epithelial and cancer tissue, Nature Protocols 11:347-358.

Feld, R., Rubinstein, L. V., and Weisenberger, T. H. (1984). Sites of recurrence in resected stage I non-small-cell lung cancer: a guide for future studies. J Clin Oncol 2, 1352-1358.

Felding-Habermann, B., Silletti, S., Mei, F., Siu, C. H., Yip, P. M., Brooks, P. C., Cheresh, D. A., O'Toole, T. E., Ginsberg, M. H., and Montgomery, A. M. (1997). A single immunoglobulin-like domain of the human neural cell adhesion molecule L1 supports adhesion by multiple vascular and platelet integrins. J Cell Biol 139, 1567-1581.

Fidler, I. J. (2003). The pathogenesis of cancer metastasis: the 'seed and soil' hypothesis revisited. Nat Rev Cancer 3, 453-458.

Foekens, J. A., Look, M. P., Peters, H. A., van Putten, W. L., Portengen, H., and Klijn, J. G. (1995). Urokinase-type plasminogen activator and its inhibitor PAI-1: predictors of poor response to tamoxifen therapy in recurrent breast cancer. J Natl Cancer Inst 87, 751-756.

Fogel, M., Gutwein, P., Mechtersheimer, S., Riedle, S., Stoeck, A., Smirnov, A., Edler, L., Ben-Arie, A., Huszar, M., and Altevogt, P. (2003a). L1 expression as a predictor of progression and survival in patients with uterine and ovarian carcinomas. Lancet 362, 869-875.

Fogel M, Mechtersheimer S, Huszar M, Smirnov A, Abu-Dahi A, Tilgen W, Reichrath J, Georg T, Altevogt P, Gutwein P. (2003) L1 adhesion molecule (CD 171) in development and progression of human malignant melanoma. Cancer Lett. 189(2):237-47.

Francia, G., Cruz-Munoz, W., Man, S., Xu, P., and Kerbel, R. S. (2011). Mouse models of advanced spontaneous metastasis for experimental therapeutics. Nat Rev Cancer 11, 135-141.

Ganesh, B. S., and Chintala, S. K. (2011). Inhibition of reactive gliosis attenuates excitotoxicity-mediated death of retinal ganglion cells. PloS one 6, e18305.

Gavrilovic, I. T., and Posner, J. B. (2005). Brain metastases: epidemiology and pathophysiology. J Neurooncol 75, 5-14.

Gupta, G. P., and Massagué, J. (2006). Cancer metastasis: building a framework. Cell 127, 679-695.

Hai, J., Zhu, C. Q., Bandarchi, B., Wang, Y. H., Navab, R., Shepherd, F. A., Jurisica, I., and Tsao, M. S. (2012). L1 cell adhesion molecule promotes tumorigenicity and metastatic potential in non-small cell lung cancer. Clin Cancer Res 18, 1914-1924.

Hanahan D, Weinberg R A. Hallmarks of cancer: the next generation. (2011) Cell. 144(5):646-74.

Harbeck, N., Thomssen, C., Berger, U., Ulm, K., Kates, R. E., Hofler, H., Janicke, F., Graeff, H., and Schmitt, M. (1999). Invasion marker PAI-1 remains a strong prognostic factor after long-term follow-up both for primary breast cancer and following first relapse. Breast Cancer Res Treat 54, 147-157.

Herron, L. R., Hill, M., Davey, F., and Gunn-Moore, F. J. (2009). The intracellular interactions of the L1 family of cell adhesion molecules. Biochem J 419, 519-531.

Heyn, C., Ronald, J. A., Ramadan, S. S., Snir, J. A., Barry, A. M., MacKenzie, L. T., Mikulis, D. J., Palmieri, D., Bronder, J. L., Steeg, P. S., et al. (2006). In vivo MRI of cancer cell fate at the single-cell level in a mouse model of breast cancer metastasis to the brain. Magn Reson Med 56, 1001-1010.

Hoffman, E/. Minthz, C. D., Wang, S., McNickie, D, m Salton, S., Benson, D. (2008) Effects of alcohol on axon outgrowth and branching in developing rat cortical neurons. Neurosci. 157(3), 556-565.

Hong H, Stastny M, Brown C, Chang W C, Ostberg J R, Forman S J, Jensen M C. (2014) Diverse solid tumors expressing a restricted epitope of L1-CAM can be targeted by chimeric antigen receptor redirected T lymphocytes. J Immunother. 37(2):93-104.

Kang, Y., Siegel, P. M., Shu, W., Drobnjak, M., Kakonen, S. M., Cordón-Cardo, C., Guise, T. A., and Massagué, J. (2003). A multigenic program mediating breast cancer metastasis to bone. Cancer Cell 3, 537-549.

Karrison, T. G., Ferguson, D. J., and Meier, P. (1999). Dormancy of mammary carcinoma after mastectomy. J Natl Cancer Inst 91, 80-85.

Kienast, Y., von Baumgarten, L., Fuhrmann, M., Klinkert, W. E., Goldbrunner, R., Herms, J., and Winkler, F. (2010). Real-time imaging reveals the single steps of brain metastasis formation. Nat Med 16, 116-122.

Kim H S, Yi S Y, Jun H J, Ahn J S, Ahn M J, Lee J, Kim Y, Cui Z Y, Hong H J, Kim J M, Li S, Hwang I G, Park K. (2009) L1 cell adhesion molecule as a predictor for recurrence in pulmonary carcinoids and large-cell neuroendocrine tumors. APMIS. 117(2): 140-6.

Kim, S. J., Kim, J. S., Park, E. S., Lee, J. S., Lin, Q., Langley, R. R., Maya, M., He, J., Kim, S. W., Weihua, Z., et al. (2011). Astrocytes upregulate survival genes in tumor cells and induce protection from chemotherapy. Neoplasia 13, 286-298.

Krammer, P. H. (2000). CD95's deadly mission in the immune system. Nature 407, 789-795.

Kulahin, N., Li, S., Hinsby, A., Kiselyov, V., Berezin, V., and Bock, E. (2008). Fibronectin type III (FN3) modules of the neuronal cell adhesion molecule L1 interact directly with the fibroblast growth factor (FGF) receptor. Mol Cell Neurosci 37, 528-536.

Law, R. H., Zhang, Q., McGowan, S., Buckle, A. M., Silverman, G. A., Wong, W., Rosado, C. J., Langendorf, C. G., Pike, R. N., Bird, P. I., et al. (2006). An overview of the serpin superfamily. Genome Biol 7, 216.

Lee E S, Jeong M S, Singh R, Jung J, Yoon H, Min J K, Kim K H, Hong H J. A chimeric antibody to L1 cell adhesion molecule shows therapeutic effect in an intrahepatic cholangiocarcinoma model. Exp Mol Med. 2012 Apr. 30; 44(4):293-302.

Leenders, W. P., Kusters, B., and de Waal, R. M. (2002). Vessel co-option: how tumors obtain blood supply in the absence of sprouting angiogenesis. Endothelium 9, 83-87.

Leenders, W. P., Kusters, B., Verrijp, K., Maass, C., Wesseling, P., Heerschap, A., Ruiter, D., Ryan, A., and de Waal, R. (2004). Antiangiogenic therapy of cerebral melanoma metastases results in sustained tumor progression via vessel co-option. Clin Cancer Res 10, 6222-6230.

Leyland-Jones, B. (2009). Human epidermal growth factor receptor 2-positive breast cancer and central nervous system metastases. J Clin Oncol 27, 5278-5286.

Li, B., Wang, C., Zhang, Y., Zhao, X. Y., Huang, B., Wu, P. F., Li, Q., Li, H., Liu, Y. S., Cao, L. Y., et al. (2013). Elevated PLGF contributes to small-cell lung cancer brain metastasis. Oncogene 32, 2952-2962.

Lin, N. U., and Winer, E. P. (2007). Brain metastases: the HER2 paradigm. Clin Cancer Res 13, 1648-1655.

Lin, Q. B., K.; Fan, D.; Kim, S-J.; Guo, L.; Wang, H.; Bar-Eli, M.; Aldape, K. D.; Fidler, I. J. (2010). Reactive astrocytes protect melanoma cells from chemotherapy by sequestering intracellular calcium through gap junction communication channels. Neoplasia 12, 748-754.

Lindenblatt D, Fischer E, Cohrs S, Schibli R, Grunberg J. Paclitaxel improved anti-L1CAM lutetium-177 radioimmunotherapy in an ovarian cancer xenograft model. EJNMMI Res. 2014 December; 4(1):54.

Lorger, M., and Felding-Habermann, B. (2010). Capturing changes in the brain microenvironment during initial steps of breast cancer brain metastasis. Am J Pathol 176, 2958-2971.

Luo J L, Tan W, Ricono J M, Korchynskyi O, Zhang M, Gonias S L, Cheresh D A, Karin M. (2007). "Nuclear cytokine-activated IKKalpha controls prostate cancer metastasis by repressing Maspin". Nature. 446 (7136): 690-4. doi:10.1038/nature05656. PMID 17377533.

Lutterbach, J., Bartelt, S., and Ostertag, C. (2002). Long-term survival in patients with brain metastases. J Cancer Res Clin Oncol 128, 417-425.

Maher, E. A., Mietz, J., Arteaga, C. L., DePinho, R. A., and Mohla, S. (2009). Brain metastasis: opportunities in basic and translational research. Cancer Res 69, 6015-6020.

Malladi S, Macalinao D G, Jin X, He L, Basnet H, Zou Y, de Stanchina E, Massagué J. Metastatic latency and immune evasion through autocrine inhibition of WNT. Cell. 2016 Mar. 24; 165(1):45-60.

Maness, P. F., and Schachner, M. (2007). Neural recognition molecules of the immunoglobulin superfamily: signaling transducers of axon guidance and neuronal migration. Nat Neurosci 10, 19-26.

Mechtersheimer, S., Gutwein, P., Agmon-Levin, N., Stoeck, A., Oleszewski, M., Riedle, S., Postina, R., Fahrenholz, F., Fogel, M., Lemmon, V., et al. (2001). Ectodomain shedding of L1 adhesion molecule promotes cell migration by autocrine binding to integrins. J Cell Biol 155, 661-673.

Meuwissen, R., Linn, S. C., Linnoila, R. I., Zevenhoven, J., Mooi, W. J., and Berns, A. (2003). Induction of small cell lung cancer by somatic inactivation of both Trp53 and Rb 1 in a conditional mouse model. Cancer Cell 4, 181-189.

Minn, A. J., Gupta, G. P., Siegel, P. M., Bos, P. D., Shu, W., Giri, D. D., Viale, A., Olshen, A. B., Gerald, W. L., and Massagué, J. (2005). Genes that mediate breast cancer metastasis to lung. Nature 436, 518-524.

Mire E., Thomasett, N., Jakeman, L., Rougon, G, (2008) Modulating Sema3A signal with a L1 mimetic peptide is not sufficient to promote motor recovery and axon regeneration after spinal cord injury. Mol. Cell. Neurosci. 37(2), 222-235.

Moody, S. E., Sarkisian, C. J., Hahn, K. T., Gunther, E. J., Pickup, S., Dugan, K. D., Innocent, N., Cardiff, R. D., Schnall, M. D., and Chodosh, L. A. (2002). Conditional activation of Neu in the mammary epithelium of transgenic mice results in reversible pulmonary metastasis. Cancer Cell 2, 451-461.

Nguyen, D. X., Bos, P. D., and Massagué, J. (2009a). Metastasis: from dissemination to organ-specific colonization. Nat Rev Cancer 9, 274-284.

Nguyen, D. X., Chiang, A. C., Zhang, X. H., Kim, J. Y., Kris M. G., Ladanyi, M., Gerald, W. L., and Massagué, J. (2009b). WNT/TCF signaling through LEF1 and HOXB9 mediates lung adenocarcinoma metastasis. Cell 138, 51-62.

Oskarsson T, Batlle E, Massagué J. Metastatic stem cells: sources, niches, and vital pathways. Cell Stem Cell. 2014 Mar. 6; 14(3):306-21.

Palmieri, D., Bronder, J. L., Herring, J. M., Yoneda, T., Weil, R. J., Stark, A. M., Kurek, R., Vega-Valle, E., Feigenbaum, L., Halverson, D., et al. (2007). Her-2 overexpression increases the metastatic outgrowth of breast cancer cells in the brain. Cancer Res 67, 4190-4198.

Park J R, Digiusto D L, Slovak M, Wright C, Naranjo A, Wagner J, Meechoovet H B, Bautista C, Chang W C, Ostberg J R, Jensen M C. Adoptive transfer of chimeric antigen receptor re-directed cytolytic T lymphocyte clones in patients with neuroblastoma. Mol Ther. 2007 April; 15(4):825-33.

PCT/US2014/056379, filed Sep. 18, 2014

Perera, M., Ribot, E. J., Percy, D. B., McFadden, C., Simedrea, C., Palmieri, D., Chambers, A. F., and Foster, P. J. (2012). In vivo magnetic resonance imaging for investigating the development and distribution of experimental brain metastases due to breast cancer. Transl Oncol 5, 217-225.

Polleux, F., and Ghosh, A. (2002). The slice overlay assay: a versatile tool to study the influence of extracellular signals on neuronal development. Sci STKE 136, 19-29.

Qian, Y., Hua, E., Bisht, K., Woditschka, S., Skordos, K. W., Liewehr, D. J., Steinberg, S. M., Brogi, E., Akram, M. M., Killian, J. K., et al. (2011). Inhibition of Polo-like kinase 1 prevents the growth of metastatic breast cancer cells in the brain. Clin Exp Metastasis 28, 899-908.

Rathj en F G, Schachner M. Immunocytological and biochemical characterization of a new neuronal cell surface component (L1 antigen) which is involved in cell adhesion. EMBO J. 1984 January; 3(1):1-10.

Regales, L., Gong, Y., Shen, R., de Stanchina, E., Vivanco, I., Goel, A., Koutcher, J. A., Spassova, M., Ouerfelli, O., Mellinghoff, I. K., et al. (2009). Dual targeting of EGFR can overcome a major drug resistance mutation in mouse models of EGFR mutant lung cancer. J Clin Invest 119, 3000-3010.

Schafer, M. K., and Altevogt, P. (2010). L1CAM malfunction in the nervous system and human carcinomas. Cell Mol Life Sci 67, 2425-2437.

Schäfer H, Dieckmann C, Korniienko O, Moldenhauer G, Kiefel H, Salnikov A, Kruger A, Altevogt P, Sebens S. Combined treatment of L1CAM antibodies and cytostatic drugs improve the therapeutic response of pancreatic and ovarian carcinoma. Cancer Lett. 2012 Jun. 1; 319(1):66-82.

Schildge, S., Bohrer, C., Beck, K., and Schachtrup, C. (2013). Isolation and culture of mouse cortical astrocytes. Journal of visualized experiments: JoVE.

Schmidt-Kittler, O., Ragg, T., Daskalakis, A., Granzow, M., Ahr, A., Blankenstein, T. J., Kaufmann, M., Diebold, J., Arnholdt, H., Muller, P., et al. (2003). From latent disseminated cells to overt metastasis: genetic analysis of systemic breast cancer progression. Proc Natl Acad Sci USA 100, 7737-7742.

Schouten, L. J., Rutten, J., Huveneers, H. A., and Twijnstra, A. (2002). Incidence of brain metastases in a cohort of patients with carcinoma of the breast, colon, kidney, and lung and melanoma. Cancer 94, 2698-2705.

Schmohl and Vallera, 2016, Toxins 8(6):165.

Schreiber, R. D., Old, L. J., and Smyth, M. J. (2011). Cancer immunoediting: integrating immunity's roles in cancer suppression and promotion. Science 331, 1565-1570.

Schroder, C., Schumacher, U., Fogel, M., Feuerhake, F., Muller, V., Wirtz, R. M., Altevogt, P., Krenkel, S., Janicke, F., and Milde-Langosch, K. (2009). Expression and prognostic value of L1-CAM in breast cancer. Oncol Rep 22, 1109-1117.

Seike, T., Fujita, K., Yamakawa, Y., Kido, M. A., Takiguchi, S., Teramoto, N., Iguchi, H., and Noda, M. (2011). Interaction between lung cancer cells and astrocytes via specific inflammatory cytokines in the microenvironment of brain metastasis. Clin Exp Metastasis 28, 13-25.

Siegel, P. M., Shu, W., Cardiff, R. D., Muller, W. J., and Massagué, J. (2003). Transforming growth factor beta signaling impairs Neu-induced mammary tumorigenesis while promoting pulmonary metastasis. Proc Natl Acad Sci USA 100, 8430-8435.

Sledge, G. W., Jr. (2011). HER2011: the changing face of HER2-positive breast cancer. Clin Breast Cancer 11, 9.

Sofroniew, M. V., and Vinters, H. V. (2010). Astrocytes: biology and pathology. Acta Neuropathol Suppl (Berl) 119, 7-35.

Steeg, P. S., Camphausen, K. A., and Smith, Q. R. (2011). Brain metastases as preventive and therapeutic targets. Nat Rev Cancer 11, 352-363.

Thies, A., Schachner, M., Moll, I., Berger, J., Schulze, H. J., Brunner, G., and Schumacher, U. (2002). Overexpression of the cell adhesion molecule L1 is associated with metastasis in cutaneous malignant melanoma. Eur J Cancer 38, 1708-1716.

Tischler, V., Pfeifer, M., Hausladen, S., Schirmer, U., Bonde, A. K., Kristiansen, G., Sos, M. L., Weder, W., Moch, H., Altevogt, P., et al. (2011). L1CAM protein expression is associated with poor prognosis in non-small cell lung cancer. Mol Cancer 10, 127-137.

Tsutsumi, S., Morohashi, S., Kudo, Y., Akasaka, H., Ogasawara, H., Ono, M., Takasugi, K., Ishido, K., Hakamada, K., and Kijima, H. (2011). L1 Cell adhesion molecule (L1CAM) expression at the cancer invasive front is a novel prognostic marker of pancreatic ductal adenocarcinoma. J Surg Oncol 103, 669-673.

U.S. Pat. No. 8,138,313, International Patent Application Publication No. WO 2007114550, and International Patent Application Publication No. WO 2008151819.

Valastyan, S., and Weinberg, R. A. (2011). Tumor metastasis: molecular insights and evolving paradigms. Cell 147, 275-292.

Valiente M, Obenauf A C, Jin X, Chen Q, Zhang X H, Lee D J, Chaft J E, Kris M G, Huse J T, Brogi E, Massagué J. Serpins promote cancer cell survival and vascular co-option in brain metastasis. Cell. 2014 Feb. 27; 156(5): 1002-16.

Vanharanta, S., and Massagué, J. (2013). Origins of metastatic traits. Cancer Cell. 2013 Oct. 14; 24(4):410-21. doi: 10.1016/j.ccr.2013.09.007.

Vos, Y. J., and Hofstra, R. M. (2010). An updated and upgraded L1CAM mutation database. Hum Mutat 31, E1102-1109.

Voura, E. B., Ramjeesingh, R. A., Montgomery, A. M., and Siu, C. H. (2001). Involvement of integrin alpha(v)beta(3) and cell adhesion molecule L1 in transendothelial migration of melanoma cells. Mol Biol Cell 12, 2699-2710.

Wang, X., Haroon, F., Karray, S., Martina, D., and Schluter, D. (2013). Astrocytic Fas ligand expression is required to induce T-cell apoptosis and recovery from experimental autoimmune encephalomyelitis. Eur J Immunol 43, 115-124.

Wang Y, Loers G, Pan H C, Gouveia R, Zhao W J, Shen Y Q, Kleene R, Costa J, Schachner M. Antibody fragments directed against different portions of the human neural cell adhesion molecule L1 act as inhibitors or activators of L1 function. PLoS One. 2012; 7(12):e52404.

Wiencken-Barger, A. E., Mavity-Hudson, J., Bartsch, U., Schachner, M., and Casagrande, V. A. (2004). The role of L1 in axon pathfinding and fasciculation. Cereb Cortex 14, 121-131.

Winslow, M. M., Dayton, T. L., Verhaak, R. G., Kim-Kiselak, C., Snyder, E. L., Feldser, D. M., Hubbard, D. D., DuPage, M. J., Whittaker, C. A., Hoersch, S., et al. (2011). Suppression of lung adenocarcinoma progression by Nkx2-1. Nature 473, 101-104.

Wolterink S, Moldenhauer G, Fogel M, Kiefel H, Pfeifer M, Liittgau S, Gouveia R, Costa J, Endell J, Moebius U, Altevogt P. Therapeutic antibodies to human L1CAM: functional characterization and application in a mouse model for ovarian carcinoma. Cancer Res. 2010 Mar. 15; 70(6):2504-15.

Zhu, C. Q., Ding, K., Strumpf, D., Weir, B. A., Meyerson, M., Pennell, N., Thomas, R. K., Naoki, K., Ladd-Acosta, C., Liu, N., et al. (2010). Prognostic and predictive gene signature for adjuvant chemotherapy in resected non-small-cell lung cancer. J Clin Oncol 28, 4417-4424.

Various publications are cited herein, the contents of which are hereby incorporated by reference in their entireties.

What is claimed is:

1. A method of reducing the risk, in a subject who has received treatment for a primary cancer, of metastatic spread of the primary cancer, comprising administering to the subject a therapeutic amount of a L1CAM inhibitor, wherein the L1CAM inhibitor is administered:
   (a) at least one month after a course of chemotherapy, targeted therapy, immunotherapy and/or radiotherapy of the primary cancer is completed;
   (b) after the subject has achieved remission of the primary cancer; or
   (c) after a surgical excision of the primary cancer or a metastasis has been completed.

2. The method of claim 1, where the L1CAM inhibitor is administered in a maintenance regimen.

3. The method of claim 2, wherein the L1CAM inhibitor is administered at least once a week, at least once a month, at least once every two months, at least once every three months, or at least once every six months.

4. The method of claim 1, wherein the L1CAM inhibitor is an immunoglobulin.

5. The method of claim 4, wherein the L1CAM inhibitor is an immunoglobulin bispecific for L1CAM and CD133 or an immunoglobulin bispecific for L1CAM and CD44.

6. The method of claim 1, wherein the L1CAM inhibitor is an interfering RNA or an antisense RNA.

7. The method of claim 1, wherein the primary cancer is breast cancer, lung cancer, renal cancer, or colorectal cancer.

8. A method of inhibiting metastatic spread of a primary cancer in a subject who has received treatment for the primary cancer, comprising administering to the subject a therapeutic amount of a L1CAM inhibitor, wherein the L1CAM inhibitor is administered:
   (a) at least one month after a course of chemotherapy, targeted therapy, immunotherapy and/or radiotherapy of the primary cancer is completed;
   (b) after the subject has achieved remission of the primary cancer; or
   (c) after a surgical excision of the primary cancer or a metastasis has been completed.

9. A method of inhibiting progression of metastatic disease in a subject who has received treatment for the primary cancer, comprising administering to the subject a therapeutic amount of a L1CAM inhibitor, wherein the L1CAM inhibitor is administered:
   (a) at least one month after a course of chemotherapy, targeted therapy, immunotherapy and/or radiotherapy of the primary cancer is completed;
   (b) after the subject has achieved remission of the primary cancer; or
   (c) after a surgical excision of the primary cancer or a metastasis has been completed.

10. The method of claim 8, wherein the L1CAM inhibitor is administered at least once a week, at least once a month, at least once every two months, at least once every three months, or at least once every six months.

11. The method of claim 8, wherein the L1CAM inhibitor is an immunoglobulin.

12. The method of claim 8, wherein the primary cancer is breast cancer, lung cancer, renal cancer, or colorectal cancer.

13. The method of claim 9, wherein the L1CAM inhibitor is administered at least once a week, at least once a month, at least once every two months, at least once every three months, or at least once every six months.

14. The method of claim 9, wherein the L1CAM inhibitor is an immunoglobulin.

15. The method of claim 9, wherein the primary cancer is breast cancer, lung cancer, renal cancer, or colorectal cancer.

* * * * *